US011376073B2

(12) United States Patent
Frey et al.

(10) Patent No.: US 11,376,073 B2
(45) Date of Patent: *Jul. 5, 2022

(54) PATIENT-MATCHED APPARATUS AND METHODS FOR PERFORMING SURGICAL PROCEDURES

(71) Applicant: Mighty Oak Medical, Inc., Englewood, CO (US)

(72) Inventors: George Frey, Englewood, CO (US); Geoff Lai, Lakewood, CO (US); Caleb Voelkel, Lakewood, CO (US)

(73) Assignee: Mighty Oak Medical Inc., Englewood, CO (US)

( * ) Notice: Subject to any disclaimer, the term of this patent is extended or adjusted under 35 U.S.C. 154(b) by 434 days.

This patent is subject to a terminal disclaimer.

(21) Appl. No.: 16/598,861

(22) Filed: Oct. 10, 2019

(65) Prior Publication Data

US 2020/0138519 A1 May 7, 2020

Related U.S. Application Data

(63) Continuation-in-part of application No. 15/997,404, filed on Jun. 4, 2018, now Pat. No. 11,039,889, which
(Continued)

(51) Int. Cl.
*A61B 34/10* (2016.01)
(52) U.S. Cl.
CPC ........ *A61B 34/10* (2016.02); *A61B 2034/102* (2016.02); *A61B 2034/105* (2016.02); *A61B 2034/107* (2016.02); *A61B 2034/108* (2016.02)
(58) Field of Classification Search
CPC ............. A61B 34/10; A61B 2034/102; A61B 2034/105; A61B 2034/107;
(Continued)

(56) References Cited

U.S. PATENT DOCUMENTS 3,151,392 A 10/1964 Chambers
5,201,734 A 4/1993 Cozad et al.
(Continued)

FOREIGN PATENT DOCUMENTS

CA 2736525 3/2010
CA 2862341 8/2013
(Continued)

OTHER PUBLICATIONS

Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.
(Continued)

*Primary Examiner* — Sanjay Cattungal
(74) *Attorney, Agent, or Firm* — FisherBroyles LLP; Ian R. Walsworth

(57) ABSTRACT

A system and method for developing customized apparatus, such as occipital guides, for use in one or more surgical procedures is disclosed. The system and method incorporates a patient's unique anatomical features or morphology, which may be derived from capturing MRI data or CT data, to fabricate at least one custom apparatus or guide. According to a preferred embodiment, the customized apparatus comprises at least one patient-specific surface and or contour. Apparatus, including one or more surgical guides, may be matched in duplicate and oriented around the patient's own anatomy, and may further provide any desired axial alignments or insertional trajectories. In an alternate embodiment, the apparatus may further be aligned and/or matched with at least one other apparatus during the surgical procedure.

15 Claims, 48 Drawing Sheets

Related U.S. Application Data is a continuation-in-part of application No. 15/416,975, filed on Jan. 26, 2017, now Pat. No. 9,987,024, which is a continuation-in-part of application No. 14/883,299, filed on Oct. 14, 2015, now Pat. No. 9,642,633, which is a continuation-in-part of application No. 14/298,634, filed on Jun. 6, 2014, now Pat. No. 9,198,678, which is a continuation-in-part of application No. 13/841,069, filed on Mar. 15, 2013, now Pat. No. 8,870,889, which is a continuation-in-part of application No. 13/172,683, filed on Jun. 29, 2011, now Pat. No. 8,758,357.

(60) Provisional application No. 62/743,661, filed on Oct. 10, 2018, provisional application No. 62/628,626, filed on Feb. 9, 2018, provisional application No. 61/887,837, filed on Sep. 13, 2013, provisional application No. 61/845,463, filed on Jul. 12, 2013, provisional application No. 61/832,583, filed on Jun. 7, 2013, provisional application No. 61/625,559, filed on Apr. 17, 2012, provisional application No. 61/393,695, filed on Oct. 15, 2010, provisional application No. 61/359,710, filed on Jun. 29, 2010.

(58) Field of Classification Search
CPC .......... A61B 2034/108; A61B 17/7067; A61B 17/1617; A61B 17/1671; A61B 90/11; A61B 34/20; A61B 2017/568; A61B 17/1757; A61B 17/7071
See application file for complete search history.

(56) References Cited

U.S. PATENT DOCUMENTS

| | | |
|---|---|---|
| D359,557 S | 6/1995 | Hayes |
| 5,490,409 A | 2/1996 | Weber |
| 5,527,312 A | 6/1996 | Ray |
| 5,569,246 A | 10/1996 | Ojima et al. |
| D403,066 S | 12/1998 | DeFonzo |
| 5,865,846 A | 2/1999 | Bryan et al. |
| D412,032 S | 7/1999 | Mikula-Curtis et al. |
| 5,993,453 A | 11/1999 | Bullara et al. |
| 6,006,581 A | 12/1999 | Holmes |
| D420,132 S | 2/2000 | Bucholz et al. |
| 6,030,401 A | 2/2000 | Marino |
| 6,035,691 A | 3/2000 | Lin et al. |
| 6,063,088 A | 5/2000 | Winslow |
| D428,989 S | 8/2000 | Segermark et al. |
| 6,113,602 A | 9/2000 | Sand |
| 6,142,998 A | 11/2000 | Smith et al. |
| 6,221,077 B1 | 4/2001 | Rinner et al. |
| 6,290,724 B1 | 9/2001 | Marino |
| 6,309,395 B1 | 10/2001 | Smith et al. |
| 6,328,738 B1 | 12/2001 | Suddaby |
| 6,364,880 B1 | 4/2002 | Michelson |
| 6,644,087 B1 | 11/2003 | Ralph et al. |
| 6,711,432 B1 | 3/2004 | Krause et al. |
| 6,719,795 B1 | 4/2004 | Cornwall et al. |
| 6,755,839 B2 | 6/2004 | Van Hoeck et al. |
| 7,014,640 B2 | 3/2006 | Kemppanien et al. |
| 7,025,769 B1 | 4/2006 | Ferree |
| 7,077,864 B2 | 7/2006 | Byrd, III et al. |
| D532,515 S | 11/2006 | Buttler et al. |
| D533,664 S | 12/2006 | Buttler et al. |
| 7,207,992 B2 | 4/2007 | Ritland |
| 7,235,076 B2 | 6/2007 | Pacheco |
| 7,288,093 B2 | 10/2007 | Michelson |
| 7,341,590 B2 | 3/2008 | Ferree |
| 7,387,643 B2 | 6/2008 | Michelson |
| 7,406,775 B2 | 8/2008 | Funk et al. |
| 7,454,939 B2 | 11/2008 | Garner et al. |
| 7,491,180 B2 | 2/2009 | Pacheco |
| 7,559,931 B2 | 7/2009 | Stone |
| 7,623,902 B2 | 11/2009 | Pacheco |
| D606,195 S | 12/2009 | Eisen et al. |
| 7,658,610 B2 | 2/2010 | Knopp |
| D618,796 S | 6/2010 | Cantu et al. |
| 7,844,356 B2 | 11/2010 | Matov et al. |
| 7,955,355 B2 | 6/2011 | Cin |
| 7,957,824 B2 | 6/2011 | Boronvinskih et al. |
| 7,957,831 B2 | 6/2011 | Isaacs |
| 7,967,868 B2 | 6/2011 | White et al. |
| 8,057,482 B2 | 11/2011 | Stone et al. |
| 8,070,752 B2 | 12/2011 | Metzger et al. |
| 8,092,465 B2 | 1/2012 | Metzger et al. |
| 8,118,815 B2 | 2/2012 | van der Walt |
| 8,159,753 B2 | 4/2012 | Ojeda et al. |
| 8,167,884 B2 | 5/2012 | Pacheco |
| 8,175,683 B2 | 5/2012 | Roose |
| 8,206,396 B2 | 6/2012 | Trabish |
| 8,214,014 B2 | 7/2012 | Pacheco |
| 8,236,006 B2 | 8/2012 | Hamada |
| 8,241,293 B2 | 8/2012 | Stone |
| 8,257,083 B2 | 9/2012 | Berckmans et al. |
| D669,176 S | 10/2012 | Frey |
| D669,984 S | 10/2012 | Cheney et al. |
| 8,277,461 B2 | 10/2012 | Pacheco |
| 8,282,646 B2 | 10/2012 | Schoenefeld |
| 8,298,235 B2 | 10/2012 | Grinberg |
| 8,298,237 B2 | 10/2012 | Schoenefeld |
| 8,298,242 B2 | 10/2012 | Justis et al. |
| D672,038 S | 12/2012 | Frey |
| 8,357,111 B2 | 1/2013 | Caillouette et al. |
| 8,377,066 B2 | 2/2013 | Katrana et al. |
| 8,407,067 B2 | 3/2013 | Ulthgenannt et al. |
| 8,419,740 B2 | 4/2013 | Aram et al. |
| D685,087 S | 6/2013 | Voic |
| 8,460,303 B2 | 6/2013 | Park |
| 8,480,679 B2 | 7/2013 | Park et al. |
| 8,535,387 B2 | 9/2013 | Meridew et al. |
| 8,540,719 B2 | 9/2013 | Peukert et al. |
| 8,545,509 B2 | 10/2013 | Park et al. |
| 8,549,888 B2 | 10/2013 | Isaacs |
| 8,568,487 B2 | 10/2013 | Witt et al. |
| 8,591,516 B2 | 11/2013 | Metzger et al. |
| 8,603,180 B2 | 12/2013 | White et al. |
| 8,607,603 B2 | 12/2013 | Justis et al. |
| 8,608,748 B2 | 12/2013 | Metzger et al. |
| 8,608,749 B2 | 12/2013 | Witt et al. |
| 8,632,547 B2 | 1/2014 | Metzger et al. |
| 8,668,700 B2 | 3/2014 | Catanzarite |
| D705,929 S | 5/2014 | Frey |
| 8,721,651 B2 | 5/2014 | Loke et al. |
| 8,758,357 B2 | 6/2014 | Frey |
| 8,808,302 B2 | 8/2014 | White et al. |
| 8,808,303 B2 | 8/2014 | Stemniski et al. |
| 8,858,561 B2 | 10/2014 | White et al. |
| 8,864,769 B2 | 10/2014 | Stone et al. |
| 8,870,889 B2 | 10/2014 | Frey |
| D718,862 S | 12/2014 | Matheny |
| D718,863 S | 12/2014 | Matheny |
| D718,864 S | 12/2014 | Matheny |
| 8,979,749 B2 | 3/2015 | Gorek et al. |
| 8,992,538 B2 | 3/2015 | Keefer |
| D726,914 S | 4/2015 | Matheny |
| 9,017,412 B2 | 4/2015 | Wolters et al. |
| 9,044,285 B2 | 6/2015 | Harper |
| 9,066,727 B2 | 6/2015 | Catanzarite et al. |
| 9,066,816 B2 | 6/2015 | Allard et al. |
| 9,113,971 B2 | 8/2015 | Metzger et al. |
| D738,498 S | 9/2015 | Frey et al. |
| 9,138,325 B2 | 9/2015 | Mouw |
| 9,173,661 B2 | 11/2015 | Metzger et al. |
| D745,671 S | 12/2015 | Frey et al. |
| D745,672 S | 12/2015 | Frey et al. |
| D745,673 S | 12/2015 | Frey et al. |
| 9,198,678 B2 | 12/2015 | Frey et al. |
| 9,289,253 B2 | 3/2016 | Sweeney |
| 9,486,324 B2 | 11/2016 | Hochschuler |
| D775,335 S | 12/2016 | Frey et al. |
| 9,642,633 B2 | 5/2017 | Frey et al. |
| 9,649,160 B2 | 5/2017 | van der Walt et al. |

(56) References Cited

U.S. PATENT DOCUMENTS

| | | |
|---|---|---|
| 9,662,157 B2 | 5/2017 | Schneider et al. |
| 9,675,400 B2 | 6/2017 | Katrana et al. |
| 9,737,339 B2 | 8/2017 | Copp et al. |
| 9,814,497 B1 | 11/2017 | Al-Habib et al. |
| 9,826,991 B2 | 11/2017 | Kaiser et al. |
| 9,839,448 B2 | 12/2017 | Reckling et al. |
| 9,848,922 B2 | 12/2017 | Tohmeh et al. |
| 9,913,669 B1 | 3/2018 | Scholl et al. |
| 9,949,843 B2 | 4/2018 | Reiley et al. |
| 9,968,408 B1 | 5/2018 | Casey et al. |
| 9,987,024 B2 | 6/2018 | Frey et al. |
| 10,085,784 B2 | 10/2018 | Ono et al. |
| 10,166,033 B2 | 1/2019 | Keiley et al. |
| 2004/0097925 A1 | 5/2004 | Boehm et al. |
| 2004/0144149 A1 | 7/2004 | Strippgen et al. |
| 2004/0243481 A1 | 12/2004 | Bradbury et al. |
| 2005/0148843 A1 | 7/2005 | Roose |
| 2005/0177156 A1 | 8/2005 | Timm et al. |
| 2005/0262911 A1 | 12/2005 | Dankowicz et al. |
| 2006/0058792 A1 | 3/2006 | Hynes |
| 2006/0084986 A1 | 4/2006 | Grinberg et al. |
| 2006/0095044 A1 | 5/2006 | Grady, Jr. et al. |
| 2006/0149375 A1 | 7/2006 | Yuan et al. |
| 2006/0241385 A1 | 10/2006 | Dietz |
| 2007/0227216 A1 | 10/2007 | Schalliol |
| 2007/0288030 A1 | 12/2007 | Metzger et al. |
| 2008/0086127 A1 | 4/2008 | Patterson et al. |
| 2008/0114370 A1 | 5/2008 | Schoenefeld |
| 2008/0161815 A1 | 7/2008 | Schoenefeld et al. |
| 2008/0183214 A1 | 7/2008 | Copp et al. |
| 2008/0255564 A1 | 10/2008 | Michelson |
| 2008/0257363 A1 | 10/2008 | Schoenefeld et al. |
| 2008/0275452 A1 | 11/2008 | Lang et al. |
| 2008/0306552 A1 | 12/2008 | Winslow |
| 2008/0312659 A1 | 12/2008 | Metzger et al. |
| 2008/0319491 A1 | 12/2008 | Schoenefeld |
| 2009/0076555 A1 | 3/2009 | Lowry et al. |
| 2009/0087276 A1 | 4/2009 | Rose |
| 2009/0088674 A1 | 4/2009 | Caillouette et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0105760 A1 | 4/2009 | Frey |
| 2009/0110498 A1 | 4/2009 | Park |
| 2009/0138020 A1 | 5/2009 | Park et al. |
| 2009/0187194 A1 | 7/2009 | Hamada |
| 2009/0198277 A1 | 8/2009 | Gordon et al. |
| 2009/0254093 A1 | 10/2009 | White et al. |
| 2009/0270868 A1 | 10/2009 | Park et al. |
| 2009/0326537 A1 | 12/2009 | Anderson |
| 2010/0016984 A1 | 1/2010 | Trabish |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0100193 A1 | 4/2010 | White |
| 2010/0152782 A1 | 6/2010 | Stone et al. |
| 2010/0185204 A1 | 7/2010 | Buttermann et al. |
| 2010/0191244 A1 | 7/2010 | White et al. |
| 2010/0217270 A1 | 8/2010 | Polinski et al. |
| 2010/0217336 A1 | 8/2010 | Crawford et al. |
| 2010/0305700 A1 | 12/2010 | Ben-Arye et al. |
| 2010/0324692 A1 | 12/2010 | Uthgenannt et al. |
| 2011/0015636 A1 | 1/2011 | Katrana et al. |
| 2011/0015639 A1 | 1/2011 | Metzger et al. |
| 2011/0046735 A1 | 2/2011 | Metzger et al. |
| 2011/0054478 A1 | 3/2011 | Vanasse et al. |
| 2011/0071533 A1 | 3/2011 | Metzger et al. |
| 2011/0046628 A1 | 4/2011 | Jamali |
| 2011/0093023 A1 | 4/2011 | Lee et al. |
| 2011/0093086 A1 | 4/2011 | Witt et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0213376 A1 | 9/2011 | Maxson et al. |
| 2011/0218545 A1 | 9/2011 | Catanzarite et al. |
| 2011/0224674 A1 | 9/2011 | White et al. |
| 2011/0288433 A1 | 11/2011 | Kelleher et al. |
| 2011/0319745 A1 | 12/2011 | Frey |
| 2012/0041445 A1 | 2/2012 | Roose et al. |
| 2012/0130434 A1 | 5/2012 | Stemniski et al. |
| 2012/0150243 A9 | 6/2012 | Crawford et al. |
| 2012/0179259 A1 | 7/2012 | McDonough et al. |
| 2012/0215315 A1 | 8/2012 | Hochschuler et al. |
| 2012/0245587 A1 | 9/2012 | Fang |
| 2013/0006251 A1 | 1/2013 | Aram et al. |
| 2013/0053854 A1 | 2/2013 | Schoenefeld et al. |
| 2013/0110174 A1 | 5/2013 | Marik |
| 2013/0123850 A1 | 5/2013 | Schoenefeld et al. |
| 2013/0218163 A1 | 8/2013 | Frey |
| 2014/0137618 A1 | 5/2014 | Isaacs |
| 2014/0350614 A1 | 11/2014 | Frey |
| 2014/0379032 A1 | 12/2014 | Hennard |
| 2015/0047410 A1 | 2/2015 | Petit et al. |
| 2015/0127053 A1 | 5/2015 | Maruenda Paulino et al. |
| 2015/0297249 A1 | 10/2015 | Catanzarite |
| 2016/0030067 A1 | 2/2016 | Frey et al. |
| 2016/0270802 A1 | 9/2016 | Fang et al. |
| 2017/0215857 A1 | 8/2017 | D'Urso |

FOREIGN PATENT DOCUMENTS

| | | |
|---|---|---|
| CN | 201275138 | 7/2009 |
| CN | 201404283 | 2/2010 |
| CN | 101390773 | 11/2010 |
| CN | 101953713 | 1/2011 |
| CN | 104306061 | 1/2015 |
| CN | 105078563 | 11/2015 |
| CN | 106175911 | 12/2016 |
| CN | 104224306 | 8/2017 |
| DE | 102013110699 | 4/2015 |
| DE | 202014011170 U1 | 4/2018 |
| EP | 2168507 | 3/2010 |
| EP | 2957244 | 12/2015 |
| EP | 2749235 | 8/2017 |
| EP | 3381382 | 10/2018 |
| FR | 3012030 | 12/2015 |
| FR | 3023655 | 4/2018 |
| GB | 2447702 | 9/2008 |
| JP | 2006-528533 | 12/2006 |
| JP | 2008-514362 | 5/2008 |
| JP | 2012-143379 | 8/2012 |
| JP | D1508406 | 10/2014 |
| WO | WO2001037728 | 8/2002 |
| WO | WO2004071314 | 8/2004 |
| WO | WO2006039266 | 4/2006 |
| WO | WO2007145937 | 12/2007 |
| WO | WO2008027549 | 3/2008 |
| WO | WO2009004625 | 1/2009 |
| WO | WO2009035358 | 3/2009 |
| WO | WO2006017641 | 4/2009 |
| WO | WO2008157412 | 4/2009 |
| WO | WO2009129063 | 10/2009 |
| WO | WO2009105106 | 12/2009 |
| WO | WO2010033431 | 3/2010 |
| WO | WO2010148103 | 12/2010 |
| WO | WO2011041398 | 4/2011 |
| WO | WO2011080260 | 7/2011 |
| WO | WO2011106711 | 9/2011 |
| WO | WO2011109260 | 9/2011 |
| WO | WO2012082164 | 6/2012 |
| WO | WO2012152900 | 11/2012 |
| WO | WO2013041618 | 3/2013 |
| WO | WO2013104682 | 7/2013 |
| WO | WO2013169674 | 11/2013 |
| WO | WO2013173700 | 11/2013 |
| WO | WO2014070889 | 5/2014 |
| WO | WO2014088801 | 6/2014 |
| WO | WO2014090908 | 6/2014 |
| WO | WO2014095853 | 6/2014 |

(56) References Cited

FOREIGN PATENT DOCUMENTS

| WO | WO2014143762 | 9/2014 |
|---|---|---|
| WO | WO2014198279 | 12/2014 |
| WO | WO2016148675 | 9/2016 |

OTHER PUBLICATIONS

Dai et al. "Surgical treatment of the osteoporotic spine with bone cement-injectable cannulated pedicle screw fixation: technical description and preliminary application in 43 patients," Clinics, Feb. 2015, vol. 70, No. 2, pp. 114-119.
Extended Search Report for European Patent Application No. 11804191.2, dated May 7, 2015. 8 pages.
Extended Search Report for European Patent Application No. 13778164.7, dated Feb. 17, 2016. 10 pages.
Hong et al. "Binder-jetting 3D printing and alloy development of new biodegradable Fe—Mn—Ca/Mg alloys," Acta Biomaterialia, Nov. 2016, vol. 45, pp. 375-386 (Abstract only) 4 pages.
International Preliminary Report on Patentability for International (PCT) Patent Application No. PCT/US11/42412 dated Jan. 17, 2013, 7 pages.
International Preliminary Report on Patentability for International Patent Application No. PCT/US2013/036535, dated Oct. 30, 2014, 7 pages.
International Preliminary Report on Patentability for International Patent Application No. PCT/US2014/041379, dated Dec. 17, 2015, 6 pages.
International Preliminary Report on Patentability for International Patent Application No. PCT/US2015/032356, dated Dec. 15, 2016, 7 pages.
International Search Report and Written Opinion for International Patent Application No. PCT/US11/42412 dated Nov. 8, 2011.
International Search Report and Written Opinion for International Patent Application No. PCT/US15/32356, dated Oct. 28, 2015, 10 pages.
International Search Report and Written Opinion for International Patent Application No. PCT/US2013/036535, dated Jun. 26, 2013, 8 pages.
International Search Report and Written Opinion for International Patent Application No. PCT/US2014/041379, dated Oct. 28, 2014, 7 pages.
International Search Report and Written Opinion for International Patent Application No. PCT/US2016/056970, dated Mar. 10, 2017, 13 pages.
Introducing IntelliSense Drill Technology®, McGinley Orthopaedic Innovations, 1 page, [captured Feb. 29, 2016 from: http://web.archive.org/web/20160229042028/http://www.mcginleyorthopaedicinnovations.com/index.php?/pages/drill].
Jakus et al. "Hyperelastic "bone": A highly versatile, growth factor-free, osteoregenerative, scalable, and surgically friendly biomaterial," Science Translational Medicine, Sep. 2016, vol. 8, No. 358, pp. 358ra127 (Abstract only) 5 pages.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).
Lu et al. "A Novel Patient-Specific Navigational Template for Cervical Pedicle Screw Placement," Spine, Dec. 15, 2009, vol. 34, No. 26, pp. E959-E966 (Abstract Only).
Notice of Allowance for U.S. Appl. No. 13/172,683 dated Apr. 23, 2014., 7 pages.
Notice of Allowance for U.S. Appl. No. 13/841,069, dated Sep. 18, 2014. 7 pages.
Notice of Allowance for U.S. Appl. No. 14/298,624, dated Oct. 7, 2015. 7 pages.
Notice of Allowance for U.S. Appl. No. 14/883,299, dated Mar. 20, 2017. 12 pages.
Notice of Allowance for U.S. Appl. No. 29/409,734, dated May 11, 2012. 8 pages.
Notice of Allowance for U.S. Appl. No. 29/427,918, dated Oct. 15, 2012. 9 pages.
Notice of Allowance for U.S. Appl. No. 29/432,668 dated Nov. 27, 2013. 11 pages.
Notice of Allowance for U.S. Appl. No. 29/476,699, dated Oct. 2, 2015. 8 pages.
Notice of Allowance for U.S. Appl. No. 29/476,705, dated Oct. 7, 2015. 8 pages.
Notice of Allowance for U.S. Appl. No. 29/476,709, dated Nov. 6, 2015. 8 pages.
Notice of Allowance for U.S. Appl. No. 29/496,231, dated Jul. 23, 2015. 10 pages.
Notice of Allowance for U.S. Appl. No. 29/538,633, dated Jan. 6, 2016. 10 pages.
Notice of Allowance with English Translation for Japan Patent Application No. 2013-518663, dated Dec. 8, 2015. 4 pages.
Notice off Allowance with English Translation for Japan Patent Application No. 2015-507078, dated Jan. 10, 2017. 4 pages.
Official Action for Australian Patent Application No. 2011276468 dated Apr. 10, 2013, 3 Pages.
Official Action for Canada Patent Application No. 2,802,094, dated Feb. 14, 2017, 4 pages.
Official Action for Canada Patent Application No. 2,914,005, dated Feb. 3, 2017, 3 pages.
Official Action for China Patent Application No. 201180029692.7, dated Oct. 8, 2014 12 pages.
Official Action for European Patent Application No. 11804191.2, dated Feb. 17, 2017, 5 pages.
Official Action for U.S. Appl. No. 13/172,683, dated Feb. 24, 2014, 10 pages.
Official Action for U.S. Appl. No. 13/172,683, dated Sep. 10, 2013 7 pages.
Official Action for U.S. Appl. No. 13/841,069 dated Jul. 8, 2014, 6 pages.
Official Action for U.S. Appl. No. 13/841,069, dated Jul. 31, 2014 9 pages.
Official Action for U.S. Appl. No. 14/298,634, dated Apr. 27, 2015 8 pages.
Official Action for U.S. Appl. No. 14/298,634, dated Jul. 7, 2015 6 pages.
Official Action with English Translation for China Patent Application No. 201380030638.3, dated Feb. 4, 2017. 6 pages.
Official Action with English Translation for China Patent Application No. 201380030638.3, dated May 25, 2016. 11 pages.
Official Action with English Translation for Japan Patent Application No. 2013-518663, dated May 12, 2015. 4 pages.
Official Action with English Translation for Russia Patent Application No. 2014143528/14, dated Jan. 13, 2017. 8 pages.
Owen et al. "Rapid prototype patient-specific drill template for cervical pedicle screw placement." Computer Aided Surgery, Sep. 2007, vol. 12, No. 5, pp. 303-308 (Abstract Only).
Partial Search Report for European Patent Application No. 11804191.2, dated Jan. 20, 2015 6 pages.
Ryken et al. "Image-based drill templates for cervical pedicle screw placement Laboratory investigation," Journal of Neurosurgery, Jan. 2009, vol. 10, No. 1 (Abstract Only).
Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).
Examination Report No. 1 for AU2016338436, dated Sep. 22, 2020. 6 pages.
Examiner Requisition for CA3001898, dated Jan. 7, 2020. 3 pages.
Examination Report for IN20182701734, dated Jun. 23, 2020. 6 pages.
Examination Report for IN201617045149, dated Jun. 12, 2020. 5 pages.
Office Action in BR112018007443-8, dated Jun. 9, 2020. 4 pages.
Translated Office Action from Japanese Patent Application No. 2018-519856, dated Oct. 6, 2020. 3 pages.

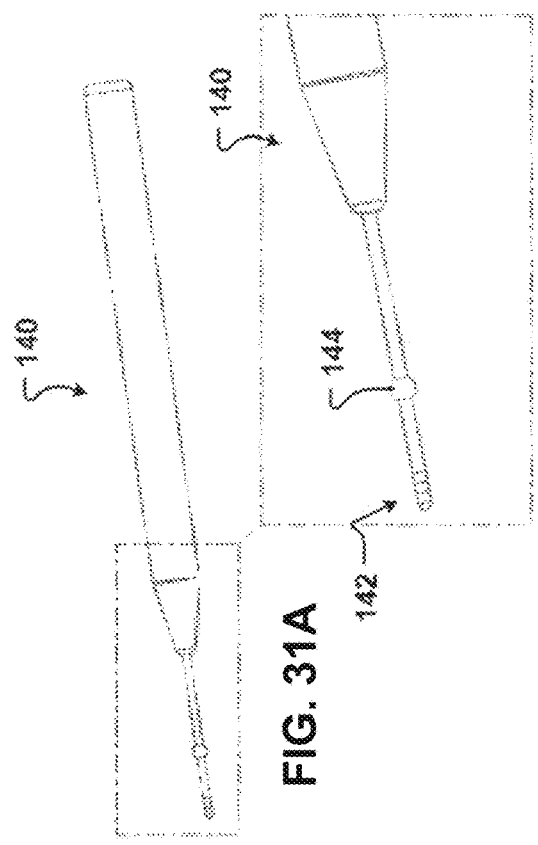
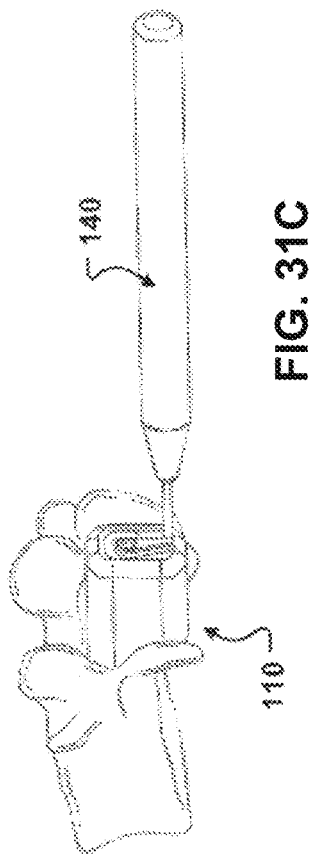
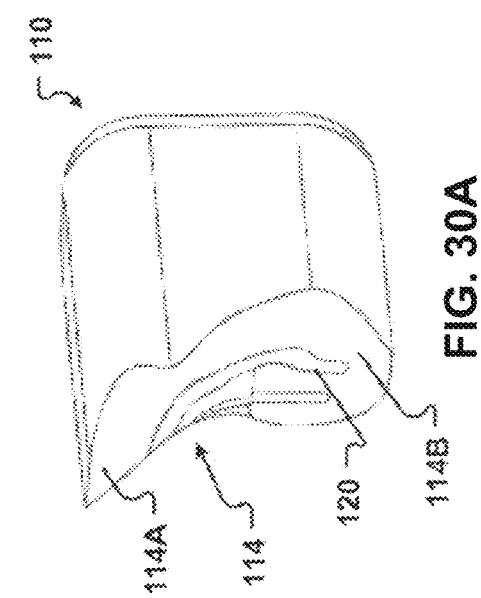
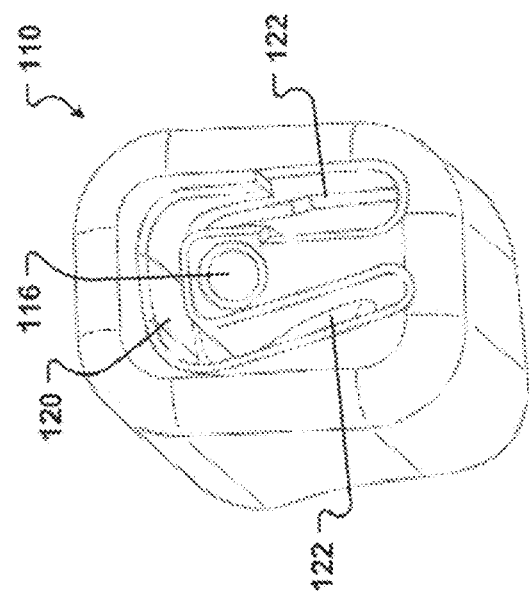

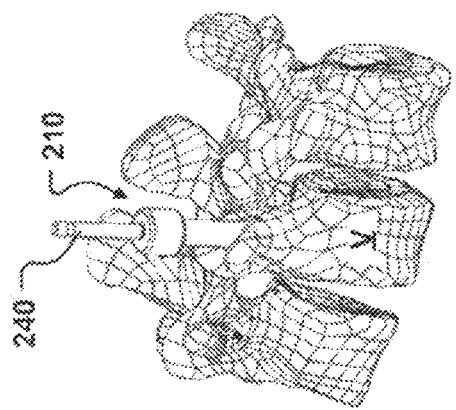
FIG. 33F
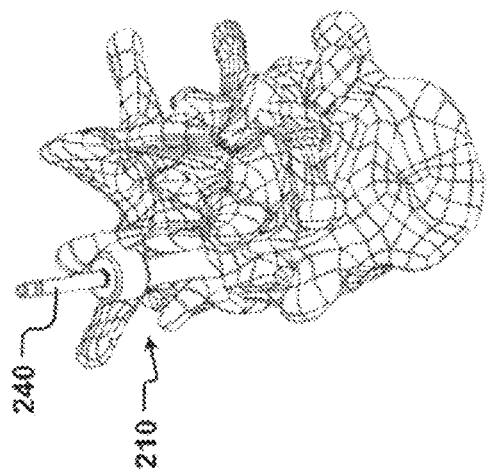
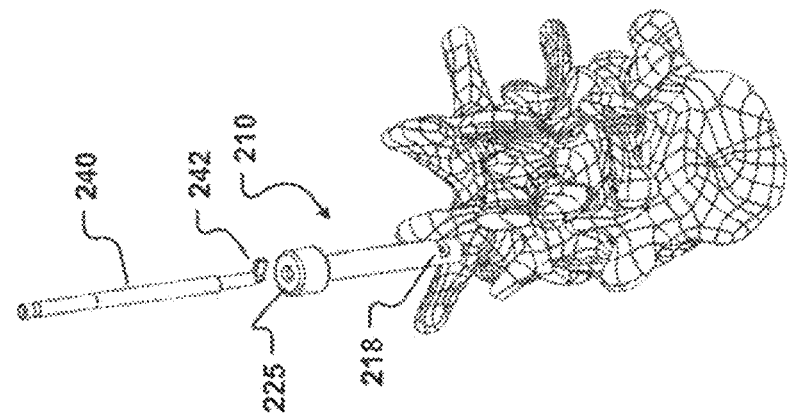
FIG. 33E
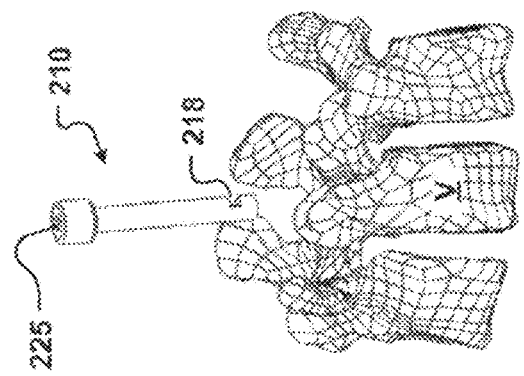
FIG. 33C
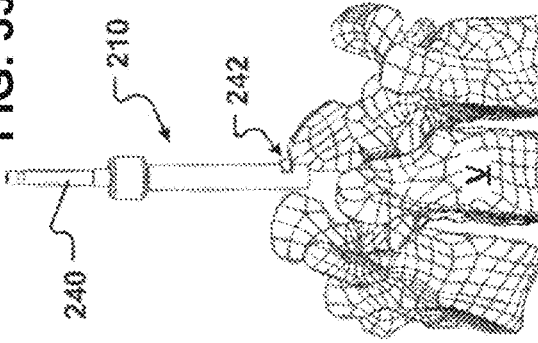
FIG. 33D
FIG. 33G

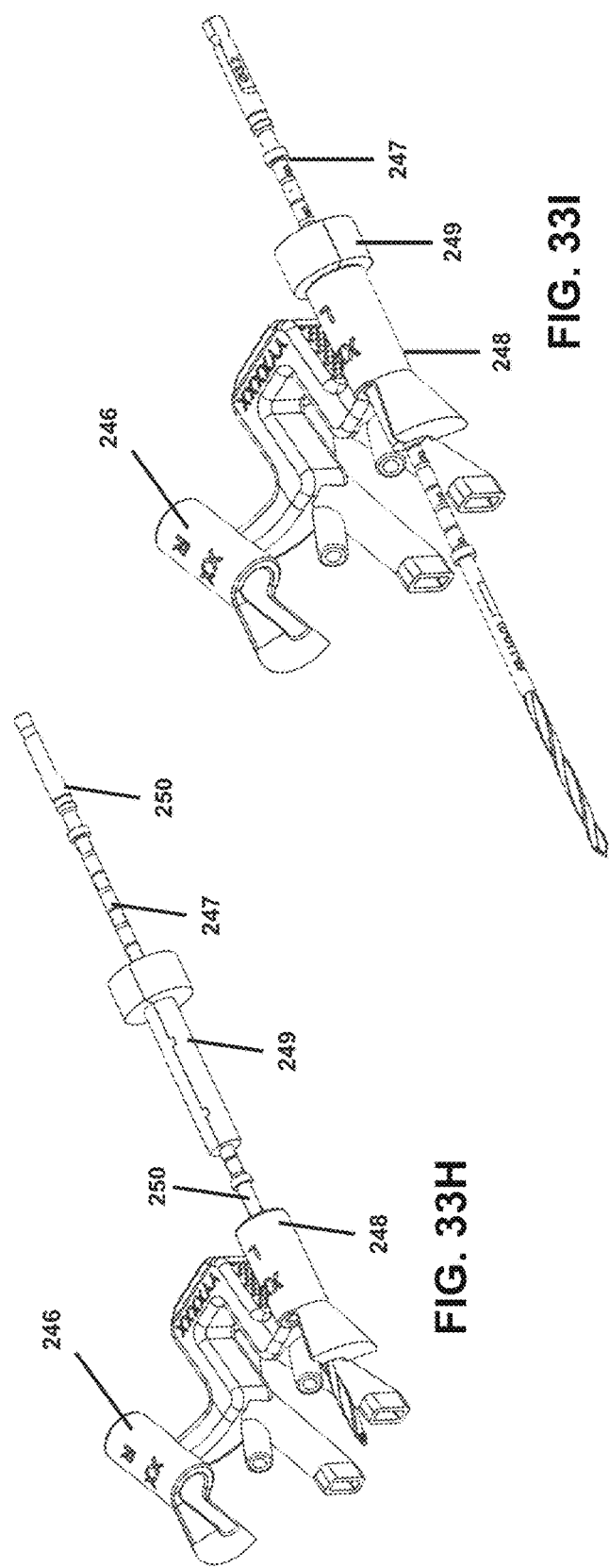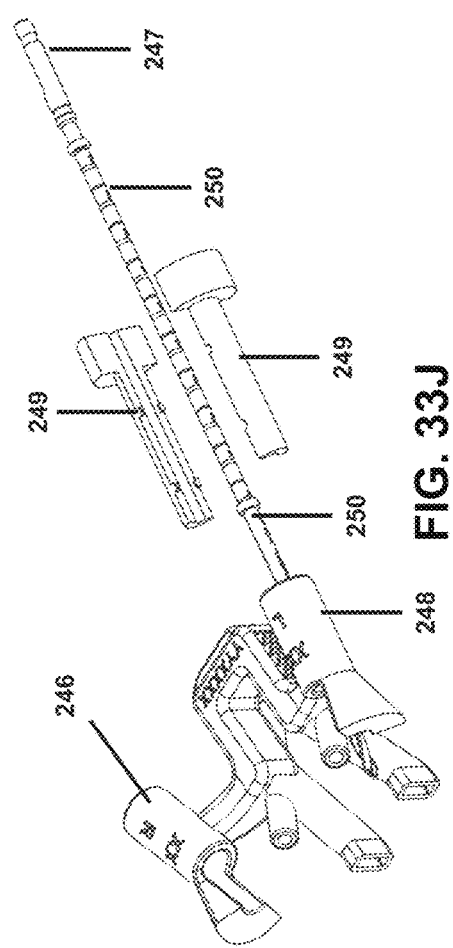

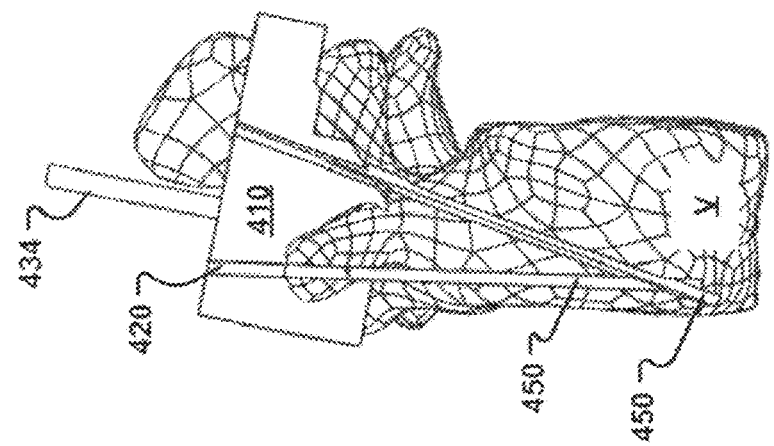
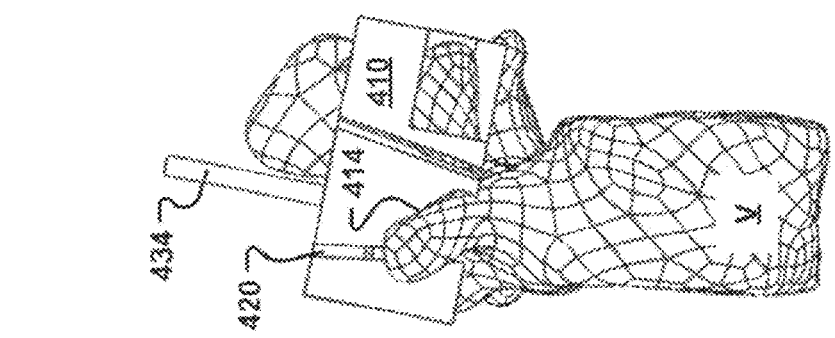
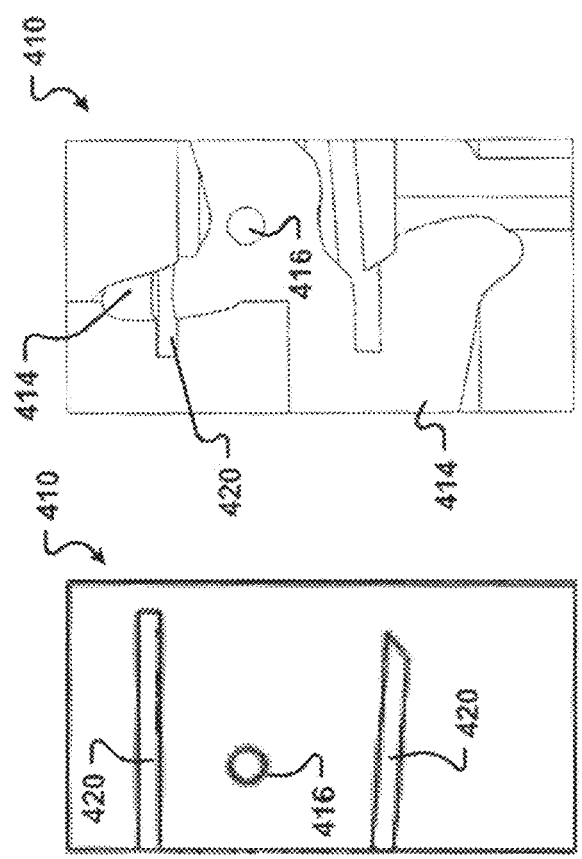
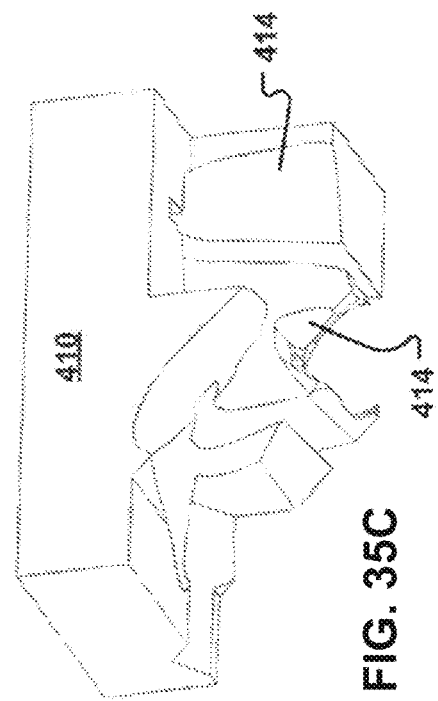

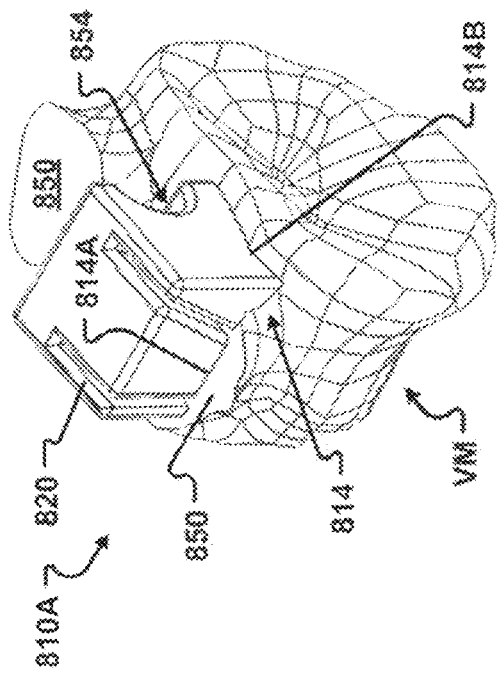
FIG. 39C
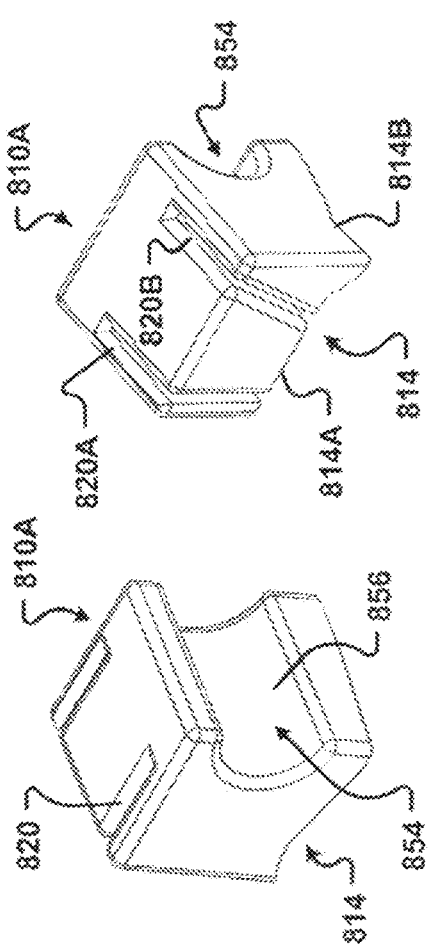
FIG. 39A
FIG. 39B
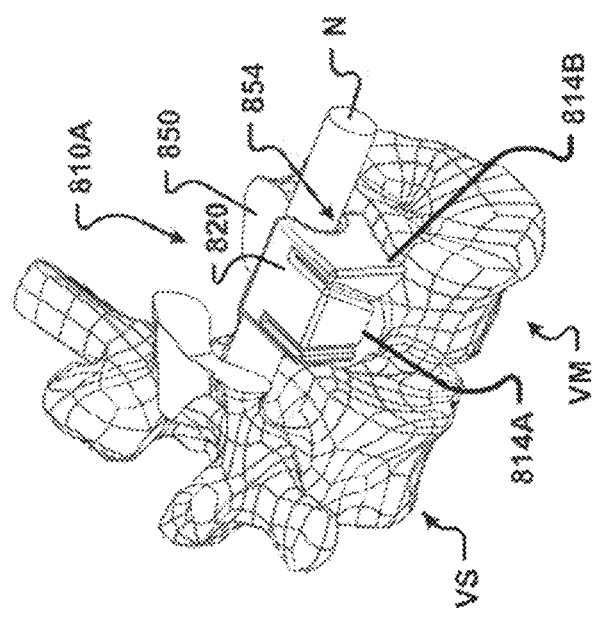
FIG. 39E
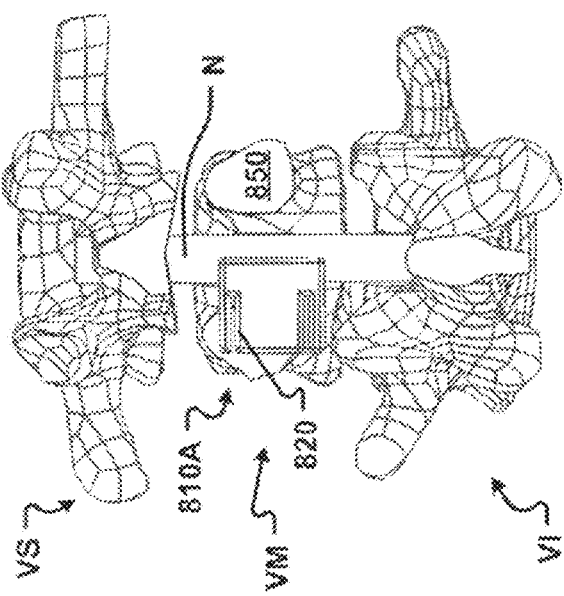
FIG. 39D

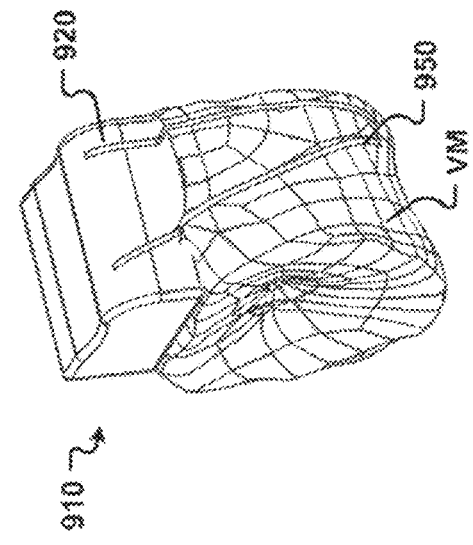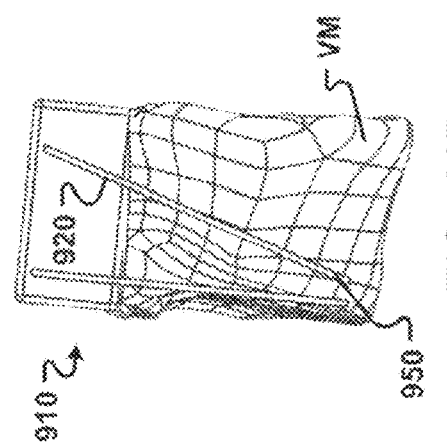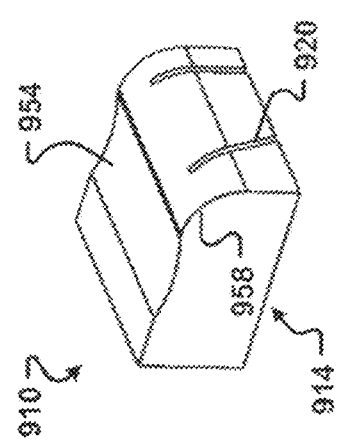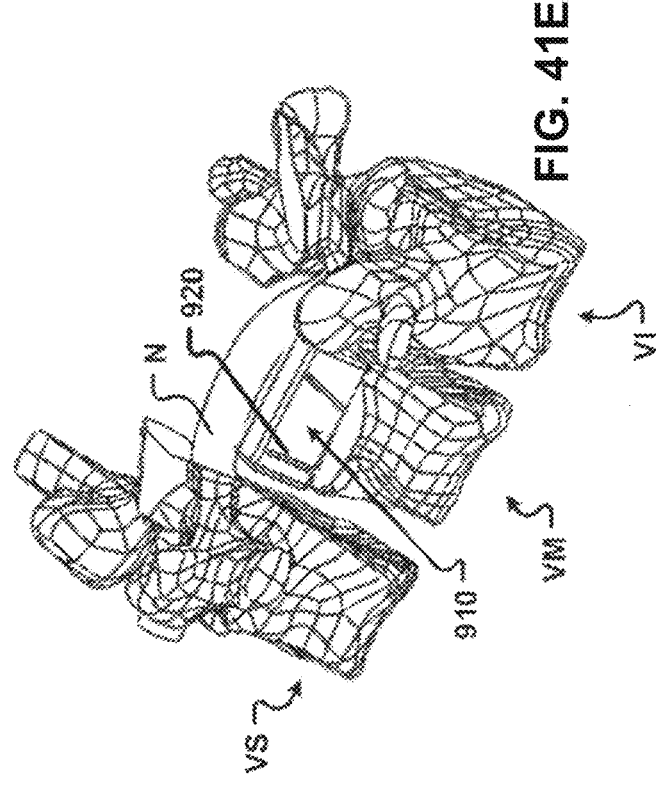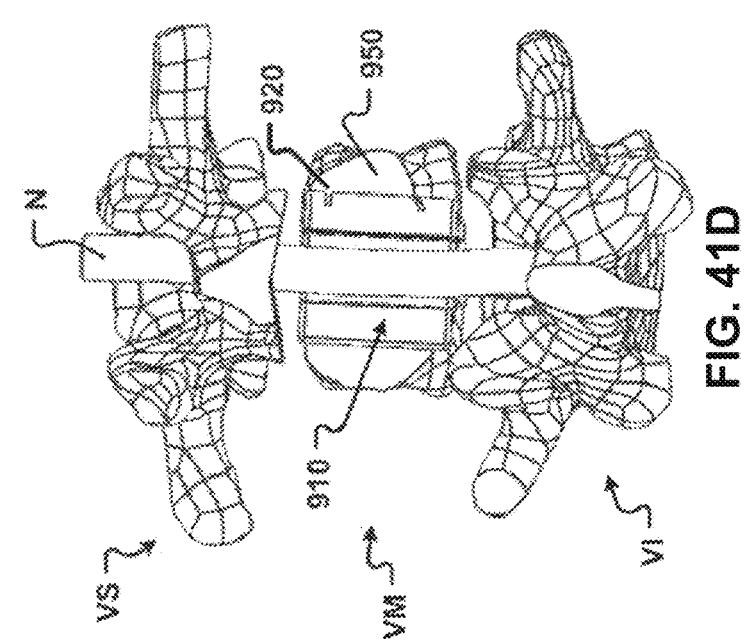
FIG. 41A
FIG. 41B
FIG. 41C
FIG. 41D
FIG. 41E

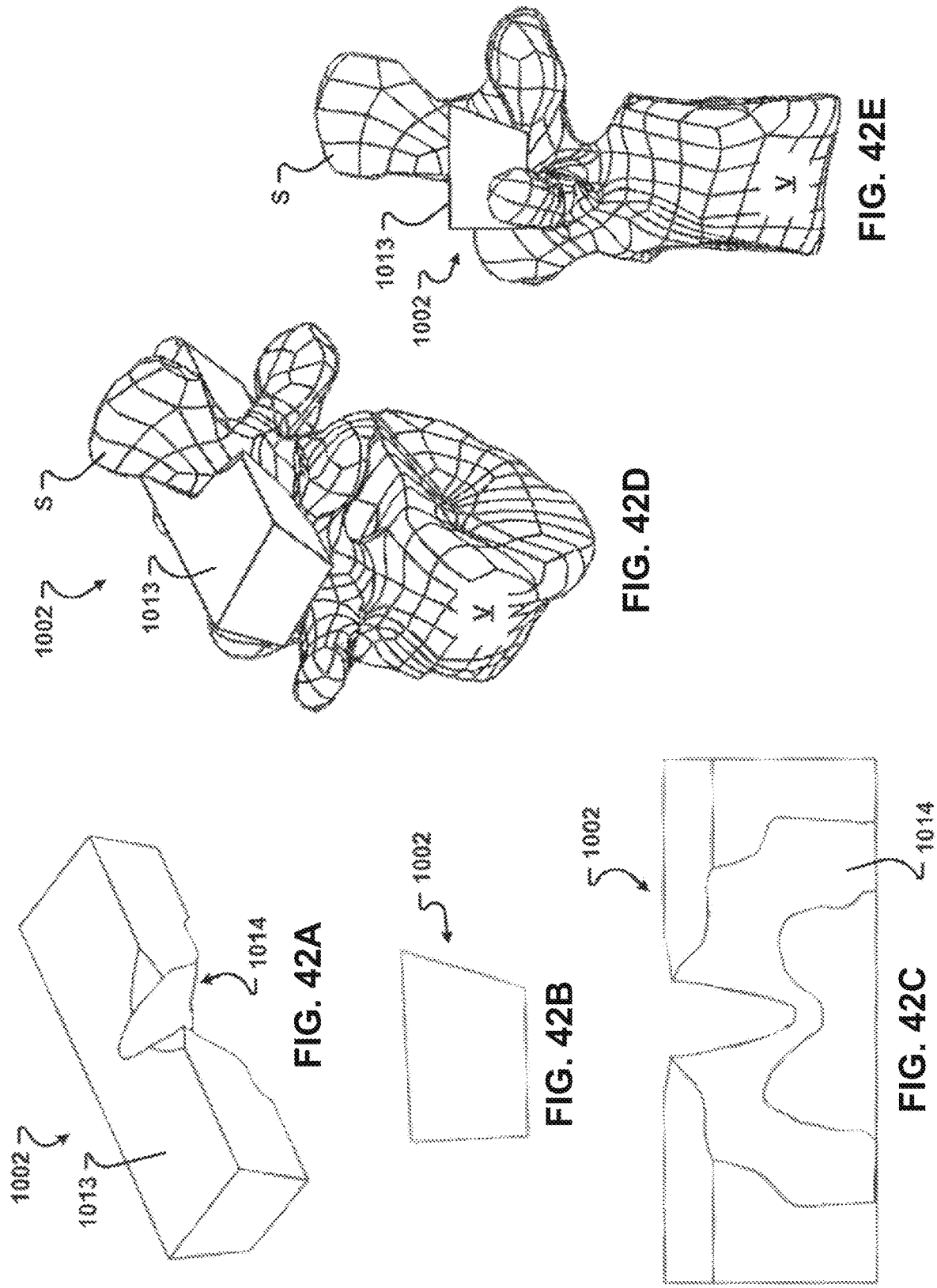

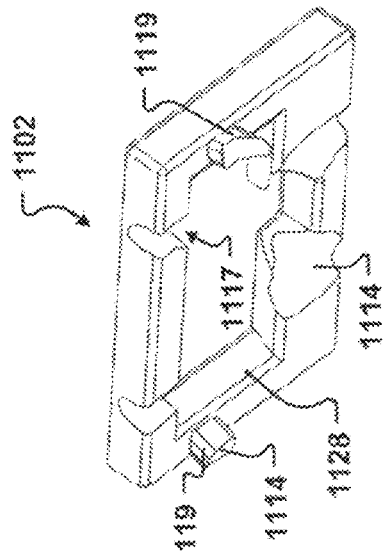
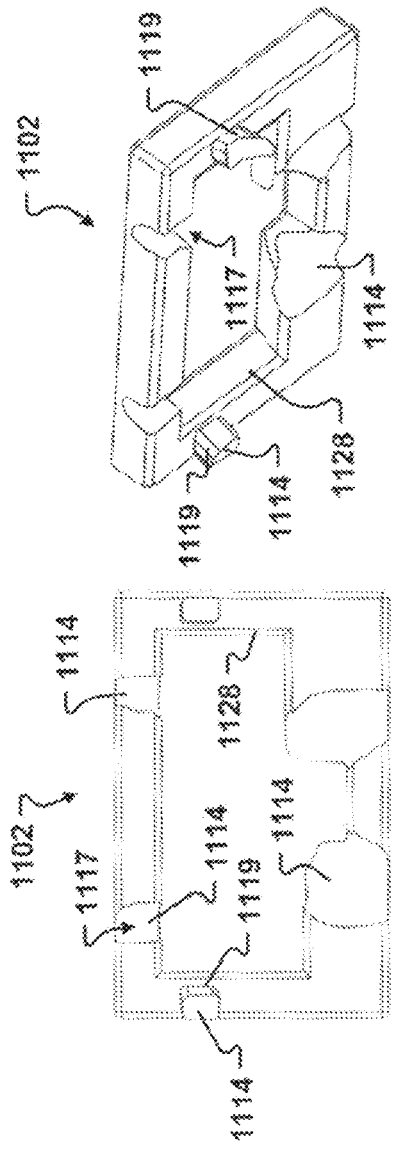
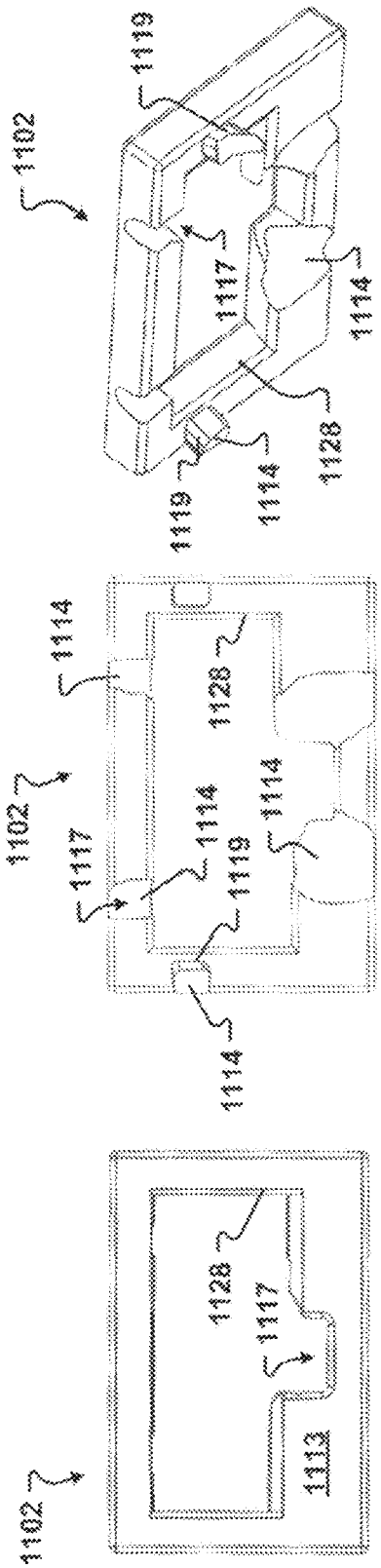
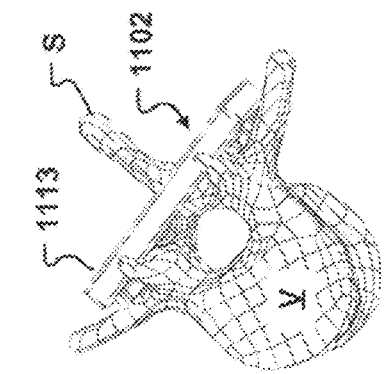
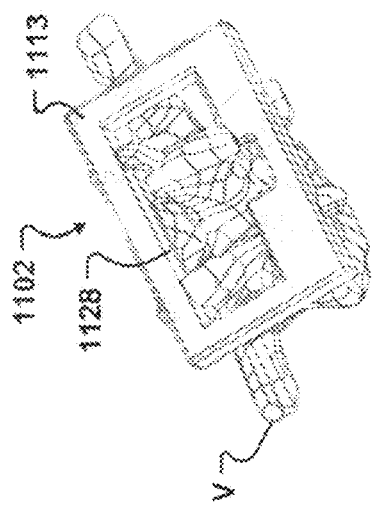
FIG. 43A  FIG. 43B  FIG. 43C  FIG. 43D  FIG. 43E  FIG. 43F

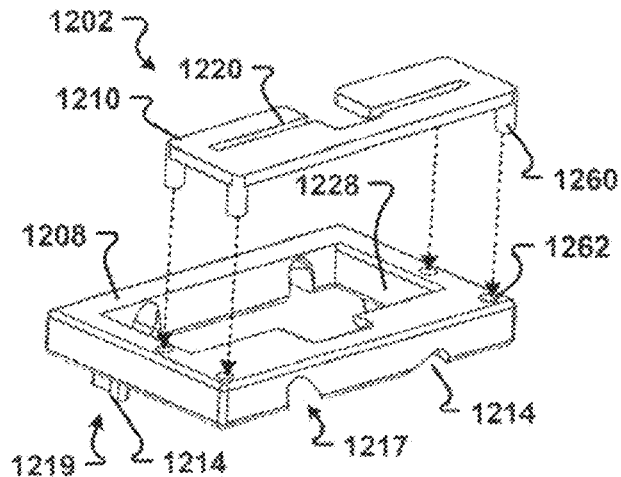
FIG. 45A
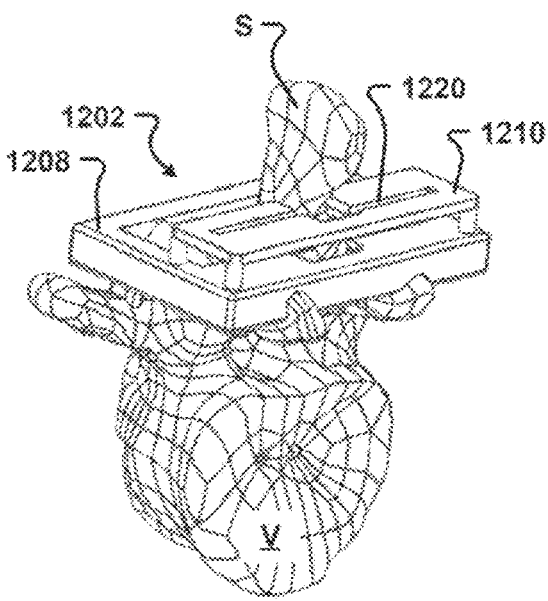
FIG. 45D
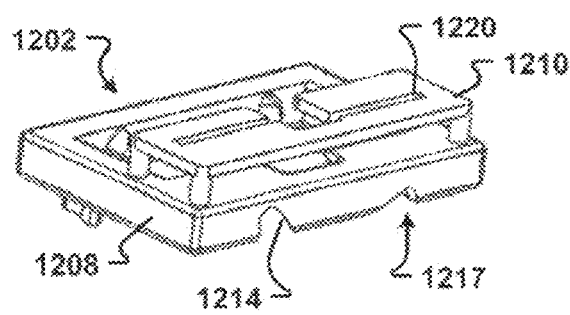
FIG. 45B
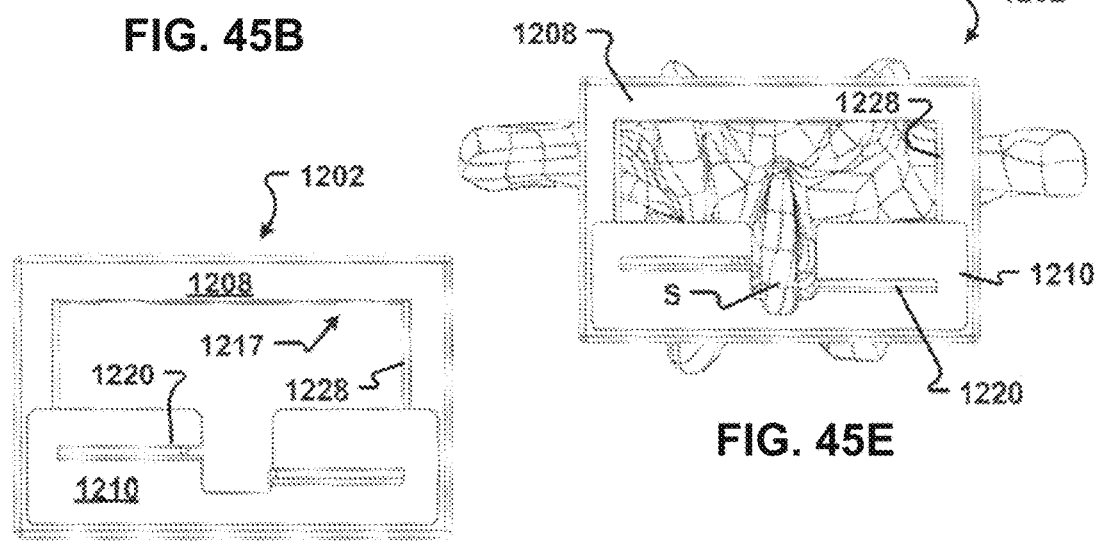
FIG. 45C
FIG. 45E

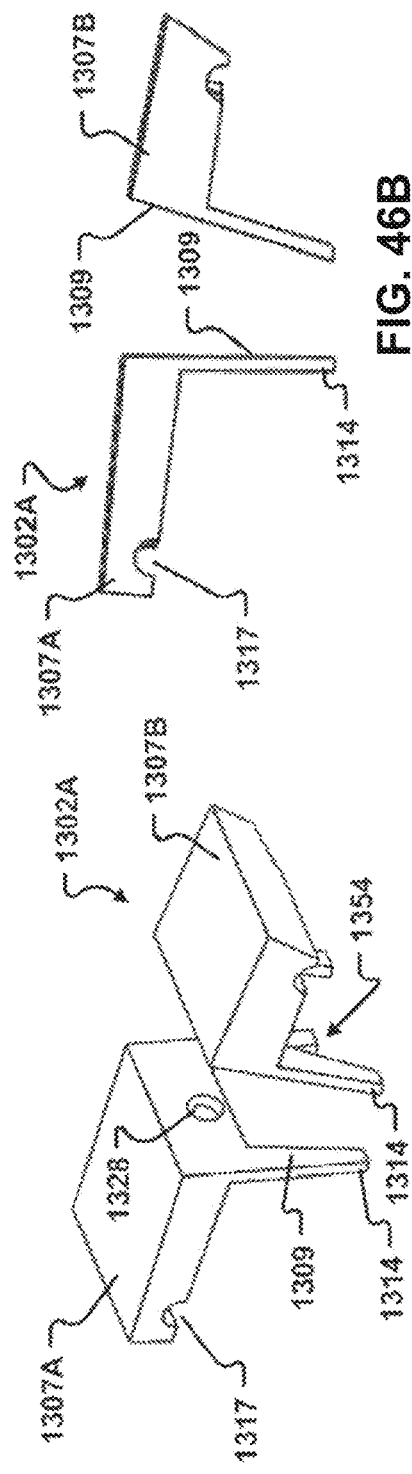
FIG. 46A
FIG. 46B
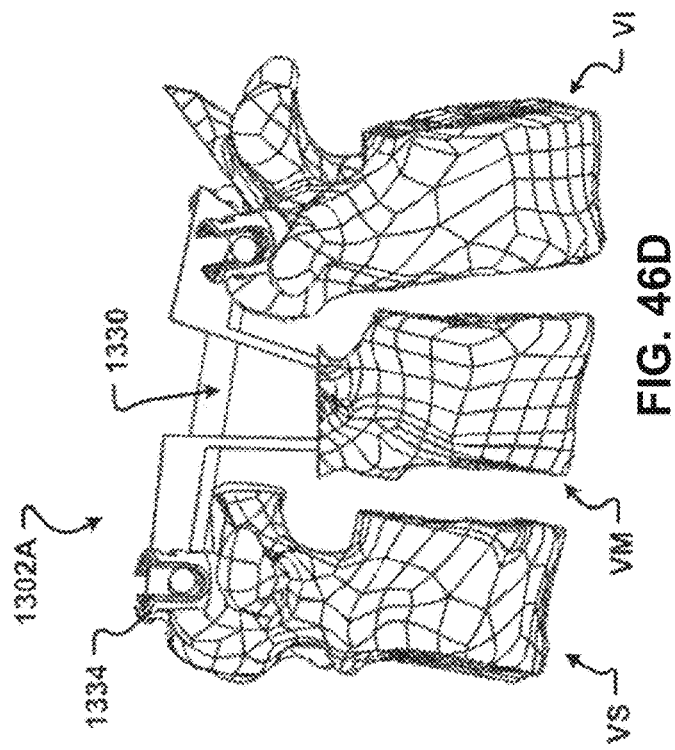
FIG. 46C
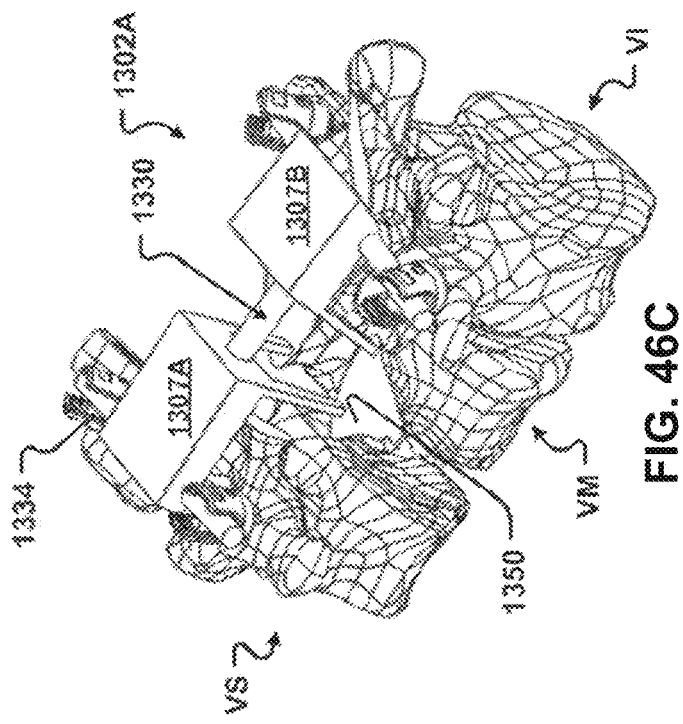
FIG. 46D

PATIENT-MATCHED APPARATUS AND METHODS FOR PERFORMING SURGICAL PROCEDURES

CROSS REFERENCE TO RELATED APPLICATIONS

This application claims the benefit of U.S. Provisional Patent Application Ser. No. 62/743,661, filed Oct. 10, 2019, the entirety of which is incorporated by reference herein. This application is also a continuation-in-part of U.S. patent application Ser. No. 15/997,404, filed Jun. 4, 2018, which is a continuation-in-part of U.S. patent application Ser. No. 15/416,975, filed on Jan. 26, 2017, which issued as U.S. Pat. No. 9,987,024 on Jun. 5, 2018, which in turn is a continuation-in-part of U.S. patent application Ser. No. 14/883,299, filed Oct. 14, 2015, which issued as U.S. Pat. No. 9,642,633 on May 9, 2017, and claims priority under 35 U.S.C. § 119(e) to U.S. Provisional Patent Application 62/373,855, filed Aug. 11, 2016, to U.S. Provisional Patent Application Ser. No. 62/362,440, filed Jul. 14, 2016, and to U.S. Provisional Patent Application Ser. No. 62/287,134, filed Jan. 26, 2016. U.S. patent application Ser. No. 14/883,299 is a continuation-in-part of U.S. patent application Ser. No. 14/298,634, filed Jun. 6, 2014, which issued as U.S. Pat. No. 9,198,678 on Dec. 1, 2015, and claims priority under 35 U.S.C. § 119(e) to U.S. Provisional Application Ser. No. 62/162,466, filed May 15, 2015. U.S. patent application Ser. No. 14/298,634, claims the priority to U.S. Provisional Patent Application Nos. 61/877,837 filed Sep. 13, 2013, 61/845,463 filed Jul. 12, 2013, and 61/832,583 filed Jun. 7, 2013, and is a continuation-in-part of U.S. patent application Ser. No. 13/841,069, filed Mar. 15, 2013, which issued as U.S. Pat. No. 8,870,889 on Oct. 28, 2014 and claims the priority to U.S. Provisional Patent Application Nos. 61/625,559 filed Apr. 17, 2012, 61/393,695 filed Oct. 15, 2010, and 61/359,710 filed Jun. 29, 2010. U.S. patent application Ser. No. 13/841,069 is a continuation in part of U.S. patent application Ser. No. 13/172,683, filed Jun. 29, 2011, which issued as U.S. Pat. No. 8,758,357 on Jun. 24, 2014. U.S. patent application Ser. No. 13/172,683 claims priority to U.S. Provisional Patent Application Nos. 61/393,695 filed Oct. 15, 2010, and 61/359,710, filed Jun. 29, 2010. U.S. patent application Ser. No. 15/997,404 also claims priority under 35 U.S.C. § 119(e) to U.S. Provisional Patent Application Ser. No. 62/628,626 filed Feb. 9, 2018. The entireties of these applications and patents are incorporated by reference herein.

FIELD OF THE INVENTION

The present disclosure relates to the field of medical devices and is generally directed toward apparatus configurable for use with a specific patient in a surgical setting based on the patient's unique anatomical features, and methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan that accounts for the unique and sometimes irregular anatomical features of a particular patient. For example, the implantation of orthopedic screws or other fixation devices in a patient's boney anatomy is well accepted amongst surgeons who treat various orthopedic pathologies. Although the performance of various screw constructs has become predictable, there are still multiple challenges with the placement and insertion of the orthopedic screws or other fixation devices. The challenges occur, for example, when a surgeon is unable to reference boney landmarks due to previous surgery or when the patient's anatomy is irregular in shape, or when a particular trajectory for insertion of the screws (or other fixation devices) is impeded by anatomical obstructions.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a customized surgical guide and/or implant based on the dynamic nature of the anatomical structures the customized guide/implant is designed to associate with. This data, while currently used by surgeons in surgery planning, is largely unused for creating a customized set of instruments or other surgical devices that are designed to complement the patient's unique anatomy.

In addition, virtual reality has provided advantages to surgeons with respect to surgical planning and in particular the ability of surgeons to visual the orientation and placement of orthopedic implants and/or instruments. The surgeon would therefore benefit from the enhanced ability to merge virtual reality capabilities with customized manufacturing and placement of patient-specific guides/implants.

The prior art fails to teach a system for creating a suite of surgical apparatus based on the data set derived from the MRI or CT scan. For example, the use of the patient-specific data set for a vertebral body may allow a surgeon to accommodate for subtle variations in the position and orientation of a plate or other bone anchor to avoid particular boney anatomy or irregularities in the positioning and alignment of the adjoining vertebral bodies. As another example, the use of these data sets may also assist a surgeon in selecting a desired trajectory for an implantable device so as to avoid sensitive anatomical features of a particular patient during an actual procedure. The use of patient-specific data sets further permits the surgeon to avoid mistakes by creating customized tools and instruments, which may comprise orientation, end-stops or other safety related features to avoid over-torque and/or over-insertion of any implantable devices. The use of patient-specific data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide apparatus suitable for use with a surgical procedure and/or patient-specific apparatus that is adapted to conform to a plurality of anatomical features of a particular patient and that otherwise assists a surgeon in completing the surgical procedure(s) safely and efficiently. It is also advantageous to provide a procedure and/or apparatus that otherwise significantly reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel system and method is described for developing customized apparatus for use in one or more surgical procedures, particularly those procedures associated with the occipital bone of the cephalad. The systems and methods described herein incorporate a patient's unique morphology, which may be derived from capturing MRI, CT, or other data to derive one or more "Patient Matched" apparatus, which comprises complementary surfaces based on a plurality of data points from the MRI, CT or other anatomical data. Each "Patient Matched" apparatus is matched and oriented around the patient's own anatomy, and is preferably configured to incorporate specific and/or desired insertional trajectories (which may be verified in a pre-operative setting using 3D CAD software, such as the software disclosed in WO 2008027549, which is incorporated by reference herein in its entirety). According to one embodiment described herein, other apparatus used during the surgical procedure may facilitate the orientation and/or placement of one or more implants, including plates, screws, fixation devices, etc.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207, 992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Various surgical procedures may be performed through introduction of rods or plates, screws or other devices into adjacent boney anatomy to join various portions of, for example, an occipital bone of a particular patient. Surgical procedures are often performed in the spinal and/or cephalad region of a patient. The procedures performed in these areas are often designed to stop and/or eliminate all motion, including by removal and/or destruction of some or all of the boney anatomy in the patient's boney anatomy and/or implantable fixation devices (i.e., plates or screws) for limiting movement of the boney anatomy of the particular patient. By eliminating movement, pain and degenerative disease may be reduced or avoided. Such procedures often require introduction of additional tools to prepare a site for implantation. These tools may include drills, drill guides, debridement tools, irrigation devices, vises, clamps, cannula, and other insertion/retraction tools.

Orthopedic and other surgeries may be performed by a number of different procedures, as opposed to conventional surgical procedures and methods, which typically require cutting of muscles, removal of bone, and retraction of other natural elements. During a MIS procedure, for example, including procedures using the apparatus of the present invention, a less destructive approach to the patient anatomy is carried out by using retractor tubes or portals, which take advantage of anatomy and current technology to limit the damage to intervening structures.

In a typical surgical procedures, skeletal landmarks are established fluoroscopically and a small incision is made over the landmark(s). According to various methods known in the prior art, a series of dilators are applied until one or more cannula is placed over the anatomic structure. In some procedures, a microscope is then placed over the operative site to provide illumination and magnification with a three-dimensional view of the anatomical site to ensure that the surgeon is able to accurately locate the desired patient anatomy and properly position and orient any tool, instrument or other surgical device used during the procedure. The microscope, however, is an expensive and unwieldy device requiring uncomfortable gyrations of the surgeon's back and neck in order to gain the necessary view and is a nuisance to drape (a large, sterile plastic bag has to be placed over the eight-foot-tall structure). The use of adequate illumination is also difficult to direct due to the size of the microscope.

A significant danger of performing operations on a patient's orthopedic anatomy, and in particular accessing an intervertebral space during a MIS surgery on the spine, is that of inadvertently contacting or damaging the para-spinal nerves, including the exiting nerve roots, traversing nerves and the nerves of the cauda equina. The exact location of these para-spinal nerves cannot be precisely determined prior to the commencement of surgery, and therefore are dependent on a surgeon's ability to visually locate the same after the initial incision is made. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannula are received through the patient's back, such as when performing minimally invasive spinal surgery, minor blood vessels are ruptured, thereby blocking the surgeon's vision inside the intervertebral region after the cannula has been inserted. Other anatomical features at a particular patient may also obstruct the surgeon's view or make it difficult to provide illumination within the cannula. Therefore, one particular shortcoming that is addressed by the present disclosure is to provide devices which are patient-matched to facilitate proper location and orientation without use of microscopes or other equipment and that otherwise eliminate the problems associated with prior art procedures on the spine, including MIS procedures.

The customized and integrated matching aspects of this presently disclosed system provides an advantage over the prior art, in particular by providing a plurality of interlocking and/or matching points for each apparatus, which in turn reduces the likelihood of misalignment, misplacement and subsequent mistake during the surgical procedure(s).

Accordingly, one aspect of the present disclosure is to provide a method for preparing a customized surgical device or instrument, which in a preferred embodiment comprises, but is not limited to: (1) obtaining data associated with a patient's anatomy; (2) converting the data obtained to a 3-dimensional data set(s); (3) determining at least one trajectory or path for facilitating a surgical procedure to be performed on the patient; (4) determining at least one surface associated with the patient's anatomy; (5) generating a 3-dimensional representation of the customized surgical device or instrument, which incorporates the at least one trajectory of path and a matching surface to the at least one surface associated with the patient's anatomy; and (6) fabricating the customized surgical device or instrument using the 3-dimensional representation.

According to another aspect of the present disclosure, a system and method for facilitating a surgical procedure(s) comprises, but is not limited to: (1) Obtaining data associated with the patient's anatomy by way of a MRI or CT scan; (2) Converting the MRI or CT scan data to a 3-Dimensional data set(s); (3) Determining one or more axes or planes of orientation of a device to be constructed for use in facilitating the surgical procedure(s) to be performed on the patient; (4) Modeling the device for use in facilitating the surgical procedure(s) using the determined axes and accounting for any other constraints derived from the converted data set(s); (5) Generating a prototype of the modeled device by, for example, use of rapid prototyping machinery; and (6) Preparing the prototype for use during the surgical procedure(s).

According to this aspect described above, the method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure (s), etc.

According to yet another aspect of the present disclosure, the system and method includes use of data obtained from a radiographic imaging machine, a fluoroscopy, an ultrasonic machine or a nuclear medicine scanning device.

In another aspect, the patient-matching features may be confirmed by one or more additional process, such as fluoroscopy or other processes known to those of skill in the art.

In one aspect of the present disclosure, the method comprises the use of bone density data obtained through a CT scan of the patient anatomy for use in planning the trajectory of a surgical guide and corresponding fixation device or instrument, such as a cutting/routing/drilling instrument intended to penetrate the boney anatomy. This data may be used in other manners contemplated and described herein to assist the surgeon in planning, visualizing or otherwise preparing for the surgical procedure for the patient.

In yet another alternative embodiment, the data obtained from one of the scanning devices described above may be supplemented or merged with data from a bone density scanner to fabricate a device that is designed to remain in the patient after the surgical procedure is completed. It is to be expressly understood that data from a bone density scanner is not necessary to practice the inventions described herein, but may supplement the data and assist a surgeon or other medical professional in determining the proper location, trajectory, orientation or alignment of the various apparatus described herein.

According to yet another aspect of the present disclosure, data may be supplemented or merged with data from a bone density scanner to achieve further control over the orientation of any desired axes, particularly where the surgical procedure involves insertion of one or more implantable devices.

According to yet another embodiment, the data obtained from the patient permits the apparatus to be manufactured with defined pathways through the apparatus, which are operatively associated with at least one tool, instrument, or implant, and which permit the at least one tool, instrument or implant to be inserted in the defined pathways in a consistent and reproducible manner. Examples of devices that are implanted or remain in the patient include anchoring devices such as screws, pins, clips, hooks, etc., and implantable devices such as spacers, replacement joints, replacement systems, cages, etc.

In embodiments, the apparatus is a surgical guide that is oriented in at least one trajectory. The trajectory may be one of: (1) a cortical bone trajectory; (2) a pedicle screw trajectory; (3) a cortical trajectory; (4) a sacral pedicle trajectory; (5) a sacral alar trajectory; (6) an S2-alar-iliac trajectory; (7) an iliac trajectory; (8) a transarticular trajectory; (9) a lateral mass trajectory; (10) a translaminar trajectory; (11) a transcondylar trajectory; and (12) an occipital trajectory (for example, during an operation on a patient's cervical/occipital anatomy).

One aspect of the present disclosure is a patient-specific guide designed to fit on the occipital bone of the cephalad. According to this embodiment, the occipital guide is designed to be placed in a mating configuration on the occipital bone to provide location, trajectory, and depth of pilot holes for subsequent alignment/placement of an occipital plate. In certain alternate embodiments, the guide may be used to both align and "carry" the plate. may be removable once the plate is adequately positioned on the patient's boney anatomy.

In one embodiment, the guide is configured as a patient-specific pedicle screw placement guide is for use with a surgical instrument or device. The pedicle screw placement guide is preferably adapted to guide intra-operative placement of pedicle screws that are used to anchor a pedicle screw spinal system onto target portion of a patient's anatomy. In one embodiment, the target portion of the patient's anatomy is a posterior element of the patient's spine. In another embodiment, the pedicle screw placement guide utilizes anatomic landmarks that are identified pre-operatively by a medical imaging scan of the patient. Optionally, the medical imaging scan may include one or more of: an MRI scan, a CT scan, and an x-ray scan. Data obtained from the medical imaging scan may be used to generate a pre-operative plan for the patient. In this manner, the pedicle screw placement guide is configured to be used in a surgical procedure to place a pedicle screw in a pre-operatively determined orientation or trajectory.

In one embodiment, the guide comprises one or more of a polymeric material and a metallic material. In another embodiment, the guide includes at least one patient-matched surface that is substantially congruent to a mating surface of a portion of the patient's anatomy. In one element, the mating surface is the occipital bone of the patient's cephalad.

According to yet another aspect of the present disclosure, a preconfigured surgical template is disclosed, which comprises one or more guides for receiving at least one plate, such as an occipital plate. According to this embodiment, the template further comprise patient-contacting surfaces formed to be substantially congruent with the anatomical features of a patient. The preconfigured surgical template is configured such that the patient-contacting surfaces are configured to contact the plurality of anatomical features in a mating engagement, to ensure proper alignment and mounting of the guide or template, and the guides of the preconfigured surgical template are preferably oriented in a direction selected prior to manufacturing of the preconfigured surgical template to achieve desired positioning, aligning or advancing of a tool within the one or more guides.

According to yet another aspect of the present disclosure, a method for creating a template for use in a surgical operation is disclosed. The method includes, but is not limited to: (1) collecting data from the patient corresponding to the patient's unique anatomy; (2) creating a model of the template from the data collected, the model comprising a plurality of matching surfaces to the patient's unique anatomy; (3) providing data associated with model to fabrication machinery; (4) rapidly generating the template to comprise the plurality of matching surfaces and further comprising at least one additional matching surface corresponding to at least one tool or instrument used in the surgical operation; and (5) generating a permanent device based on the template for use in the surgical operation. In one embodiment of the present disclosure, the model is a digital model. In another embodiment of the present disclosure, the model is a physical model.

According to yet another aspect of the present disclosure, a system for performing a surgical procedure on a patient is disclosed, comprising: (1) a surgical guide, the surgical guide comprising a plurality of surfaces determined from data scanned from the patient, the plurality of surfaces configured to match the patient's boney anatomy; (2) the surgical guide further comprising at least one trajectory or path determined from the patient's boney anatomy for facilitating the surgical procedure; (3) the surgical guide further comprising at least one guide sleeve or aperture; and (4) an instrument comprising at least a first portion adapted to be received within the at least one guide sleeve by inserting the at least a first portion in a first end of the at least one guide sleeve, wherein the at least a first portion of the instrument is adapted to pass through the at least one guide sleeve and exit a second end of the at least one guide sleeve.

Additionally, or alternatively, the guide sleeve and the instrument may comprise a conductive material such that the surgical guide may be subject to an electrical current for providing intra-operative monitoring (IOM) of the instrument during contact with the surgical guide and with the patient anatomy.

It is another aspect of the present disclosure to provide a patient-specific guide for use in a surgical procedure. The guide includes, but is not limited to: (1) a medial body having a proximal portion and a distal portion; (2) at least one cannula comprising a proximal and distal portion and a bore oriented in a direction determined from the anatomical features of a patient, the bore adapted to guide an instrument or a fixation device in a desired trajectory; and (3) a surface of the guide including patient-specific contours determined from the patient's anatomy and configured to contact and substantially conform to at least a first subcutaneous anatomic feature of the patient.

In certain embodiments, the guide further comprises one or more surfaces configured to avoid potentially damaging contact between the surfaces of the guide and surrounding tissue. In one embodiment, the surface in substantially planar and acts a shield to soft tissue on the opposite side of the spinous process as the at least one cannula. In embodiments, the shielding surface of the guide may be removable or adjustable to account for specific tissue the surgeon or health professional preferences.

In one embodiment, the bore of the at least one cannula may have different diameters and/or trajectories between one guide and another. In one embodiment, the bore is directed in a first predetermined trajectory. In another embodiment, the bore(s) are directed in a first and a second predetermined trajectory. In another embodiment, the bore(s) are directed in a plurality of trajectories, each different from the others.

In still another embodiment, the body further comprises a second bore that is oriented in a direction for placement of a fixation device. The guide may further comprise a second surface including patient-specific contours determined from the patient's anatomy and configured to contact and substantially conform to a second anatomic feature of the patient. Additionally, the medial body may optionally include at least one extension from the medial body, the at least extension including a second surface including patient-specific contours determined from the patient's anatomy and configured to contact and substantially conform to a second anatomic feature of the patient.

In one embodiment, the surface with the patient-specific contours is adapted to hook at least partially around a specific portion of the patient's anatomy. In another embodiment, at least a portion of the guide is shaped to prevent contact with a portion of the patient's anatomy.

In still another embodiment, the medial body of the guide comprises a first portion releasably interconnected to a second portion. Optionally, the body may comprise at least two portions. In one embodiment, the portions of the body are adapted to be interconnected together.

In one embodiment, at least a portion of one of the extensions is adapted to hook at least partially around, and substantially conform to, a second anatomic feature of the patient. In one embodiment, at least one of the extensions is adapted to contact a portion of the patient's anatomy that has been altered by a surgical procedure. In another embodiment, at least one of the extensions is adapted to contact an unaltered portion of the patient's anatomy.

In still another embodiment, the guide includes a second bore. The second bore may be oriented in a trajectory that is not parallel to the other bore. In one embodiment, the bore is adapted to guide an instrument. In another embodiment, the bore is oriented in a direction for placement of a temporary fixation device, including a pin or Jamshidi needle, for example.

In one embodiment, a tertiary cannula is associated with the body. The cannula includes a bore that is oriented in a direction for placement of a temporary fixation device. Optionally, the body may further comprise a second bore.

The surgical device may be used in one or more of a minimally invasive surgical procedure and a minimal access procedure. In one embodiment, the surgical device is configured for use in conjunction with a device that employs automated or semi-automated manipulation such that placement of the surgical device with respect to the anatomical feature may be performed remotely by an operator through a computer controller. In another embodiment, the surgical device is identifiable by optical, electronic, or radiological recognition means such that the location and orientation of the surgical device with respect to the anatomical feature is verifiable. In still another embodiment, the surgical device is configured for use in conjunction with a navigation device such that placement of the surgical device with respect to the anatomical feature assists with one or more of registration, stability, and motion tracking by the navigation device.

In embodiments, the surgical devices described herein may be used with a virtual reality or other simulation device. In one embodiment, the virtual reality capabilities are provided in conjunction with a physical guide, while in other embodiments the capabilities are provided in conjunction with a virtual guide.

In one embodiment, the surgical guide also includes one or more of a third contact surface and a fourth contact surfaces configured to be positioned on third and fourth portions of an anatomical feature. The second and third contact surfaces may each be adapted to anatomically mate with at least one independent contour of an anatomical feature.

It is still another aspect of the present disclosure to provide a surgical device that utilizes anatomic landmarks of a patient. The surgical device includes, but is not limited to: (1) a body with a proximal portion and a distal portion; (2) a first contact element with a patient-matched surface that is substantially congruent to a first surface of an anatomical feature of the patient, the first contact element configured to be positioned at least partially within a first incision; and (3) a first cannula with a first bore having a first trajectory that intersects a portion of the anatomical feature, the first bore configured to guide an instrument advanced through a second incision when the patient-matched surface of the first contact element is positioned on the first surface. Optionally, the first cannula may be releasably interconnectable to the surgical device. In one embodiment, the first contact element is determined from and complementary to the patient's anatomy.

In one embodiment, when the first contact element is positioned on the first surface, the first cannula is configured to be positioned one of: (i) within the first incision; and (ii) substantially outside of the first incision. In another embodiment, the first trajectory is oriented along one of: (1) a cortical bone trajectory; (2) a pedicle screw trajectory; (3) a cortical trajectory; (4) a sacral pedicle trajectory; (5) a sacral alar trajectory; (6) an S2-alar-iliac trajectory; and (7) an iliac trajectory. In still another embodiment, the instrument comprises one or more of a k-wire, an instrument sleeve, an insert, a drill, a Jamshidi needle, and a patient-specific fixation device.

In one aspect, the patient-specific guide relates to a cutting guide, comprising: a body having a proximal portion and a distal portion; at least one patient-specific track formed in the body and oriented in a path determined from the anatomical data of the patient, the at least one patient-specific track extending from the proximal portion to the distal portion of the body of the guide; the distal portion of the body comprising at least a first patient specific contour on one side of the at least one patient specific track and a second patient-specific contour on the opposite side of the at least one patient specific track for mating with a patient's boney anatomy; wherein the at least a first and second patient-specific contours are determined from the anatomical data of the patient and are shaped to substantially conform to a specific portion of the patient's boney anatomy.

Incorporated by reference in their entireties are the following U.S. patents and patent applications and international publications directed generally to methods and apparatus related to surgical procedures, thus providing written description support for various aspects of the present disclosure. The U.S. patents and applications incorporated by reference are as follows: U.S. Pat. Nos. 9,295,497, 8,758,357, 8,419,740, 8,357,111, 8,298,237, 8,277,461, 8,257,083, 8,214,014, 8,206,396, 8,167,884, 8,159,753, 7,957,824, 7,844,356, 7,658,610, 7,623,902, 7,491,180, 7,235,076, 6,755,839, 6,711,432, 5,201,734, and 3,151,392, U.S. Design Pat. Nos. D705,929, D669,176, D672,038, D618,796, D606,195, D533,664, D532,515, D428,989, D420,132, D412,032, D403,066, and D359,557, and U.S. Pat. Pub. Nos. 2013/0123850, 2013/0053854, 2013/0218163, 2012/0215315, 2012/0179259, 2012/0130434, 2012/0041445, 2011/0319745, 2011/0288433, 2011/0224674, 2011/0218545, 2011/0213376, 2011/0190899, 2011/0184526, 2011/0184419, 2011/0166578, 2011/0160867, 2011/0160736, 2011/0093086, 2011/0093023, 2011/0071533, 2011/0054478, 2011/0046735, 2011/0015639, 2011/0015636, 2010/0324692, 2010/0305700, 2010/0217336, 2010/0217270, 2010/0191244, 2010/0152782, 2010/0100193, 2010/0087829, 2010/0082035, 2010/0049195, 2010/0016984, 2009/0270868, 2009/0254093, 2009/0198277, 2009/0187194, 2009/0138020, 2009/0110498, 2009/0099567, 2009/0093816, 2009/0088763, 2009/0088761, 2009/0088674, 2009/0087276, 2008/0319491, 2008/0312659, 2008/0275452, 2008/0257363, 2008/0183214, 2008/0161815, 2008/0114370, 2007/0288030, 2006/039266, 2006/0241385, 2006/0149375, 2006/0095044, 2006/0084986, 2005/0148843, 2004/0243481, and 2004/0097925. The international publications incorporated by reference are as follows: European Publication No. EP 2168507, and World Intellectual Property Organization Pub. Nos. WO 2013/104682, WO 2013/041618, WO 2012/152900, WO 2011/109260, WO 2011/106711, WO 2011/080260, WO 2011/041398, WO 2010/148103, WO 2010/033431, WO 2009/129063, WO 2008/027549, and WO 2007/145937, and Chinese Publication Nos. CN 201275138, CN 201404283, CN 101390773, and CN 101953713.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery. The embodiments also reduce the cumulative radiation exposure to both the surgeon and medical professionals in the operating environment and the patient.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation. Embodiments of the present disclosure may be designed such that the apparatus may be formed and verified, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. It is expressly understood for purposes of this disclosure that other types of machinery other than rapid prototyping machinery may be employed in the systems and methods described herein, for example, by computerized numerical control (CNC) machinery.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures. It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein. In the drawings:

FIGS. 30A-30B are perspective views of a cutting guide according to yet another alternative embodiment of the present disclosure;

FIGS. 31A-31B are perspective views of a cutting tool according to yet another alternative embodiment of the present disclosure;

FIG. 31C is another perspective view according to the embodiment shown in FIG. 31A depicted with the cutting guide of FIG. 30A;

FIG. 33C is a side view of a guide sleeve of an embodiment of the present disclosure positioned proximate to the vertebral body illustrated in FIG. 33A;

FIG. 33D is side view of a cutting tool of an embodiment of the present disclosure inserted into a cannula of the guide sleeve of FIG. 33C;

FIG. 33E is a perspective view of the cutting tool and the guide sleeve of FIG. 33D;

FIGS. 33F-33G are additional perspective views of the cutting tool and the guide sleeve of FIG. 33D;

FIGS. 33H-33J are additional perspective views illustrating a boring instrument of an embodiment of the present disclosure wherein the drilling insert or sleeve is attached to the boring instrument.

FIG. 35A is a front elevation view of another guide of the present disclosure;

FIG. 35B is a rear elevation view of the guide of FIG. 35A;

FIG. 35C is a bottom perspective view of the guide of FIG. 35A;

FIG. 35F is a side elevation view of the guide of FIG. 35A positioned against the vertebral body;

FIG. 35G is another side elevation view of the guide of FIG. 35A positioned against the vertebral body and illustrating cuts formed in the vertebral body;

FIGS. 39A-39C are perspective views of still another guide of an embodiment of the present disclosure with FIG. 39C illustrating the guide of FIG. 39A positioned against a vertebral body that has been altered in a surgical procedure;

FIGS. 39D-39E are a front elevation view and a perspective view of the guide of FIG. 39A positioned against a portion of the patient's spine that has been altered in a surgical procedure and further illustrating the guide in relation to a neural element of the patient;

FIG. 41A is a perspective view of yet another guide of the present disclosure;

FIGS. 41B-41C are a side view and a perspective view of the guide of FIG. 41A positioned in contact with a vertebral body that includes cuts formed using the guide;

FIG. 41D is a front elevation view of the guide of FIG. 41A illustrated in a position of use against a portion of a patient's spine and illustrating a neural element of the patient positioned proximate to a recess of the guide;

FIG. 41E is a side perspective view of the guide of FIG. 41D in a similar position of use;

FIG. 42A is a perspective view of a model of an embodiment of the present disclosure;

FIG. 42B is a side elevation view of the model of FIG. 42A;

FIG. 42C is rear elevation view of the model of FIG. 42A;

FIGS. 42D-42E are a perspective view and a side elevation view of the model of FIG. 42A positioned in contact with a vertebral body;

FIG. 43A is a front elevation view of another model of an embodiment of the present disclosure;

FIG. 43B is a rear elevation view of the model of FIG. 43A;

FIG. 43C is a rear perspective view of the model of FIG. 43A;

FIG. 43D is another front elevation view of the model of FIG. 43A in a position of use against a vertebral body;

FIG. 43E is a front perspective view of the model of FIG. 43D;

FIG. 43F is a top perspective view of the model of FIG. 43D;

FIG. 45A is a perspective view of yet another guide of an embodiment of the present disclosure adapted to interconnect to a model of an embodiment of the present disclosure and showing the guide and the model in a disassembled state;

FIG. 45B is a perspective view of the model and the guide of FIG. 45A in an assembled state;

FIG. 45C is a front elevation view of the model and the guide of FIG. 45B;

FIGS. 45D-45E are a perspective view and a front elevation view of the model and the guide of FIG. 45B positioned proximate to a vertebral body;

FIGS. 46A-46B are a perspective view and a side elevation view of still another embodiment of a model of the present disclosure;

FIGS. 46C-46D are a perspective view and a side elevation view of the model of FIG. 46A interconnected to a frame of the present disclosure similar to the frame of FIG. 47A, illustrating the model in a position of use proximate to a portion of the patient's spine;

DETAILED DESCRIPTION

Figure 1:
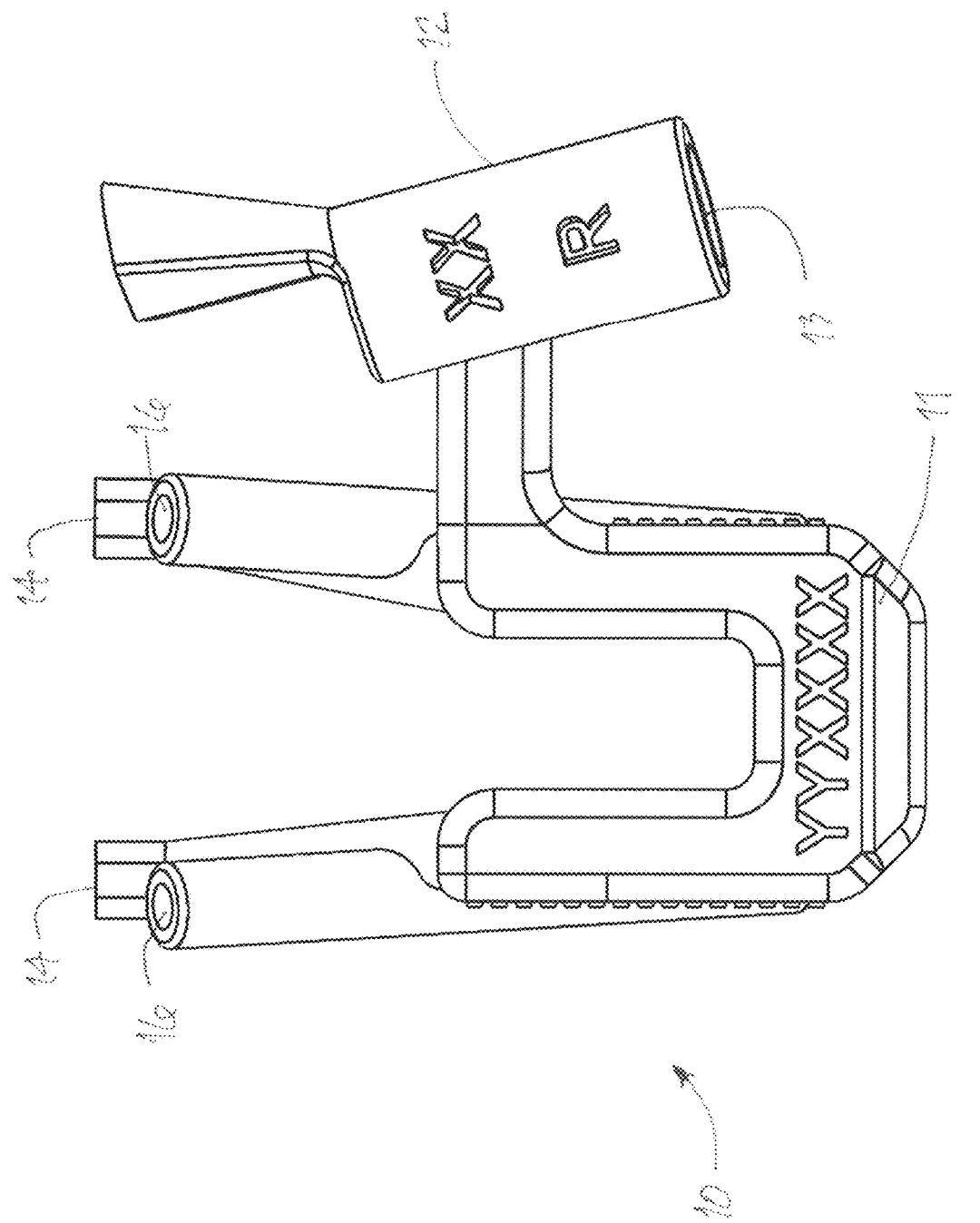
FIG. 1 is a plan view of a patient-specific guide according to embodiments of the present disclosure.

As shown in FIGS. 1-47 and described in further detail herein, the present disclosure relates to a novel system and method for developing a customized, patient-matched apparatus for use in a diverse number of surgical procedures. The system and method preferably uses a patient's unique morphology, which may be derived from capturing MRI data, CT data, or any other medical imaging device to derive one or more patient-matched apparatus, which comprise complementary surfaces to those encountered during the surgical procedure(s) as derived from a set of data points. According to various embodiments described herein, the patient-matched apparatus may further comprise desired axes and/or insertional trajectories. According to one alternate embodiment described herein, the patient-matched apparatus may be further matched with at least other apparatus used during the surgical procedure. Other features of the disclosure will become apparent after a review of the following disclosures and varying embodiments of the disclosure.

Multiple embodiments of a guide according to certain aspects of the certain disclosure are depicted in FIGS. 1-29. In embodiments, and referring to FIG. 1 in particular, a surgical guide 10 is provided and adapted to fit directly to aspects of a patient's anatomy. More specifically, the guide may be positioned proximate to a medial vertebra, including between a superior and inferior vertebrae. Thus, the guide 10 may also comprises at least one lower patient-contacting surface 14 which permits the guide 10 to mate with one or more vertebral bodies. The patient specific surface 14 can be specific to any portion of the patient's anatomy, such as lamina, transverse processes, articular processes, spinous processes, etc. Alternatively, the guide 10 can be interconnected to a frame or other surgical apparatus (by way of example, a tulip, as described in relation to FIGS. 22-29). Surface 14 may be adapted to at least partially hook around a portion of the patient's anatomy. For example, the surface 14 may comprise multiple portions that are adapted to contact two different planes formed by two distinct portions of the patient's anatomy. In this manner, the surface 14 provides a reference to align the guide 10 with a predetermined portion of the patient's anatomy.

A single guide 10 may target one portion of the lamina. Alternatively, the guide may be sized to facilitate a procedure targeting more than one portion of the patient's anatomy, including, for example, both sides of the lamina substantially simultaneously. In other embodiments the guide may contact the iliac or sacrum or other boney anatomical features associated with a specific patient. Multiple guides may be connected together. Alternatively, a particular guide may be comprised of multiple parts that are selectively interconnectable to form the single guide, and thereby permit use of the guide in a minimally invasive surgical procedure.

In embodiments, a patient-specific guide is fabricated using the methods described herein for use in a specific surgical procedure on a particular patient. The guide may include, but is not limited to: (1) a medial body having a proximal portion and a distal portion; (2) at least one cannula comprising a proximal and distal portion and a bore oriented in a direction determined from the anatomical features of a patient, the bore adapted to guide an instrument or a fixation device in a desired trajectory; and (3) a surface of one or more of the medial body and the at least one cannula including patient-specific contours determined from the patient's anatomy and configured to contact and substantially conform to at least a first subcutaneous anatomic feature of a vertebra of the patient.

Still referring to FIG. 1, a patient-specific screw guide is shown comprising a single cannula. This guide may be particularly beneficial for use with a patient where surgical access or other constraints (including body wall proximity) limits the ability to utilize a double cannulae guide. The cannula may be positioned on either side of the guide and may be offset to accommodate surrounding tissue or other areas of concern. Variations on this embodiment are depicted in FIGS. 3-11.

Figure 2A:
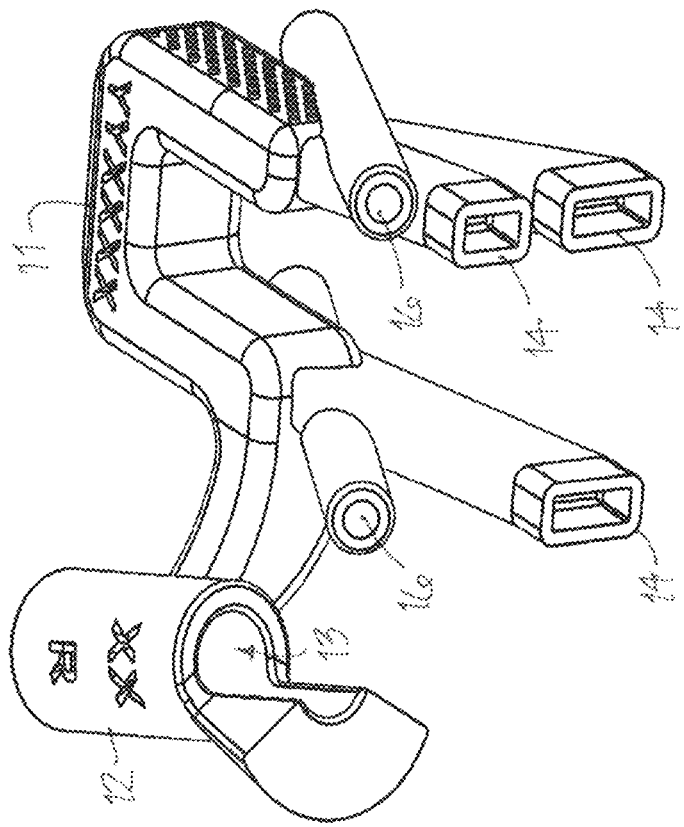
FIGS. 2A-2B are perspective views of patient-specific guides according to other embodiments of the present disclosure.
Figure 2B:
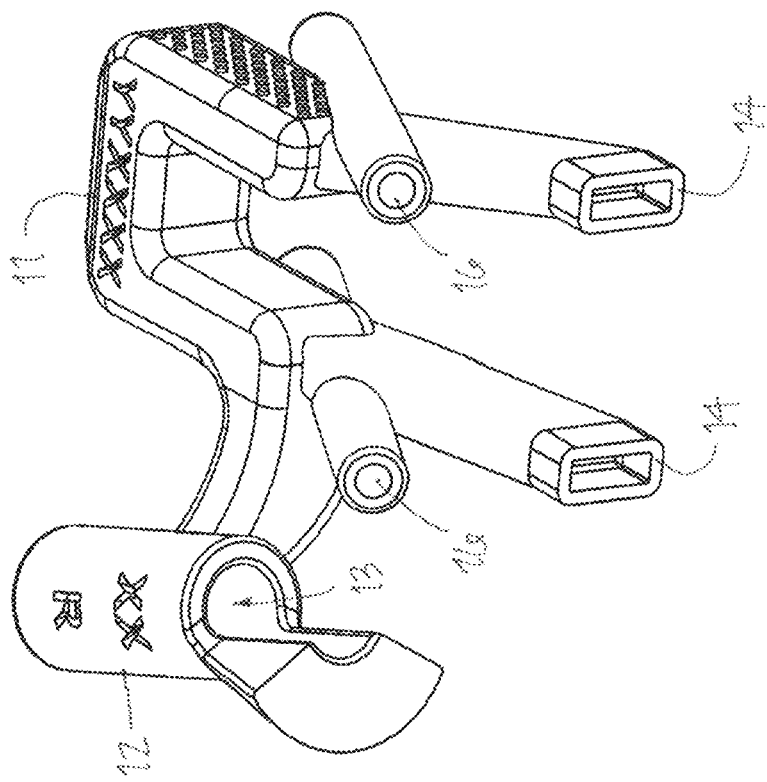
Figure 3:
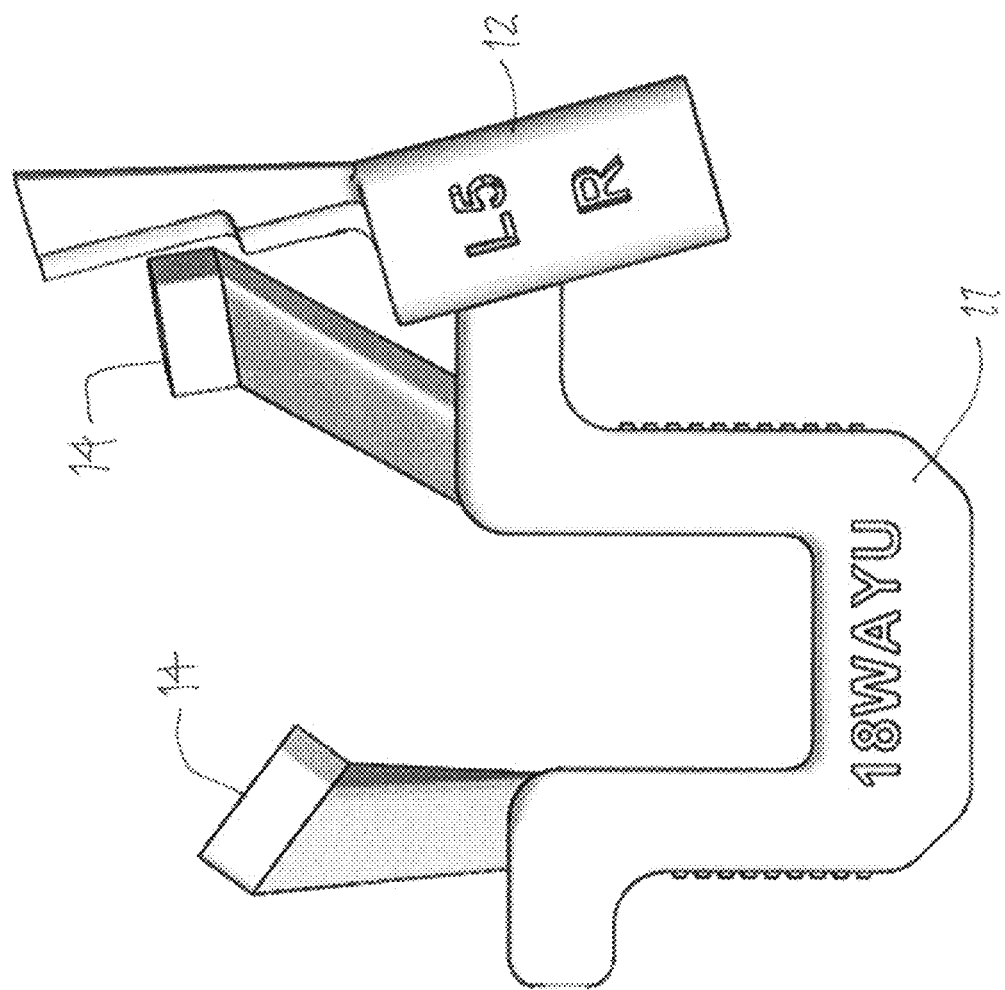
FIG. 3 is a plan view of another patient-specific guide according to embodiments of the present disclosure.
Figure 4:
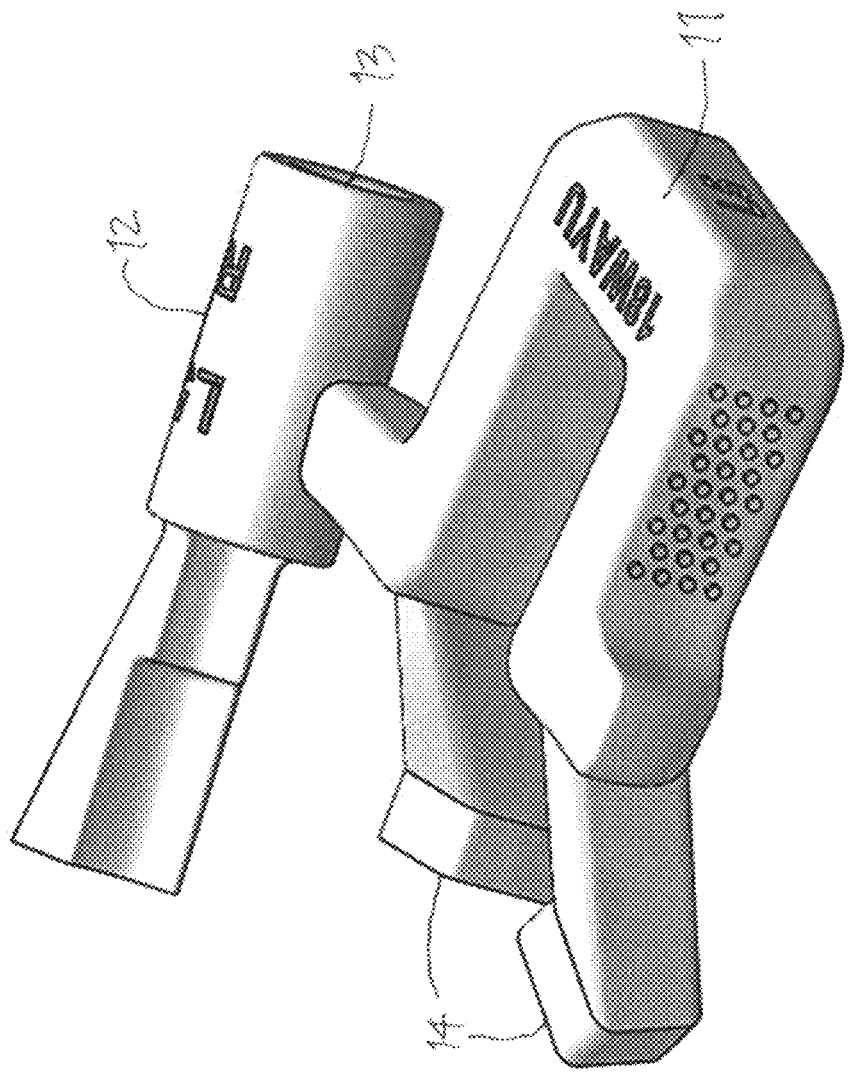
FIG. 4 is a perspective view of the guide shown in FIG. 3.

Reference is now made to FIGS. 2A-2B. As described above, the guide may include one or more legs. The legs may extend from one or more of the medial body and/or the cannulae. The angle and orientation of each leg with respect to the medial body may be varied to match the anatomy of the patient, or to avoid a portion of the patient's anatomy. For example, in FIG. 2A the legs may be offset from the cannulae to avoid specific anatomical features. Additional legs, as shown in FIG. 2B for example, may be provided to improve stability of accuracy of placement and registration of the patient-specific apparatus described herein. The guide may comprise several legs, with certain legs being primary legs and other legs being secondary or tertiary legs. In certain embodiments, the legs are each removable.

In one embodiment, at least a portion of the medial body, the cannulae, and the legs are configured to contact the patient's anatomy as shown in FIGS. 12-15, 26 and 28-29. For example, patient specific contact surfaces may be formed on one or more of the cannulae and one or more of the legs, respectively. Optionally, at least a portion of the medial body may be configured to contact a portion of the patient's anatomy. Accordingly, the medial body may also optionally include patient specific contact surfaces.

The contact surfaces may be adapted to fit directly to aspects of the patient's anatomy, such as one or more of the medial side of the inferior articular process, the lateral sides of the lamina, the spinous process, and the junction between the pars and the transverse process, the iliac, the sacrum, or other anatomical features of the patient. The patient-specific contact surfaces of the medial body may optionally contact at least a portion of the spinous process. The contact surfaces are determined to match at least a portion of a curvature of the patient's anatomy to facilitate placement of the guide in a predetermined alignment with respect to a predetermined portion of the patient's anatomy during a surgical procedure. The contact surfaces may be matched to substantially conform to a predetermined portion of the patient's anatomy by using the method described herein.

The patient contact surfaces may include any number of protrusions, depressions, and contours to substantially conform to the patient's anatomy. For example, the contact surfaces may comprise multiple portions that are adapted to contact two different planes formed by two distinct portions of the patient's anatomy. In this manner, the contact surfaces are adapted to one or more of: align the guide in a predetermined position and orientation with respect to the patient's anatomy; hook around a portion of the patient's anatomy; prevent unintended or inadvertent movement of the guide during a surgical procedure; and displace soft tissue. In one embodiment, the contact surfaces comprise relatively thin extensions to displace soft tissue. By protruding at least partially around and substantially conforming to different portions of the patient's anatomy, the contact surfaces generally "hook" at least partially around (or to) the patient's anatomy. Thus, the surfaces may contact at least two different planes formed by distinct surfaces of the patient's anatomy.

The surfaces provide a plurality of patient-specific contours for matching with a plurality of anatomical features of a patient. In this manner, the patient contact surfaces help position the guide and keep it in position in a predetermined position and orientation. The combination of patient specific surfaces formed on various locations of the guide may decrease the possibility of improper placement of the guide in relation to the patient's anatomy. The surgeon may also receive tactile feedback when advancing the guide into position with respect to a targeted portion of the patient's anatomy, such as a clip, snap, or vibration when the guide is properly aligned.

Alternatively, in another embodiment, the cannulae are adapted to guide an instrument or fixation device without contacting the patient's anatomy. For example, during some surgical procedures, a portion of a patient's anatomy may not be strong enough to provide a stable contact point for the guide. This may occur when the patient's anatomy has degenerated, is damaged, or is otherwise unstable. Accordingly, the cannulae of the guide may be adapted to float above the targeted portion of the patient's anatomy without touching the targeted portion.

Figure 5:
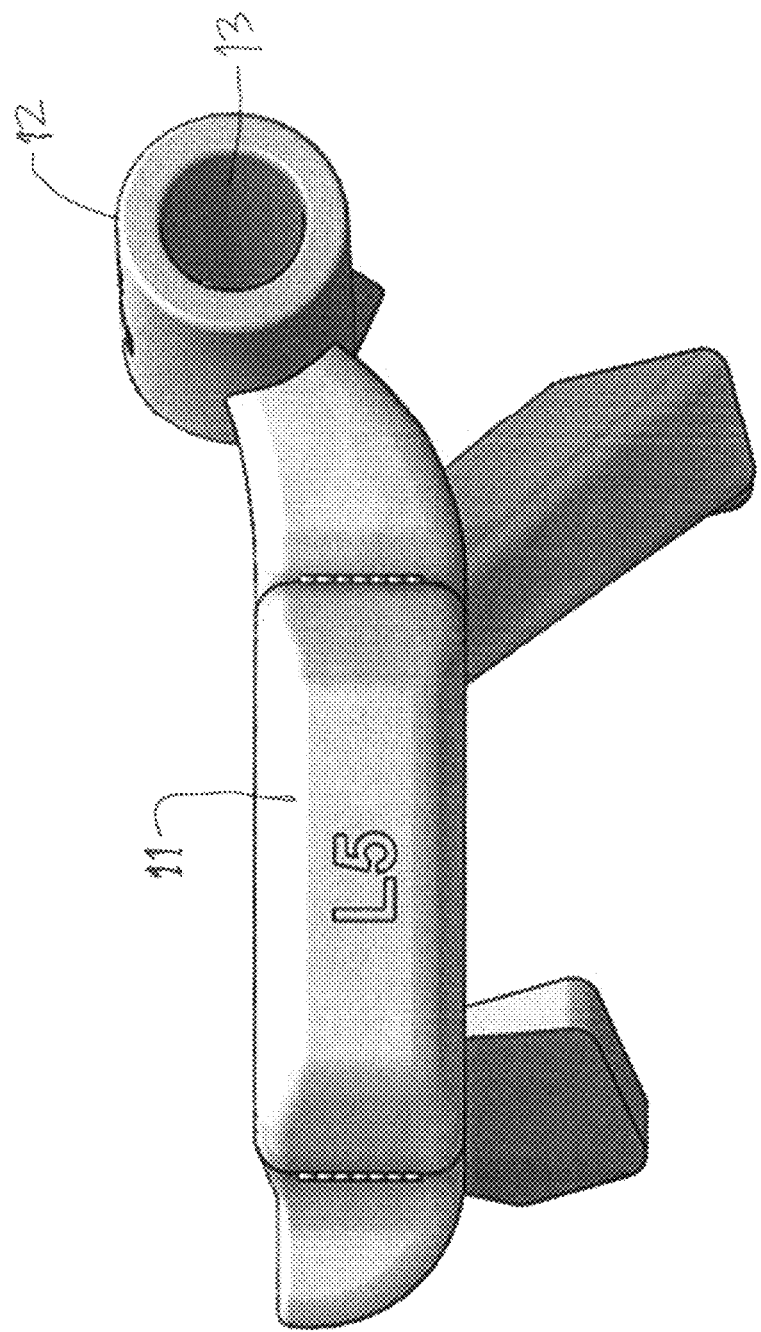
FIG. 5 is a side elevation view of the guide shown in FIG. 3.
Figure 6:
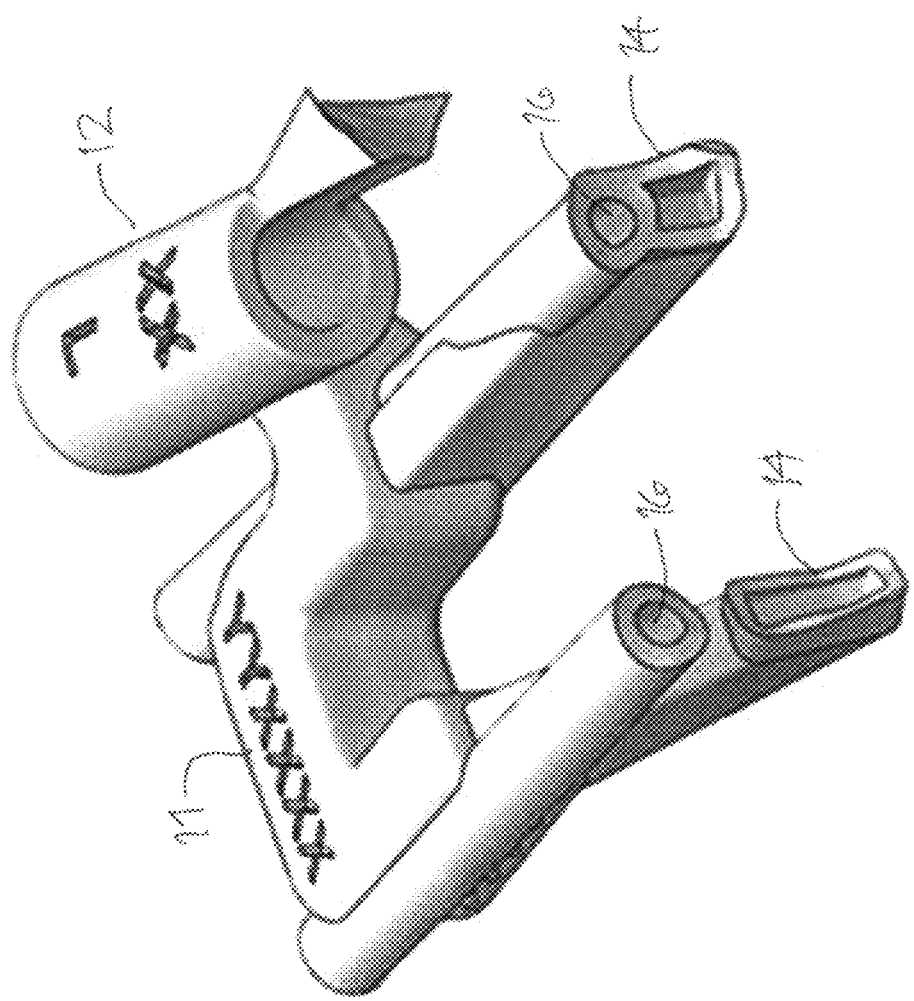
FIG. 6 is another perspective view of a guide according to embodiments of the present disclosure.
Figure 7:
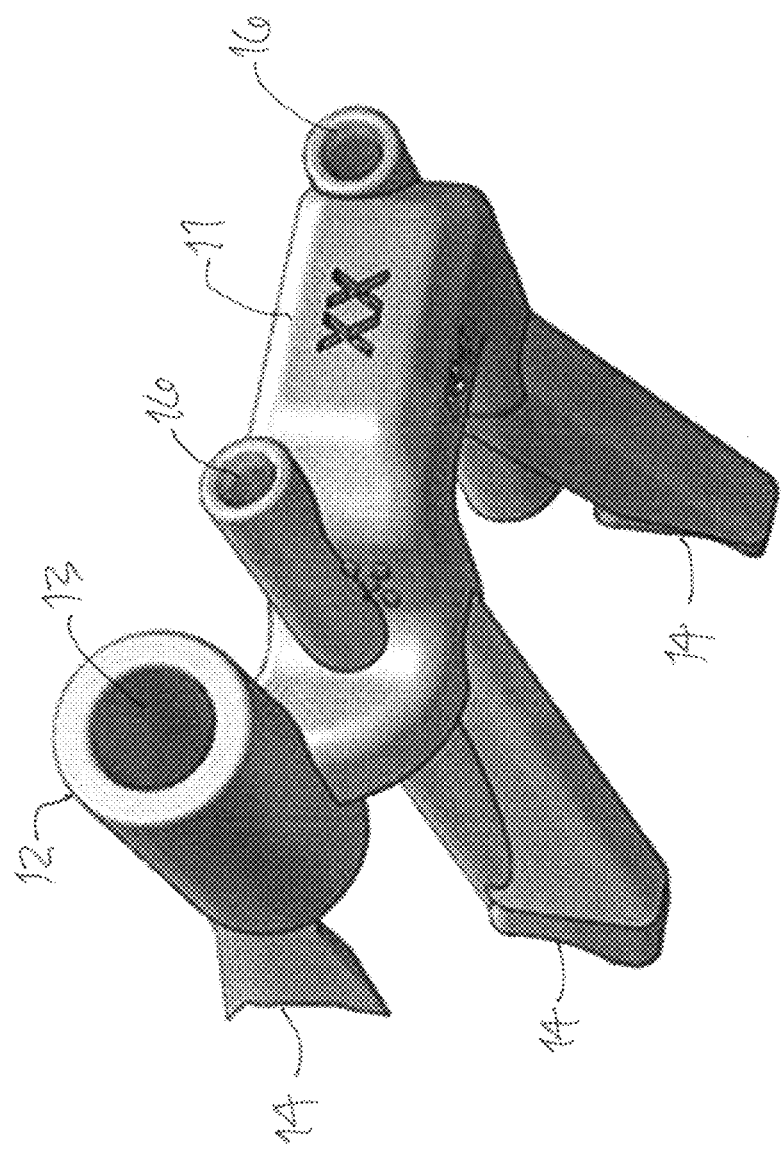
FIG. 7 is another perspective view of the guide shown in FIG. 6.
Figure 8:
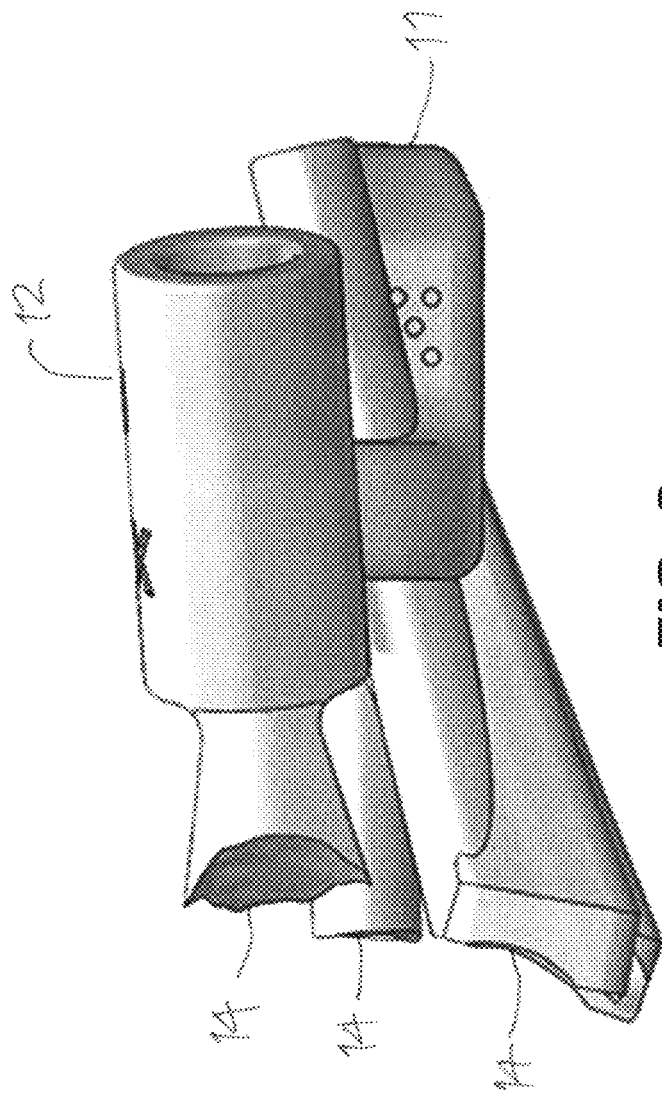
FIG. 8 is a side elevation view of the guide shown in FIG. 6.
Figure 9:
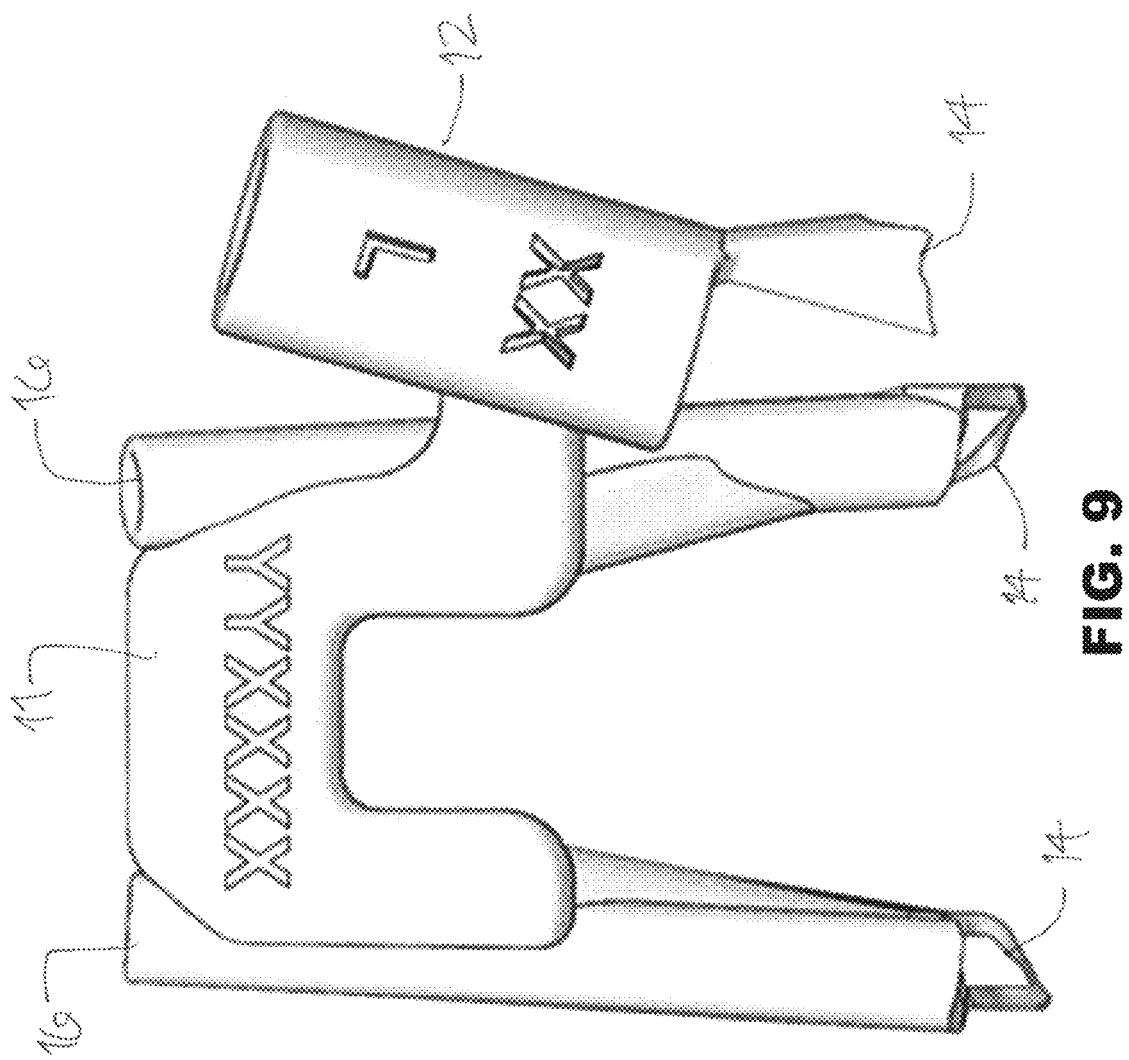
FIG. 9 is a plan view of the guide shown in FIG. 6.
Figure 10:
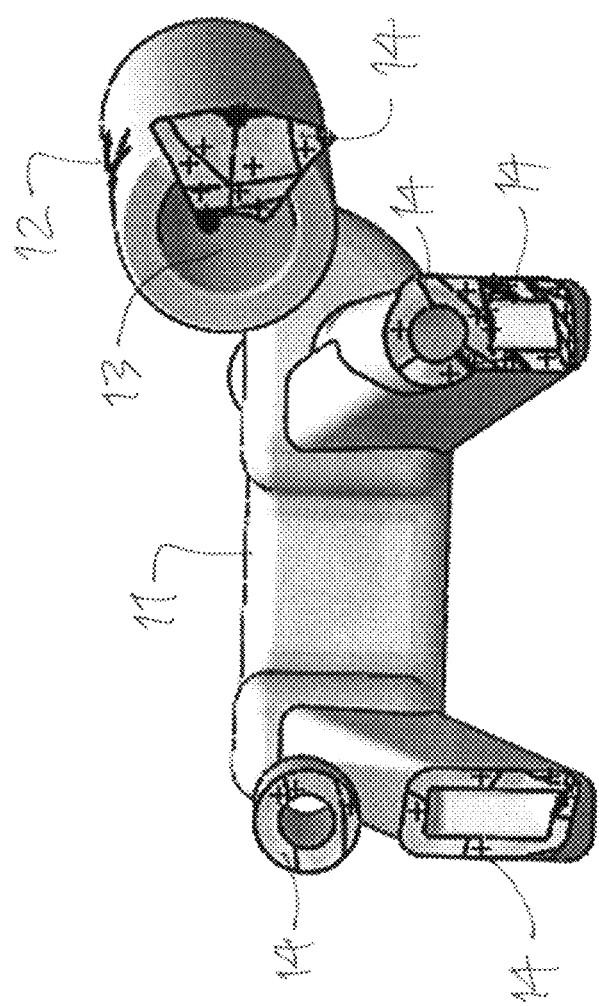
FIG. 10 is a bottom elevation view of the guide shown in FIG. 6.
Figure 11:
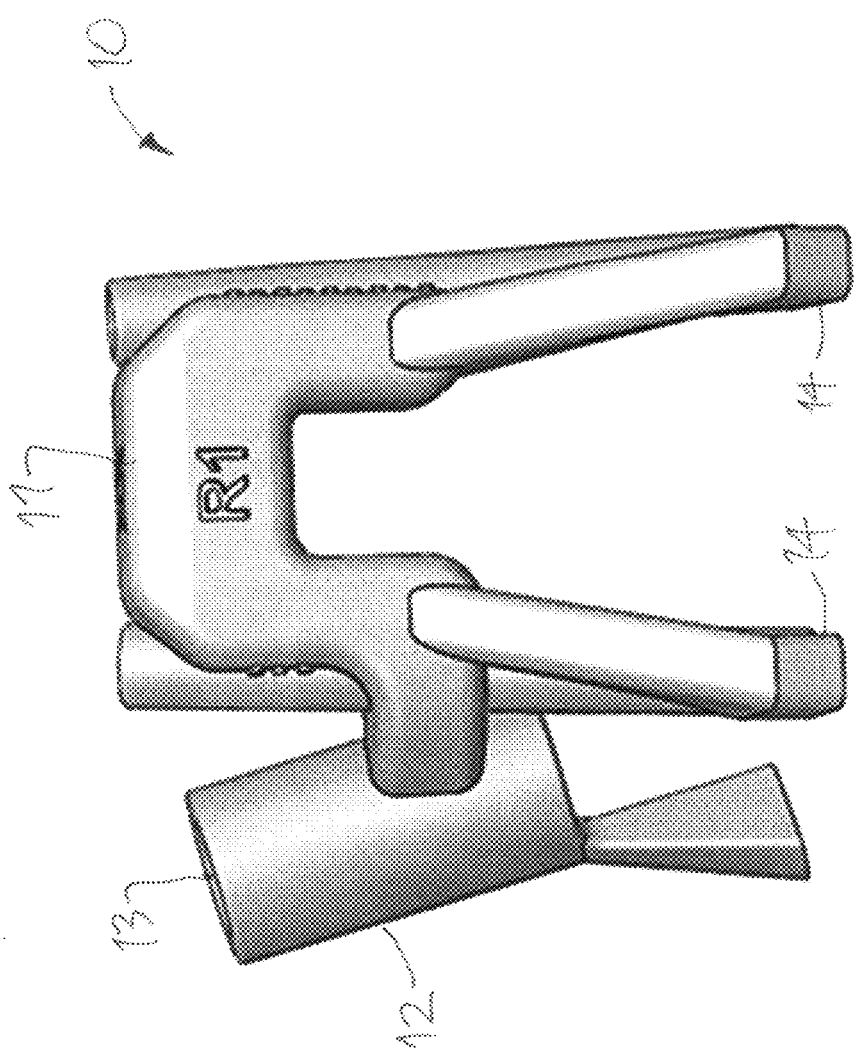
FIG. 11 is another plan view of the guide shown in FIG. 6.
Figure 12:
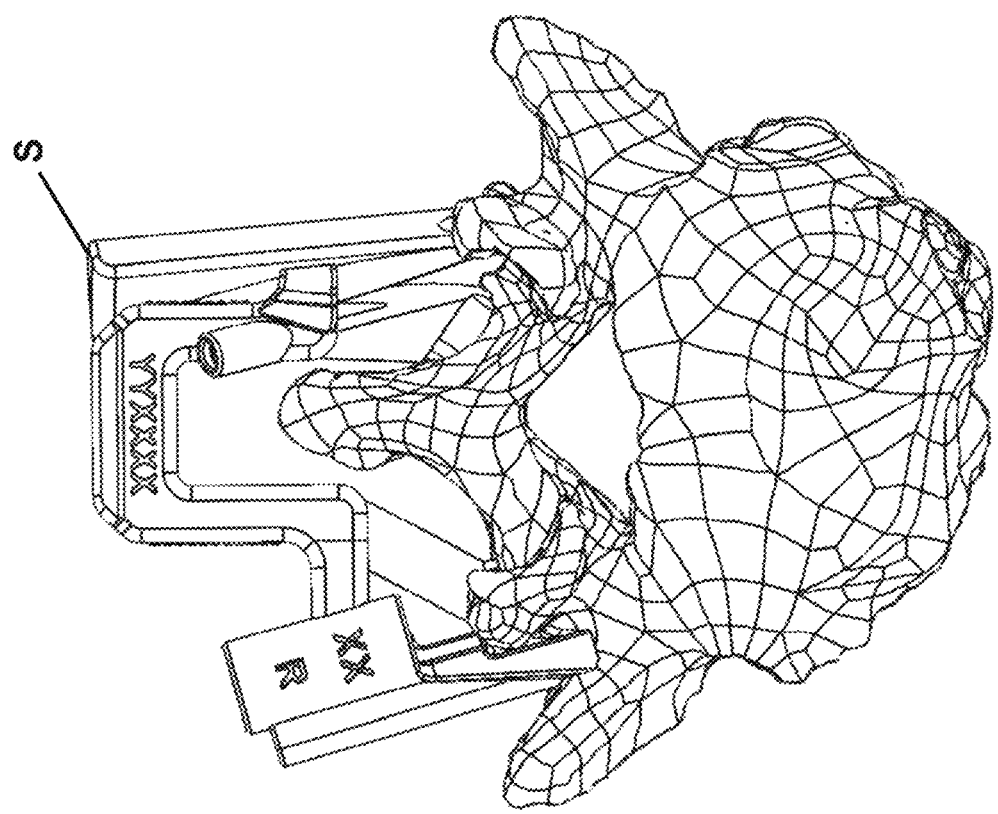
FIG. 12 is an image of the guide according to embodiments of the present disclosure.
Figure 13:
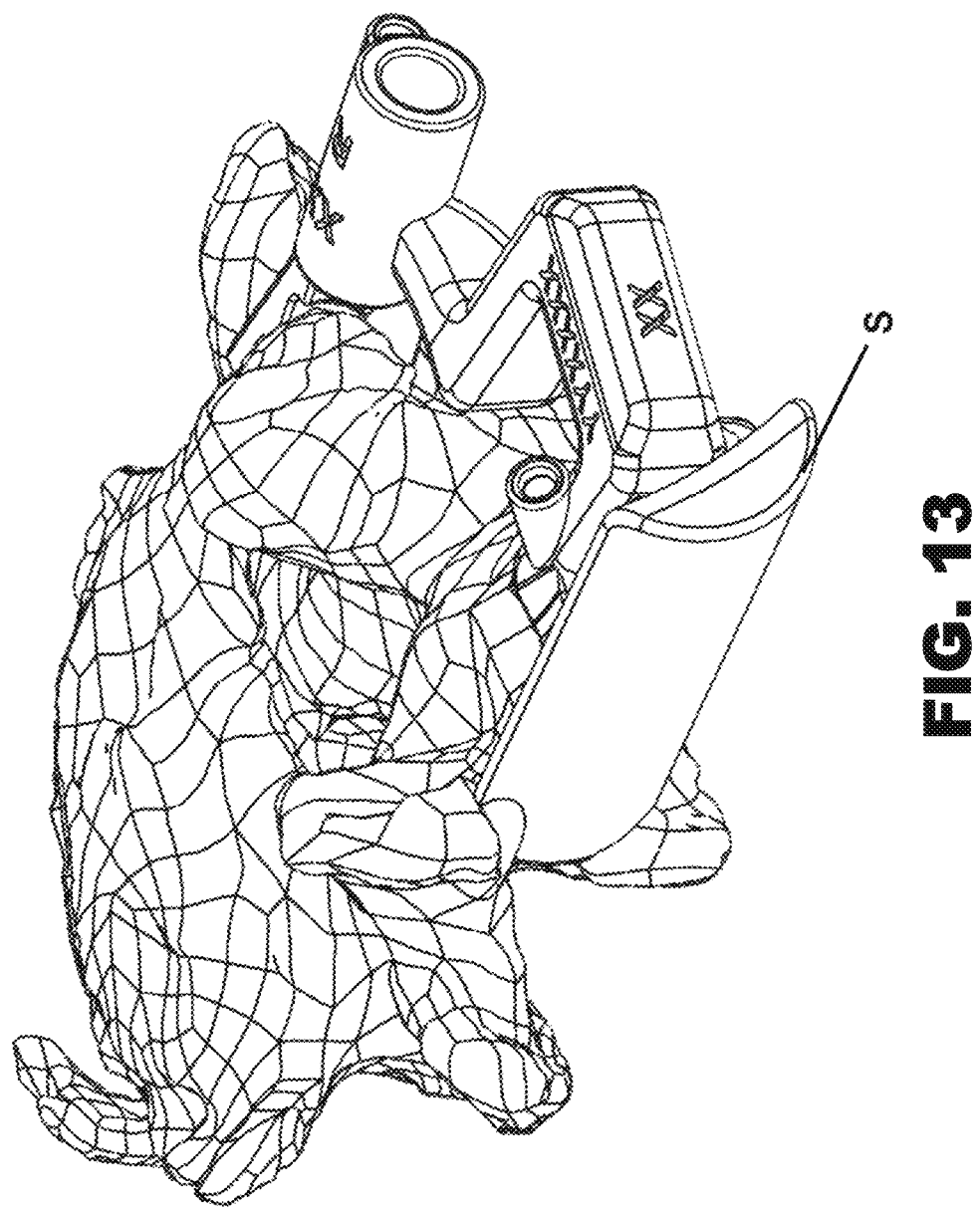
FIG. 13 is another view of the guide shown in FIG. 12.
Figure 14:
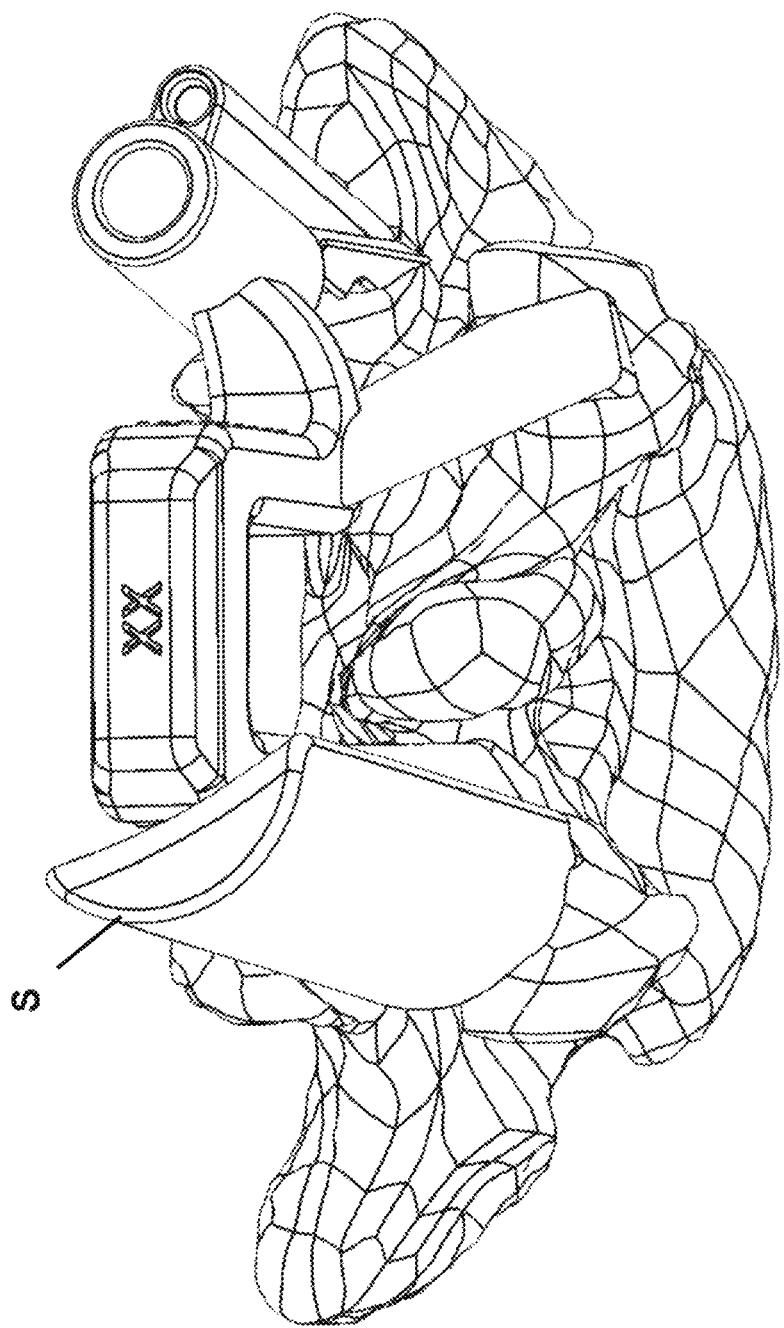
FIG. 14 is yet another view of the guide shown in FIG. 12.
Figure 15:
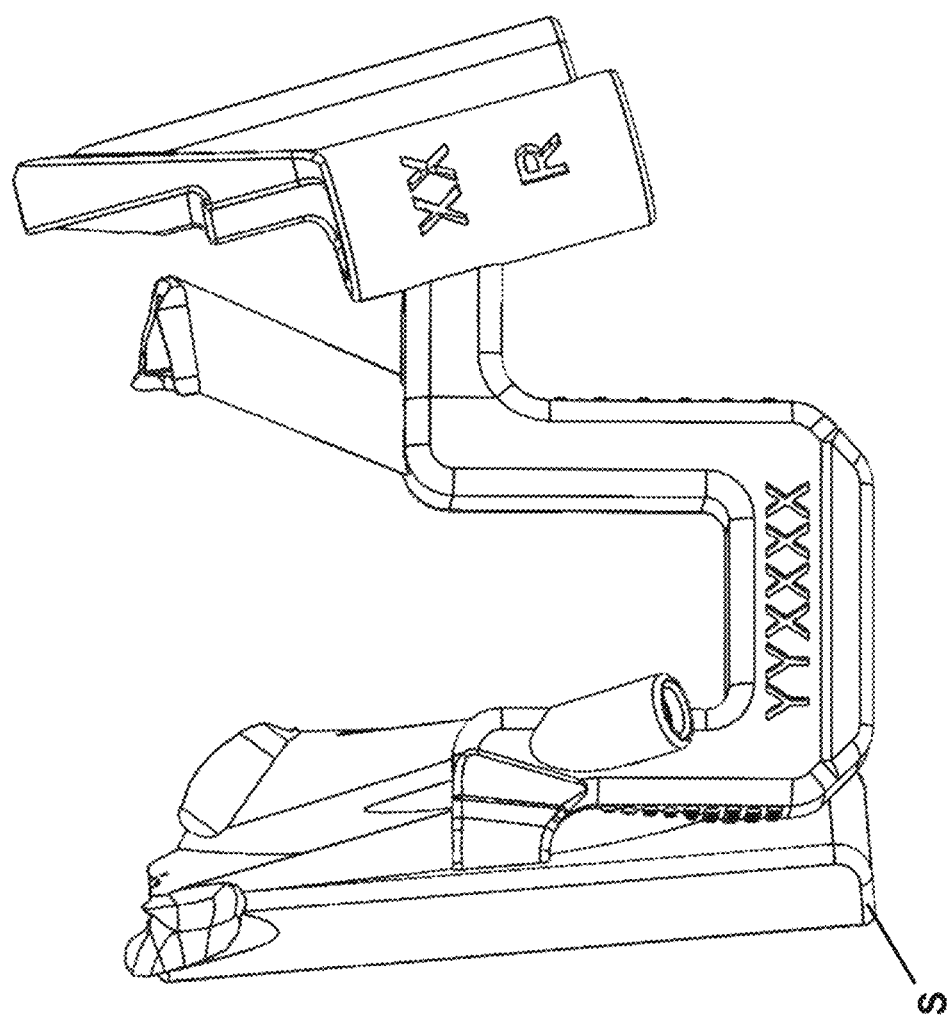
FIG. 15 is yet another view of the guide shown in FIG. 12.

At least one of the cannulae may include a bore to guide instruments and fixation devices, as shown in FIGS. 5 and 7, for example. The bore of each cannulae can have a unique internal diameter that is adapted to receive a particular instrument or fixation device. The internal diameter, or shape of the bore, may also be selected to prevent the use of the incorrect instrument or device with the guide. For example, a first bore may have a first cross-sectional shape and a second bore may have a second cross-sectional shape. The bore diameter and/or the length of the cannulae may also prevent the instrument or device from advancing into the cannulae beyond a predetermined distance, thereby providing a hard stop for depth control.

The bore may also have a shape adapted to align the tool or fixation device in a predetermined orientation of use. Additionally, a protrusion, key, notch, or void may be formed on the cannulae or in the bore to one or more of: prevent the use of the incorrect instrument or device; prevent an incorrect orientation of the correct tool or device; and prevent over insertion of the tool or device. For example, in one embodiment of the present disclosure, the cannulae bore may include an instrument contact surface that is associated with a feature of the tool, such as a protrusion, to control the depth or orientation of insertion of the tool. Thus, the cannulae may be adapted to prevent the instrument or fixation device from advancing too far into the boney anatomy of the patient or otherwise being misused.

Referring now to FIGS. 12-15, in certain embodiments the guide further comprises one or more surfaces configured to avoid potentially damaging contact between the surfaces of the guide and surrounding soft-tissue. In one embodiment, the surface in substantially planar and acts a shield to soft tissue on the opposite side of the spinous process as the at least one cannula. In other embodiments, a surface comprises an arcuate or curved surface to better distract the surrounding tissue while avoiding damage to the same. In embodiments, the shielding surface of the guide may be removable or adjustable to account for specific tissue the surgeon or health professional preferences.

In one embodiment, the bore of the at least one cannula may have different diameters and/or trajectories between one guide and another. In one embodiment, the bore is directed in a pedicle screw trajectory. In another embodiment, the bore is directed in a cortical bone trajectory. In another embodiment, the bore is directed in a cortical trajectory, a sacral pedicle trajectory, a sacral alar trajectory, an S2-alar-iliac trajectory, or an iliac trajectory. The guide and/or bore is not necessarily cylindrical and may comprise other shapes to conform to the shape of an instrument or implant delivered therethrough.

In still another embodiment, the body further comprises a second bore that is oriented in a direction for placement of a temporary fixation device. In embodiments, the guide 10 may comprise a second bore, also referred to as an alignment channel 16, for inserting a guide wire, K-wire, Jamshidi needle or other securing element through the guide and into the underlying boney anatomy. The alignment channel 16 may receive a fixture, such as a temporary fixation device, to temporarily fix the guide 10 to the patient's spine or other anatomical feature. The temporary fixation device may be a pin or screw such as those known to one of skill in the art. Placing a fixture through the channel 16 can increase stability of the guide during use of the guide, or may simply temporarily secure the guide in a position convenient for aligning the patient specific surface 14 with the corresponding patient anatomy and removed at a later time.

Optionally, the channel 16 may comprise a cannula adapted to receive a tool, such as a tool for forming a bore in the patient's anatomy. Thus, in one embodiment, the alignment channel 16 may optionally comprise a bore adapted to guide an instrument or a fixation device, such as a pedicle screw. In one embodiment, the channel 16 comprises a cannula to receive a drill to form a bore. The bore may be used with a patient specific fixation device.

In one embodiment, the guide 10 designed following acquisition of a scan of the patient's anatomy with a medical imaging device. The scan may be performed by a CT scanner, an MRI scanner, or any other medical imaging device. The scan is segmented into 3D models of each vertebra. These 3D models are then modified in CAD to simulate the correction desired by the surgeon. Once the desired correction is appropriately simulated, a guide 10 is generated that will allow the surgeon to make the planned corrections intraoperatively. The guides may then be manufactured through 3D printing, rapid prototyping, or an alternative method for creating patient-specific features.

The guides of the present disclosure can be used as physical cutting guides, drill guides, bone removal guides, implant guides, screw guides, instrument guides or guides for other surgical equipment or instrumentation. Additionally, the guides may be used as an aid to indicate to surgeons the angle and location of drilling or cuts so that neural elements in the patient's spine are not harmed. The guides may also be used pre-surgically on models of the patient's anatomy to test or practice the planned surgical procedure. At least a portion of the proximal end of the guide is configured to extend outside of the patient during a surgical procedure.

Various apparatus formed by the system and method described above may be used for a particular fixation related surgery. The guides described herein may be used for navigation of one or more of a cortical bone trajectory, a pedicle screw trajectory, and other trajectories in the spine of a patient. As will be appreciated by one of skill in the art, the cortical bone trajectory, unlike the pedicle screw trajectory, has a medial entry point and diverges superior and laterally (or "up and away") when advancing anteriorly through the pedicle. Additionally, the cortical bone trajectory allows for a greater amount of fixation in cortical bone as opposed to pedicle screw trajectories which achieve fixation mostly in cancellous bone.

In embodiments, the patient-specific apparatus, as described herein, may be used in conjunction with particular robotic, navigational or motion control systems, including systems pertaining to fixation-related surgeries. For example, the apparatus shown in FIGS. 16-21 may be used in conjunction with an autonomous or semi-autonomous system for assisting with a particular surgical procedure.

Figure 16:
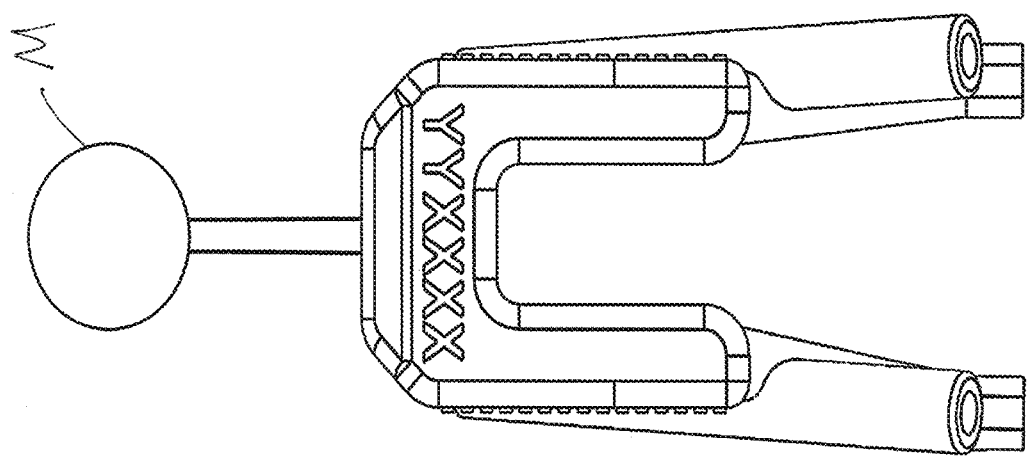
FIG. 16 is a plan view of a patient-specific apparatus according to embodiments of the present disclosure.

Referring to FIG. 16, a patient-specific apparatus may be provided that comprises one or more legs and/or one or more alignment channels but no cannula. This guide preferably comprises at least two distal surfaces that are patient-specific and designed to contact the patient in two unique locations, preferably on a single vertebral level. This no cannula guide preferably includes a registration marker M for use in conjunction with robotic navigation and or autonomous/semi-autonomous systems described herein. In certain embodiments, the registration marker is removable. Alternatively, the registration marker may be embedded into the guide. By way of example, several no cannula guides may be placed along the patient's spine, in distinct vertebral locations, and thereby provide the user with the ability to register various locations for surgical planning or, in certain embodiments, robot-assisted navigation.

Several of the patient-specific guides described herein may be used with various orientation or registration markers M for identification by a robot. Certain guides may comprise an embedded chip, circuit or equivalent medium with pre-surgical planning information, which may be read by a machine and deliver specific instructions to a robotic surgical device, for example. In this manner, a surgeon may attach a patient-specific apparatus (such as the one shown in FIG. 16) to each level of the patient's spine that is impacted by a particular surgical procedure, and thereby provide markers for registration and orientation without having to rescan the patient throughout the surgery. In turn, the robotically guided surgical device may view the patient through the markers M and align instrumentation controlled by the robotic equipment. This alignment may be achieved by any one of a combination of guides/markers/patient-specific orientation guides.

Figure 17:
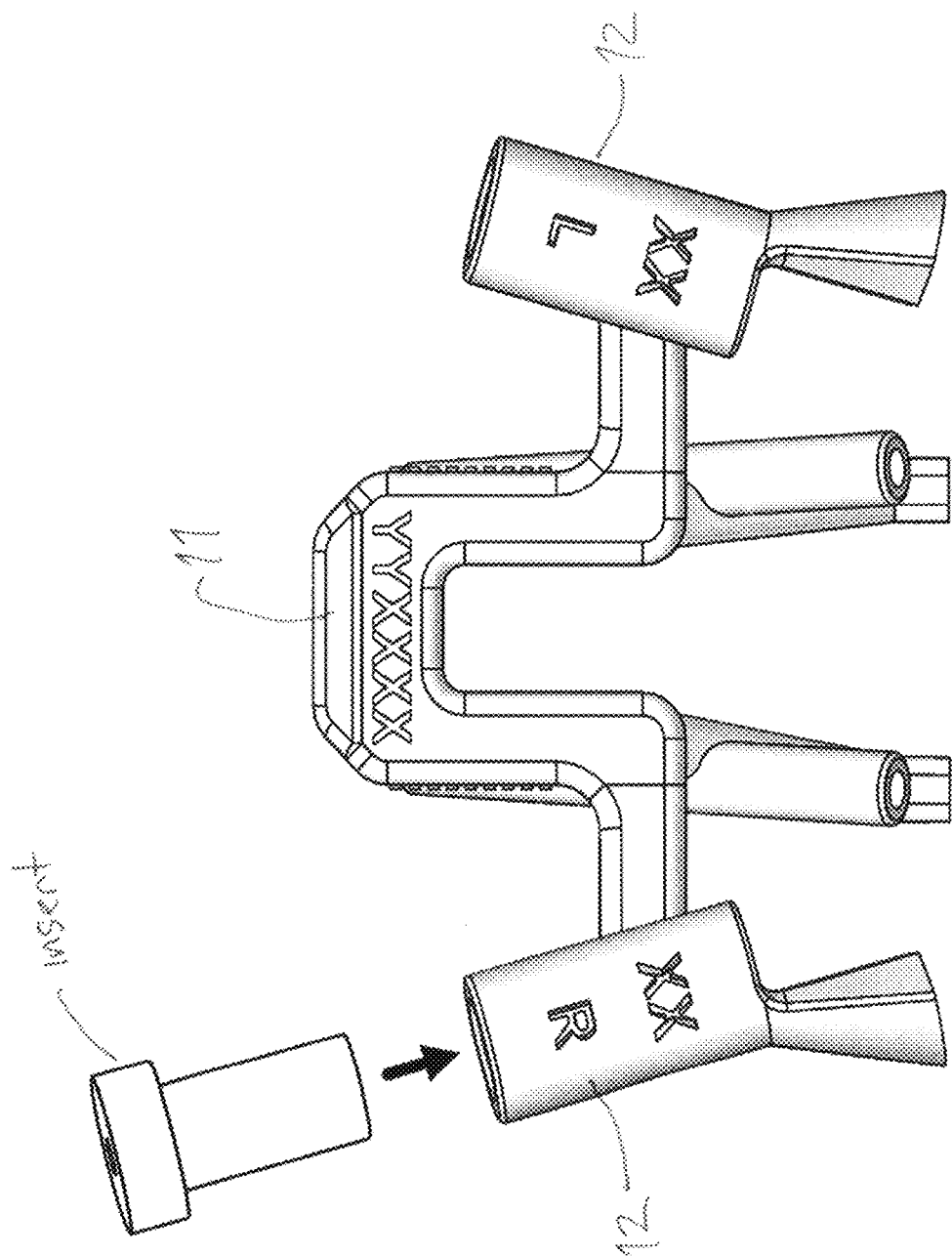
FIG. 17 is a plan view of another patient-specific guide according to embodiments of the present disclosure.
Figure 18:
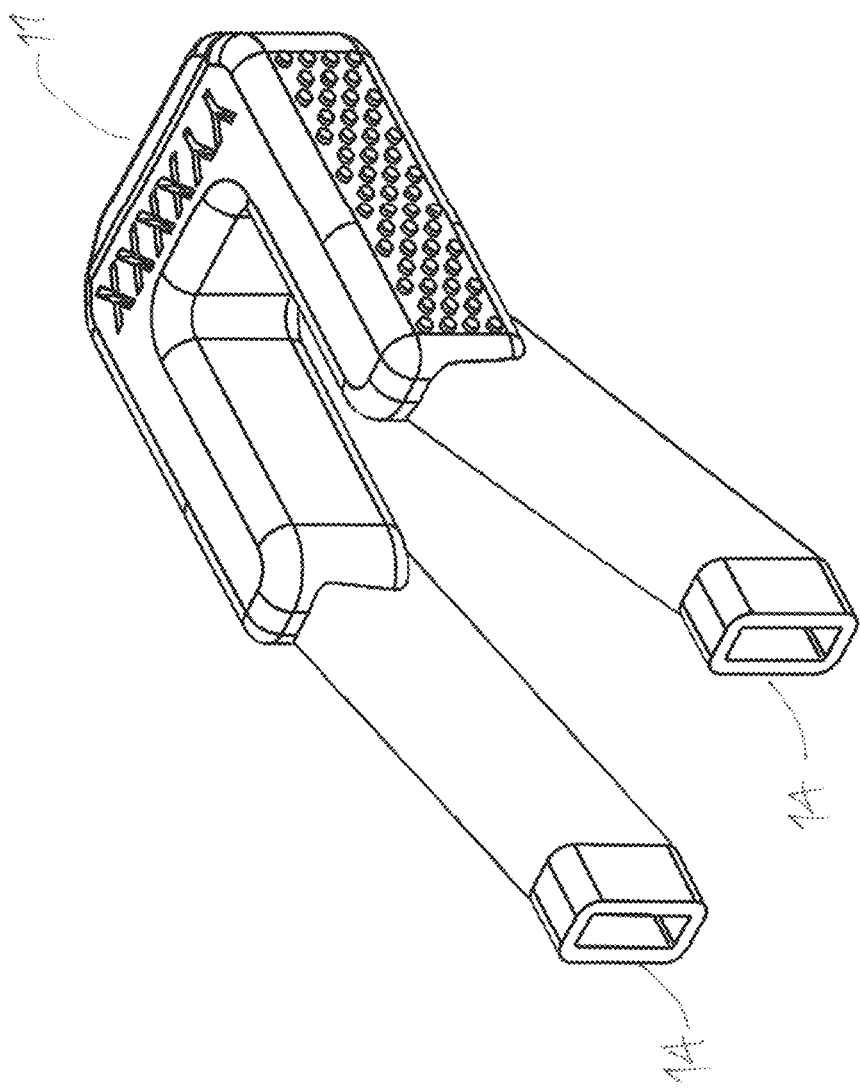
FIG. 18 is a plan view of another patient-specific apparatus according to embodiments of the present disclosure.
Figure 19:
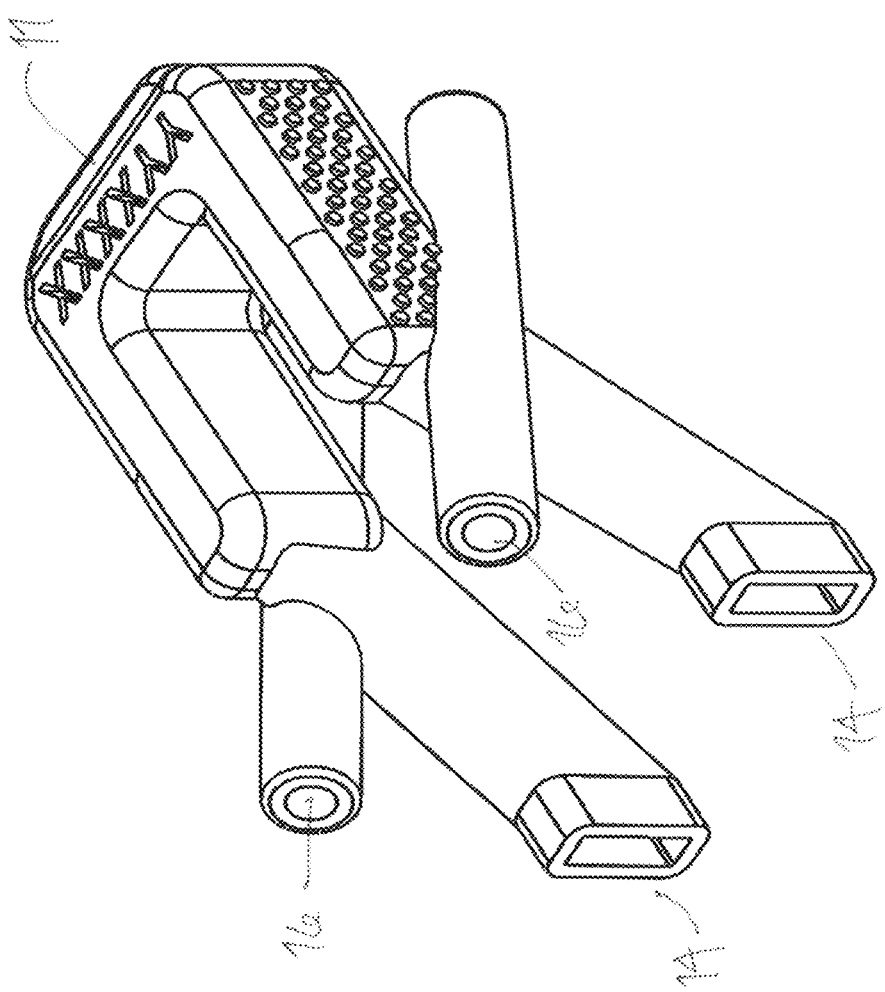
FIG. 19 is a plan view of another patient-specific apparatus according to embodiments of the present disclosure.
Figure 20:
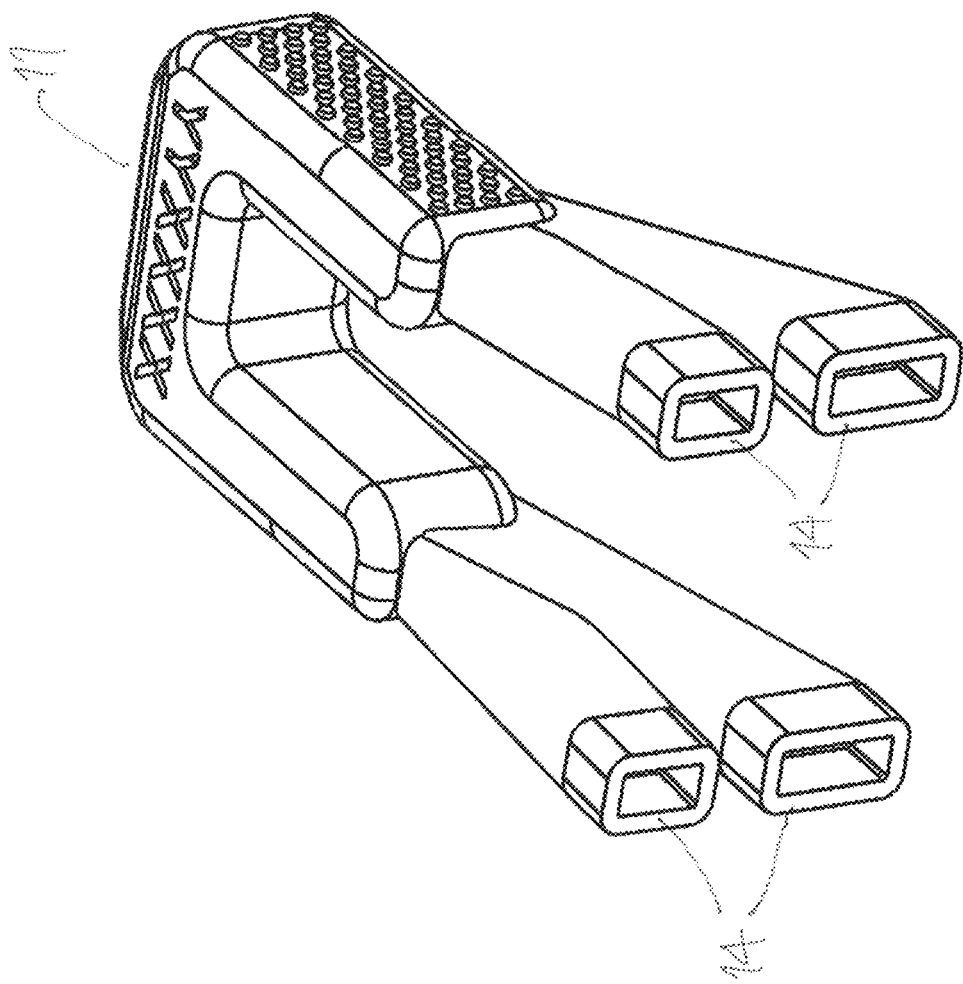
FIG. 20 is a plan view of another patient-specific apparatus according to embodiments of the present disclosure.
Figure 21:
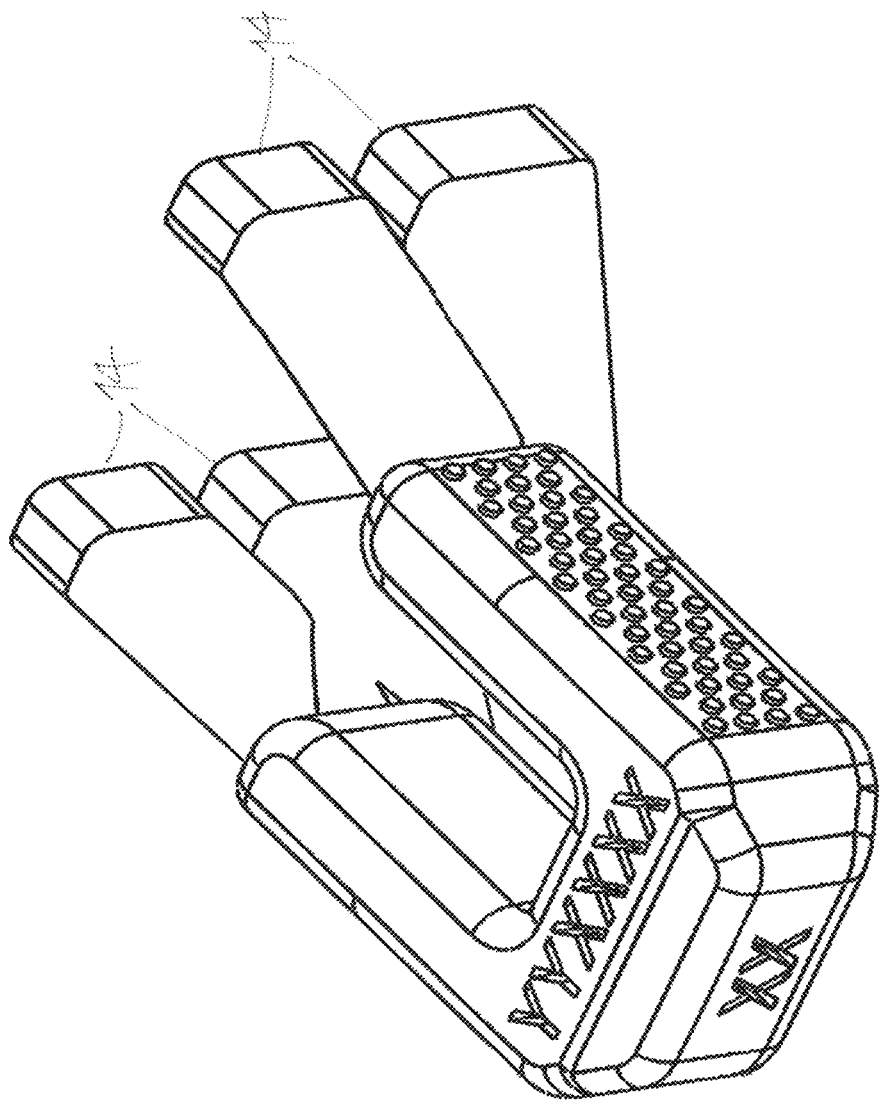
FIG. 21 is a plan view of another patient-specific apparatus according to embodiments of the present disclosure.
Figure 22B:
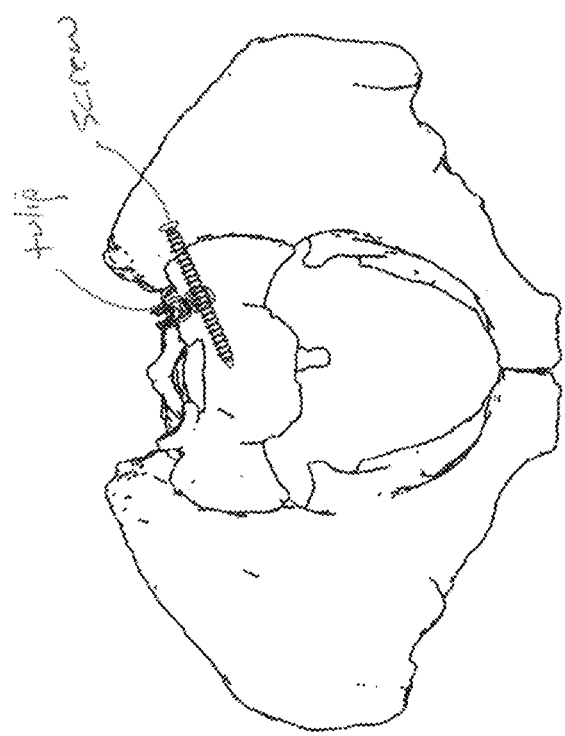
FIGS. 22A-22B are illustrations of an iliosacral screw and associated tulip according to embodiments of the present disclosure.
Figure 22A:
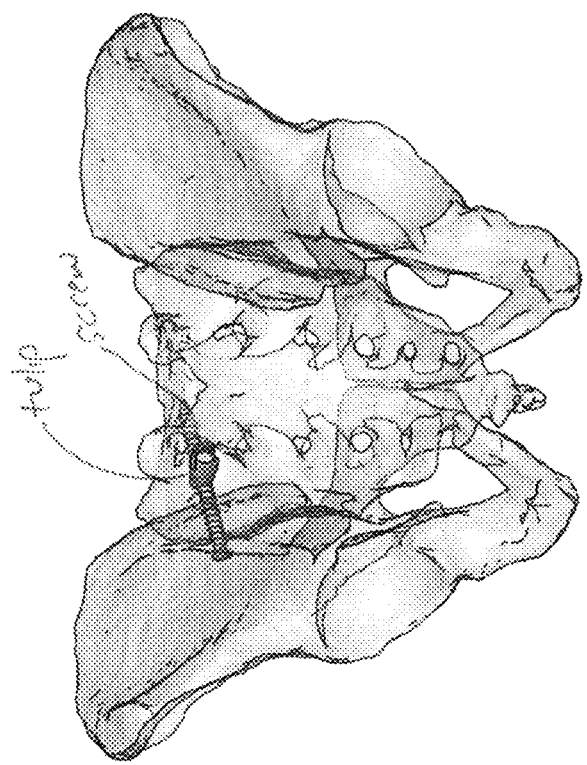
Figure 23B:
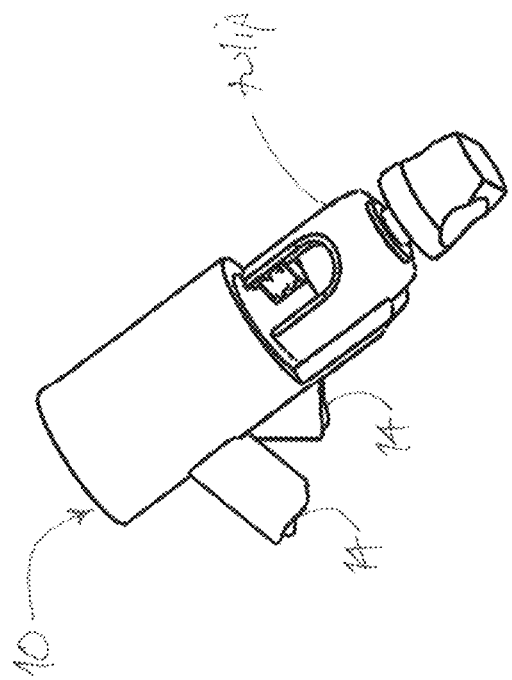
FIGS. 23A-23B are perspective views of another patient-specific guide according to embodiments of the present disclosure.
Figure 23A:
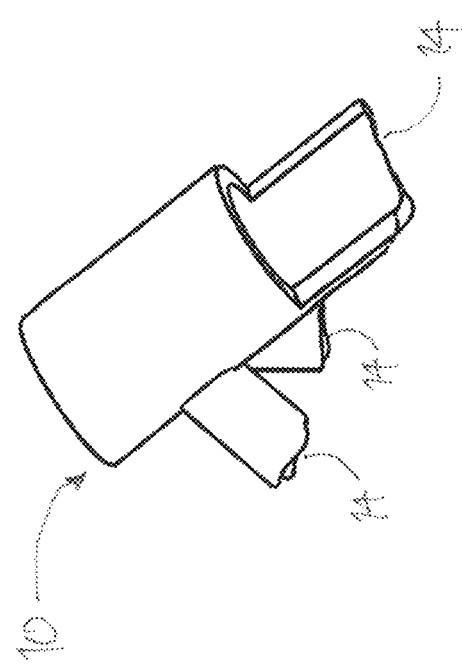
Figure 24B:
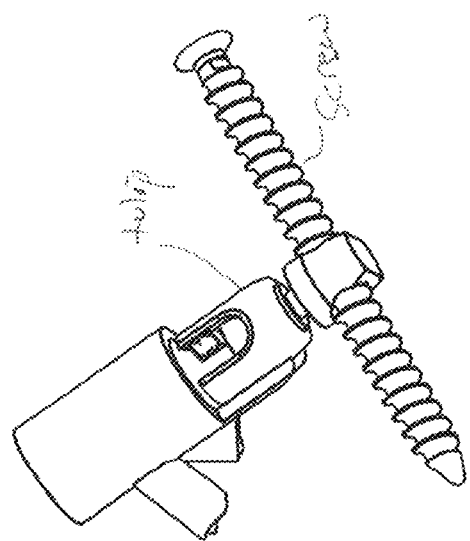
FIGS. 24A-24B are additional perspective views of the patient-specific guides shown in FIGS. 23A-23B.
Figure 24A:
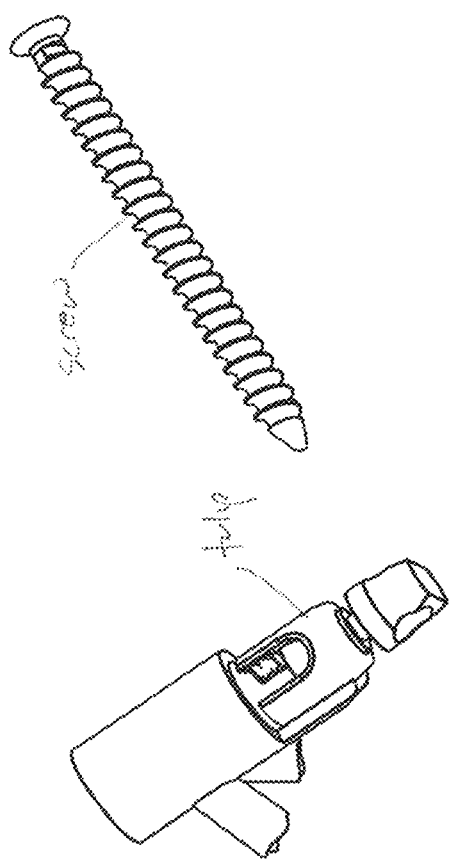
Figure 25:
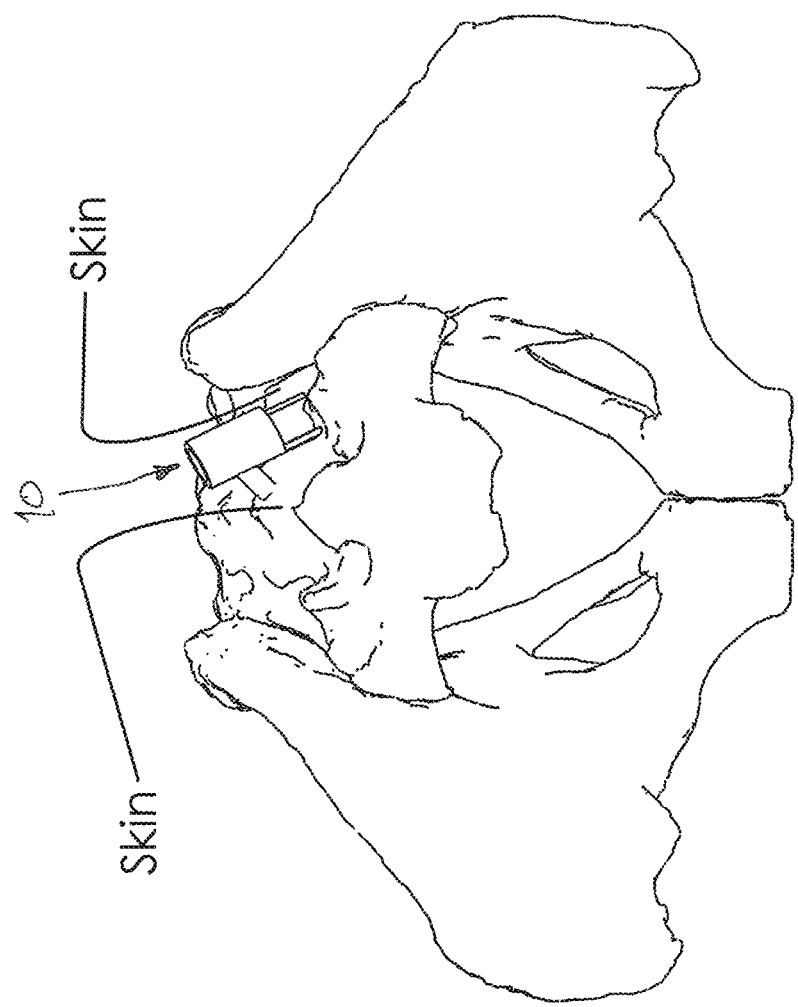
FIG. 25 is a perspective view of the guide of FIGS. 23A-24B shown against a patient's boney anatomy during a minimally invasive surgical procedure.
Figure 26:
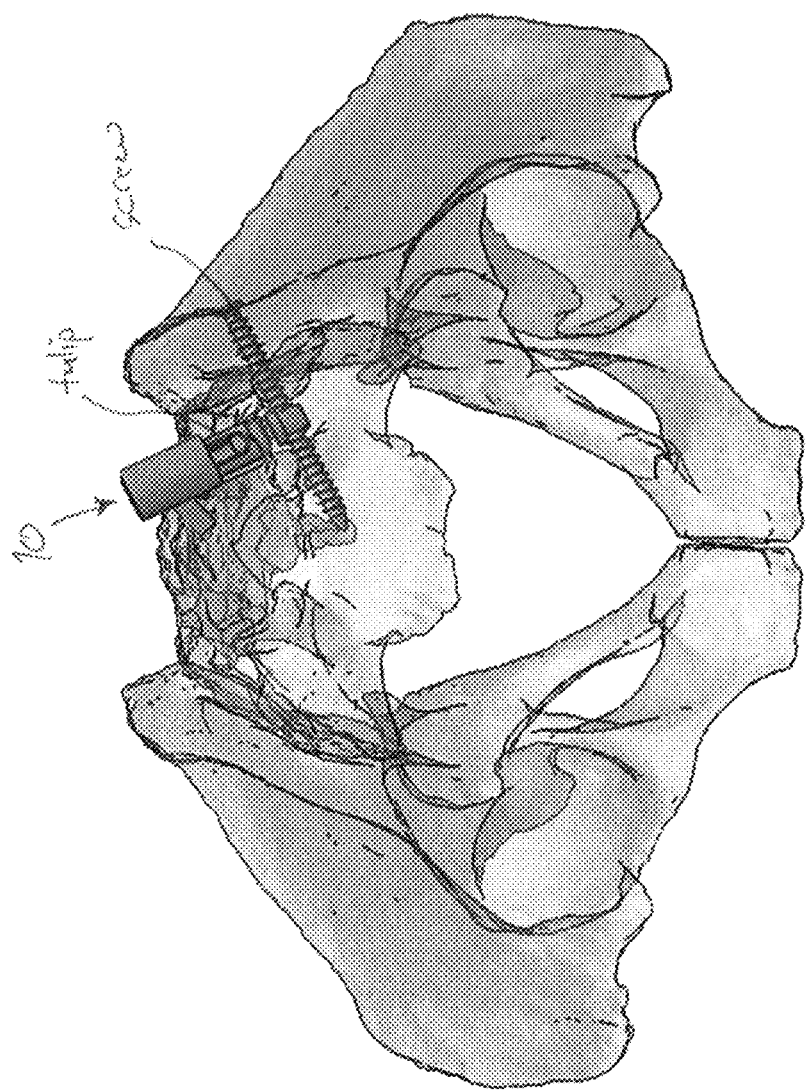
FIG. 26 is a perspective view of the guide of FIGS. 23A-24B shown against a patient's boney anatomy with a iliosacral screw placed through the distal end of the tulip.

Furthermore, as shown in FIG. 17, 3-D printed drill sleeves may be provided with embedded locating/information markers. Thus, when the sleeves are inserted into a patient matched guide, the robotic device(s) may orient robotically controlled instruments relative to the drill sleeves location and embedded information on each level a guide is present. In certain embodiments, such as with a prior fusion procedure, only one guide/locating marker would be needed. In some embodiments, the drill sleeves are 3D printed with metal or plastic material. In other embodiments, the sleeves are fabricated using one of the other methods described herein.

The "no cannula" guides may further comprise the ability to accept one or more measurement devices for facilitating the surgeon/user in identifying landmarks, surrounding boney anatomy, placement of implanted devices, or for surgical planning. Each of the guides may be adapted for use with a specific vertebra. The guides may be formed according to the methods described herein, or by any other suitable method.

Guides with no cannula, such as those shown in FIGS. 16 and 18-21, may be used as a tool to measure correction obtained in surgery. For instance, any of the foregoing guides may be placed on a patient's anatomy at the beginning of surgery and provide an initial angle to the user. In certain embodiments, the guides are configured to accept a protractor or equivalent device to better define the angle(s). Further, once a surgery is completed, the protractor or equivalent device may be applied again and the change in angular measurement between the initial and post-surgical measurements dictates how much correction was achieved. These measurement features may also be used in conjunction with a registration marker instead of a protractor.

Autonomous and semi-autonomous systems may further comprise an adjustable arm assembly, which may be affixed to a piece of machinery, an operating surface or alternatively to the patient. The arm assembly may substantially facilitate the placement of surgical screws during spinal surgeries by securing the guide and corresponding coupling devices to a stationary surface, thereby providing greater stability and, in turn, more accurate placement of screws and/or other fixation devices. For example, a patient specific guide may be engaged with the corresponding patient specific anatomy of a desired surgical site. An adjustable arm assembly, which is secured to a stationary surface, such as an operating or side table or other surface, can then engage the guide via corresponding coupling devices to provide greater stability and delivery of fixation devices therethrough. This attachment between the device(s) and the arm assembly may permit a user to set and fix, for example, the sagittal angle of the device(s) when performing a surgical procedure on the patient's spine.

Alternative embodiments may also include an arm assembly, wherein the arm assembly comprises a telescoping member that rests at least partially on the patient's skin, which may be adjusted to a desired length and angle relative to the associated device(s). This serves to hold the handle of the device(s) in place when the user is not grasping the handle. Each of these embodiments preferably includes a locking mechanism for securing the arm assembly components in place over the desired orientation and position has been established.

One having skill in the art will appreciate that embodiments of patient specific guides, as well as other embodiments discussed herein, may be used in conjunction with devices that employ automated or semi-automated manipulation, such as, for example, robotics, image guidance or other autonomous systems. Embodiments of patient specific guides may also be designed such that the guide may be operated and verified, in whole or in part, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. These apparatus and systems may be programmed to operate with the patient-specific guides, the same having known dimensions and therefore provide ease of validation and operation by automated or semi-automated means.

In one embodiment discussed above, for example, the adjustable arm assembly may be associated with, or controlled by, a robot, programmable apparatus, CNC machinery or equivalent equipment used to perform a surgical procedure. In other embodiments, the guide may be configured for use in conjunction with or to further supplement the use of a navigation device. More specifically, autonomous placement of the patient specific guide via the adjustable arm assembly with the corresponding anatomical feature(s) of the patient assists with one or more of registration, stability, and motion tracking. The navigation device coupled with the adjustable arm assembly and/or patient-specific guide may optionally track the position of instruments, equipment or hardware in relation to the patient's anatomy during a surgical procedure. Accordingly, the navigation device may display positions of instruments, equipment or hardware as they are used during the surgical procedure. In yet other embodiments, the placement of the guide may supplement the registration, stability and motion tracking features provided by the navigation device. In these embodiments, such surgical procedures may be entirely or partly performed via autonomous or semi-autonomous systems and methods so as to limit the exposure of certain harmful or toxic chemicals or transmissions (e.g., radiation) to the surgeon and other attending medical staff. Such autonomous and semi-autonomous systems and methods may also substantially increase the speed and accuracy of the surgical procedure.

Each of the guides illustrated in FIGS. 1-21 can interface with any vertebra level or more than one vertebra level, including without limitation the cervical, thoracic, lumbar, and sacrum. Further, each of the guides include at least one cannulae. The cannulae may include a bore adapted to guide one or more guide wires, drill bits, taps, and screws. Thus, the bore may guide a drill apparatus and/or a fixation device. Optionally, a cannula may be devoid of a bore. The cannula without a bore is adapted to provide stability as other portions of the guide are used in a surgical procedure. Additionally, or alternatively, the guides may comprise secondary and/or tertiary cannulae adapted to guide one or more of the group comprising guide wires, drill bits, taps, screws, couplings, and other instrumentation including without limitation tools adapted to harvest bone grafts. The cannulae may be of a variety of lengths. In one embodiment, at least a portion of the proximal end of the cannulae and the guide is configured to extend outside of the patient during a surgical procedure.

Any of the guides may include a track or slot adapted to guide an instrument operable to remove a predetermined portion of a vertebrae. The slot may include patient-specific depth control, angle, and orientation. Any of the guides of FIGS. 1-29 may be used with, or include, surgical or medical tools, guides, wings, bodies, and other patient-contacting apparatus.

In one embodiment, at least a portion the guide is reusable. Optionally, at least a portion of the guides projects beyond the patient's anatomy when in a position of use during a surgical procedure. For example, at least a proximal portion of a cannulae of one or more of the guides may project from an incision formed during surgery.

Other benefits achieved from the use of these patient-specific guides described in conjunction with of FIGS. 1-29 include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Additionally, the patient-specific guides may comprise individual pieces that are adapted to be assembled by a surgeon before, or during, a surgical procedure. The portions or components of the guides may be disassembled and delivered to a specific area of the patient's anatomy for assembly during the surgical procedure. For example, the medial bodies, cannulae, and legs of the guides may pass through a bore of a cannula of another tool and assembled during a minimally invasive surgical procedure.

The cannula described herein may be configured to contact one or more of the lamina, pars interarticularis, aspects of the transverse process, the interior articular process, and the superior articular process of the patient. Cutouts (not illustrated) may be formed on a portion of the cannulae to prevent the guide from contacting the spinous process of the patient, adjacent vertebrae, or to avoid other patient anatomy.

The cannulae may have a generally cylindrical shape but other shapes are contemplated. Each of the two cannulae may have a unique orientation and size. The cannulae may be of any length based at least in part on the specific patient's anatomical features, preferences of the surgeon, orientation of the guide, and the type of tool or fixation device associated with the cannulae. The length of the cannulae may also be selected to provide depth control of instruments guided by the cannulae. For example, in one embodiment, the cannulae has a first length to allow a drill bit to penetrate a first depth into the patient's anatomy. In another example, the cannulae has a second length that is greater than the first length. Accordingly, the cannulae prevents the drill bit from penetrating the first depth into the patient's anatomy.

The cannulae may optionally include extensions of any size or shape. In one embodiment, the extensions are positioned proximate to a distal end of the cannulae. In another embodiment, the extensions wrap at least partially around the exterior of the cannulae. The extensions may also project at least partially beyond the distal end of the cannulae. The extensions are adapted to wrap at least partially around a predetermined portion of the patient's anatomy. In one embodiment, the extensions are adapted to wrap around a portion of one of the pars and the superior articular process.

Additionally, or alternatively, the projections may be asymmetrical. Thus, in one embodiment, one projection has a shape and/or size that is different than another projection. For example, one projection may have a different thickness, contour, or length than the other projection. The asymmetric shape or size of the projections may be planned to contact, or avoid, a predetermined portion of the patient's anatomy. Additionally, the angle and orientation of each projection with respect to the distal end of the cannulae can be varied to match the anatomy of the patient, or to avoid a portion of the patient's anatomy.

In one embodiment of the present disclosure, the bore of the cannulae may facilitate and guide a drill bit, or any other suitable instrument to drill and tap a pilot hole in the cortical trajectory. After the pilot hole is created, the bore may further guide insertion of a fixation device, such as a cortical screw, into the pilot hole. In another embodiment of the present disclosure, the bore may be adapted to receive one or more inserts or guide wires such as the inserts.

In one embodiment, the bore is oriented in a cortical bone trajectory. Alternatively, the bore may be oriented in a pedicle screw trajectory. In another embodiment comprising a bore in each of the cannulae, the bores may be oriented to target different portions of the patient's anatomy. In still another embodiment, each bore of one or more cannulae is oriented in a cortical bone trajectory.

In one embodiment, the cannulae is manufactured out of, or the bore is lined with, a metal or metal alloy that is of sufficient strength and brittleness that breaking and/or flaking is avoided. Further, at least the interior surfaces of the bore may be formed of a material that can withstand the effects of high-speed drilling without damaging the bore or the cannulae or permitting material from the cannulae to become deposited in the drilling site, as well as facilitating re-use of the cannulae. The material of the cannulae may also be selected to withstand temperatures used to sterilize surgical instruments. In one embodiment, the guide comprises one or more of a polymeric material and a metallic material.

Referring now to FIGS. 22-29, patient-specific guides according to the present disclosure may also assist with placement of an iliosacral screw. The guide in this embodiment may be configured to mate with a secondary device such as a "tulip", which enables accurate placement of an iliosacral screw.

Methods for placing a screw using the guide of FIGS. 22-29 are also disclosed. In a preferred embodiment, the method comprises the steps of: creating a hole in the sacrum for placing the tulip, such as by using a chisel or burr; applying an external jig to constrain the iliosacral and ensure alignment with the placed tulip; advancing the screw from the lateral side of the ilium, through the ilium and across the sacroiliac joint; and, guiding the screw through the secondary tulip components and into the body of the sacrum. These steps are generally shown in relation to FIGS. 23A-24B and 26.

The guide cannula may be shaped to receive instruments or tools in a specific orientation or specific alignment, based in part on the patient's anatomy and/or presurgical planning. Alternatively, the guide cannula may comprise slots for receiving certain instruments or tools in a specific order, orientation or alignment. Examples of tools that are oriented by the shape/slot of the guide may include: a chisel/punch/burr, which makes the initial depression in the sacrum for placement of the tulip; a polyaxial or monoaxial tulip itself; and, an instrument that holds the tulip during insertion.

The guide shown in FIGS. 23A-24B may be individual guides for left and right side iliosacral fixation. A third component (not shown in FIGS. 23A-24B) may be used as a bridge to connect the left and right guides. This bridge may also be printed directly into the guide(s), as opposed to being removable.

Figure 27:
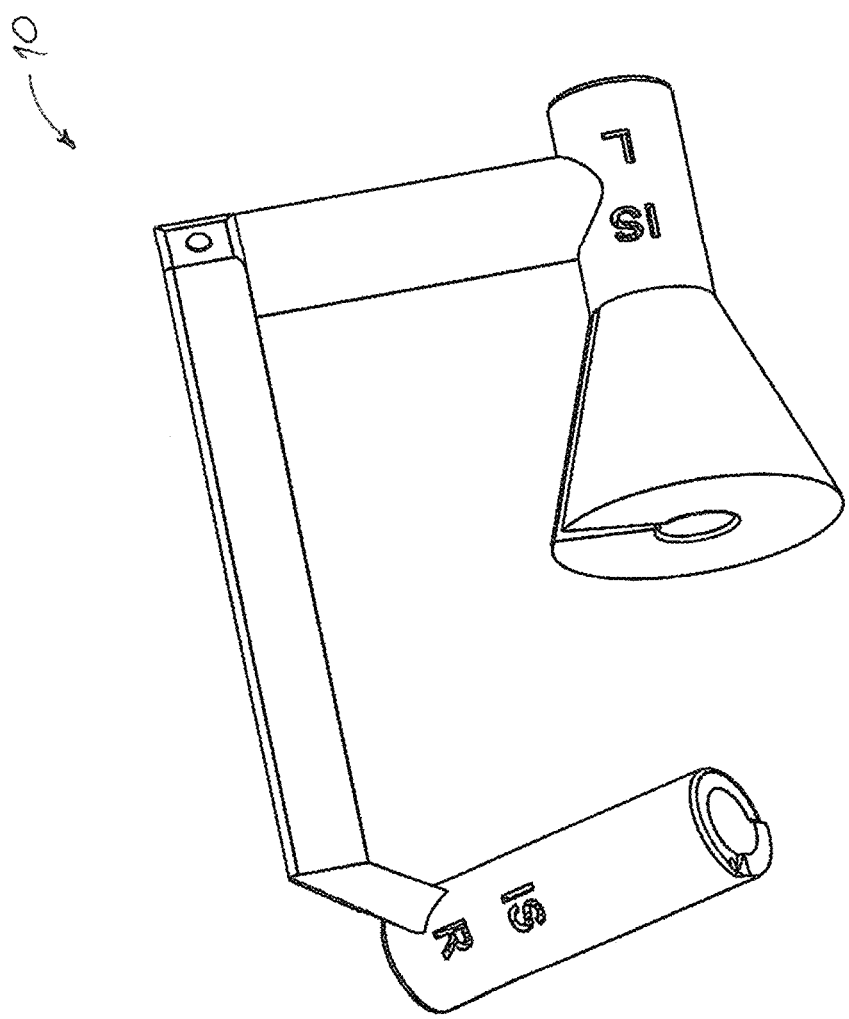
FIG. 27 is a perspective view of another patient-specific guide according to embodiments of the present disclosure.
Figure 28:
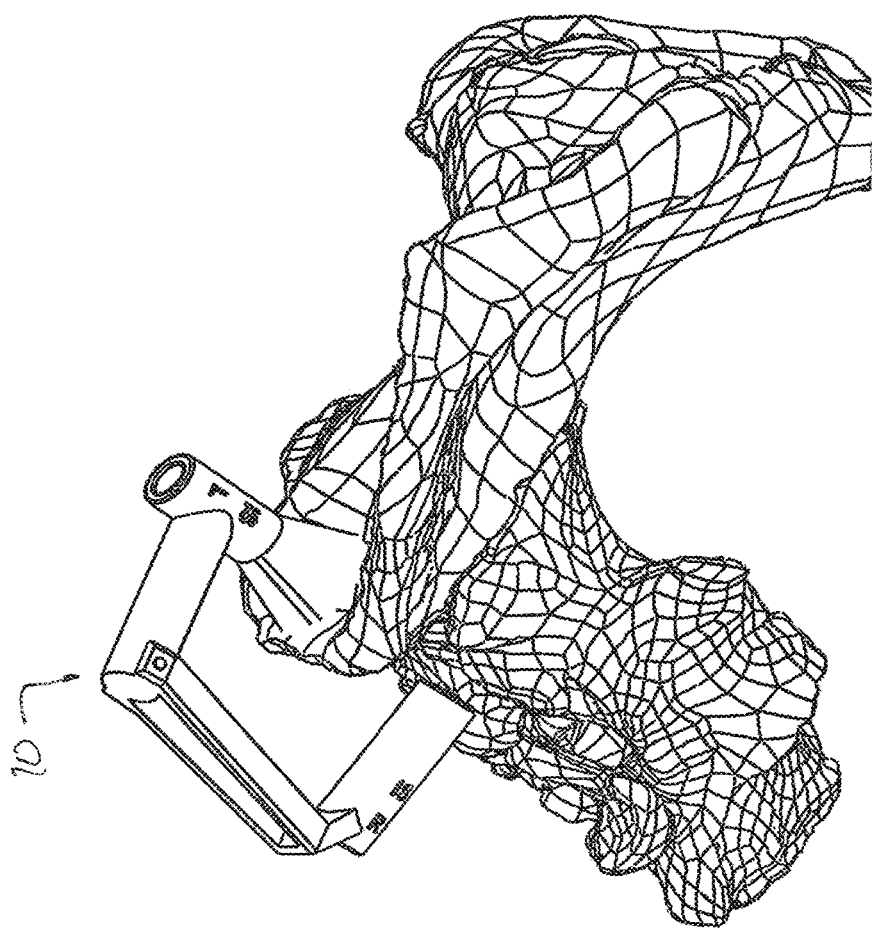
FIG. 28 is a perspective view of the guide of FIG. 27 shown against a patient's boney anatomy.
Figure 29:
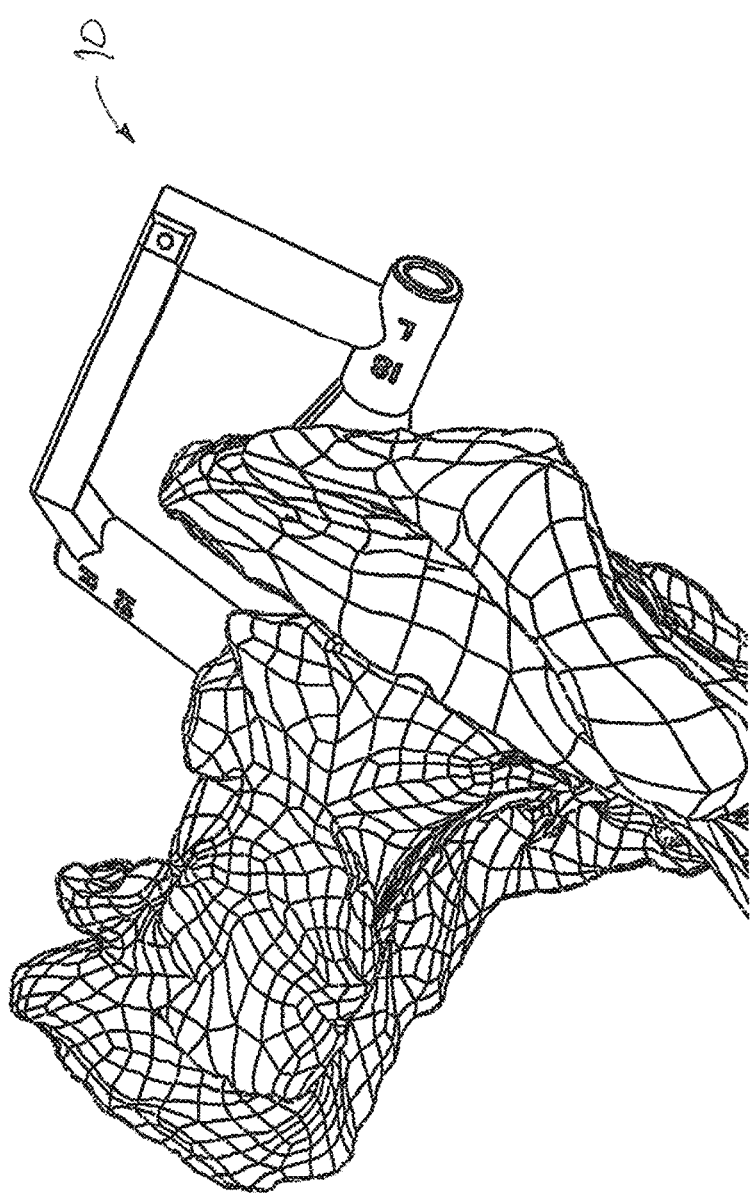
FIG. 29 is another perspective view of the guide of FIG. 27 shown against a patient's boney anatomy.

Turning now to FIGS. 27-29, a guide may be fabricated and supplied as a monolithic piece, as shown in FIG. 27. This guide may comprise a cannula similar to the one described above in relation to FIGS. 23A-23B. and a lateral guide cannula for placing the iliosacral screw through the guide. Preferably, the guide shown in FIG. 27 is a single piece and formed through any of the fabrication methods described above. Alternatively, the components in FIG. 27 may clip together at one of the joints. The guide may be fabricated by 3-D printing, although in certain embodiments only the tips of the cannula (i.e., the patient-contacting surfaces) are 3-D printed and attach to a reusable guide body.

The guide may include features adapted to be grasped or manipulated by a surgeon. Accordingly, gripping features may be formed on a portion of the guide. In one embodiment, the gripping features comprise protrusions. The protrusions may be of any shape or size selected to facilitate grasping of the guide in a surgical environment. In one embodiment, the protrusions are formed on a portion of the medial body. The protrusions may comprise ridges or bumps. In one embodiment, the protrusions comprise three generally parallel ridges formed on opposing sides of each portion of the medial body. However, it will be appreciated than any number of protrusions may be formed with the griping feature. Optionally, the gripping features of the medial body portion may be different than the gripping features of medial body portion. In this manner, a surgeon or other user can determine an orientation of the guide by feel without being required to look at the guide. In one embodiment, the gripping features are formed on a portion of the guide that extends beyond the patient's anatomy when the guide is in a predetermined position in contact with the patient's anatomy.

Although not illustrated in the appended drawing figures, the guide may further comprise attachment points formed in one or more of the medial body, the cannulae, and the legs. The attachment points are adapted to receive one or more secondary or tertiary cannulae. The cannulae may include a bore or a cutting slot to guide an instrument to target another portion of the patient's anatomy. In one embodiment, the cannulae are adapted to target one or more predetermined portions of the cervical spine (i.e., C1-S1 and ilium).

In one embodiment, the attachment points comprise slots to receive extensions of the cannulae. In one embodiment, the slots may also direct the path of a blade or other cutting instrument, or to receive a measurement aid or tool for facilitating the surgeon/user in identifying landmarks, surrounding boney anatomy, placement of implanted devices, or for surgical planning.

The guide may also include indicia to identify a sequence of use or portions of the patient's anatomy with which the guide is to be used. For example, the indicia indicate the guide is adapted for use with the L4 vertebrae level of a patient's spine. It will be appreciated by one of skill in the art, any number and type of indicia can be provided associated with different portions of the patient's anatomy. The indicia may also indicate a tool to be used, a direction of a cut to be performed, or a planned orientation or alignment of the guide. According to one embodiment, the guide may further comprise one or more indicia for identifying the guide with a particular patient.

The guide may be configured to receive one or more inserts. The insert in these embodiments generally comprises a proximal surface, a distal surface, projections extending from the distal surface, an aperture, and bores. The projections are adapted to fit directly to aspects of a patient's anatomy. More specifically, the projections are adapted to be positioned between a superior vertebrae and an inferior vertebrae within the intervertebral disc space. The shape of the projections is predetermined to match at least a portion of a curvature of the adjacent vertebrae and to facilitate the insertion of an implant with a predetermined size and shape into the intervertebral space.

The projections include a variety of patient-contacting surfaces which permit the insert to mate with portions of one or more vertebral bodies. The patient-contacting surfaces may be matched to substantially conform to a predetermined portion of the patient's anatomy by using the method described above. For example, the upper surfaces, lower surfaces, and interior surfaces of the respective projections may include patient specific contact surfaces. The distal surfaces of the insert may also include patient specific contact surfaces. The patient matched surfaces can be specific to any portion of the patient's anatomy, such as an anterior surface of a vertebral body and/or the sacrum, lamina, transverse processes, articular processes, spinous processes, etc. Thus, the patient specific surfaces of the projections and/or the distal surfaces facilitate registration of the insert to enable a correct fit and placement of the insert.

The patient specific surfaces may include any number of protrusions, depressions, and contours to substantially conform to the patient's anatomy. For example, the patient specific surfaces may comprise multiple portions that are adapted to contact two different planes formed by two distinct portions of the patient's anatomy. The patient specific surfaces are adapted to one or more of: align the insert in a predetermined position with respect to the patient's anatomy; hook around a portion of the patient's anatomy; prevent unintended or inadvertent movement of the insert during a surgical procedure; and displace soft tissue. In one embodiment, the patient specific surfaces comprise relatively thin extensions to displace soft tissue. By protruding at least partially around and substantially conforming to different portions of the patient's anatomy, the patient specific surfaces generally "hook" at least partially around (or to) the patient's anatomy. Thus, the surfaces may contact at least two different planes formed by distinct surfaces of the patient's anatomy. Accordingly, the insert is adapted to at least partially fit and substantially conform to predetermined portions of one or more vertebrae during the surgical procedure.

The patient specific surfaces help position the guide and keep it in position in a predetermined position and orientation. The combination of patient specific surfaces formed on various locations of the insert may decrease the possibility of improper placement of the interbody guide in relation to the patient's anatomy. The surgeon may also receive tactile feedback when advancing the insert between two adjacent vertebrae, such as a clip, snap, or vibration when the insert is properly aligned with, and received between, the vertebrae.

The projections may also be adapted to bias into a predetermined orientation with respect to the patient's anatomy. Accordingly, the material of the insert may be selected to allow a surgeon bend or stretch to hook around the patient's anatomy. In one embodiment, the insert or portions thereof, may be manufactured from a material that is at least partially flexible or deformable. In another embodiment, the insert is manufactured from a material with shape memory, such as Nitinol. In this manner, when properly aligned with the patient's anatomy as planned, the insert may be releasably retained in a predetermined alignment with respect to the patient's anatomy.

Additionally, or alternatively, the projections may be asymmetrical. Thus, in one embodiment, one projection has a shape and/or size that is different than the other projection. For example, one projection may have a different thickness, contour, or length than the other projection. The asymmetric shape or size of the projections may be planned to provide a predetermined correction to the patient's spine. Similarly, the asymmetric projections may be shaped for use with a defect of the patient's spine. Additionally, the angle and orientation of each projection with respect to the distal surface of the insert can be varied to match the anatomy of the patient, or to avoid a portion of the patient's anatomy. In one embodiment, the shape of the projections does not provide correction of deformities of the patient's anatomy. In another embodiment, the shape of the projections provides at least some correction of the patient's deformity.

Portions of the projections may have a tapered shape that can be used to distract the vertebrae. For example, the distal portion of each projection may comprise a full-radius or bullet-shaped nose for ease of insertion. Additionally, or alternatively, the distal portions may have a wedge shape.

A variety of patient specific tools can also be pre-operatively planned and manufactured according to the systems and methods described herein to aid in, by way of example but not limitation, verifying final sagittal and/or coronal alignment and/or confirm screw placement. The verification tools are unique to each patient and may contain patient matching surfaces, implant contacting surfaces, and/or capability to mate with a guide. The tools may offer visual or tactical feedback to the surgeon during or after a surgical procedure.

The tools may be adapted to verify coronal alignment during a surgical procedure. Said another way, the tools are preferably used by a surgeon to verify that planned correction of the spine was substantially generated.

Screws as described herein may be placed specifically to interconnect the tools to the patient's anatomy. Screws and other implants may also be patient-specific, and may be specific to a particular guide as well. For instance, in certain embodiments the screw may have at least a portion that is configured to be received within a bore of at least one cannula and only advance within the bore if it is the patient-specific screw corresponding to the patent-specific guide that is to be used with the particular screw. The bore may have surfaces that are complementary to the surfaces of the screw or other implant.

Other benefits achieved from the use of these patient-specific interbody guides of all embodiments of the present disclosure include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Additionally, the guides facility quicker bone removal and instrumentation of the patient's boney anatomy, decreasing surgical time and associated risk to the patient. The guides also increase the accuracy of procedures performed using the guide by providing patient matched surfaces to conform to a predetermined alignment of the guide with respect to the patient's anatomy. In this manner, the guides decrease the amount of fluoroscopy required to verify or correct the alignment of the guide, decreasing radian expose to medical staff as well as the patient.

Although the devices described above have been illustrated for use with certain guide screws and/or instruments, it is expressly understood that the devices may be used with a variety of other implantable and non-implantable apparatus, including by way of example, medial-to-laterally placed transpedicular screws (commonly referred to as cortical bone trajectory screws). Other screws and instruments may be used with the surgical devices described above without departing from the spirit of the disclosure and are considered to be within the scope of the appended claims.

A patient-specific apparatus may be provided that includes means for registration and validation by a computer-assisted technology, including the robotic, navigational, motion control or virtual reality systems described herein. The guide preferably comprises at least two distal surfaces that are patient-specific and designed to contact the patient in two unique locations. The guide preferably includes at least one registration marker for use in conjunction with robotic navigation and or autonomous/semi-autonomous systems described herein. In certain embodiments, the registration marker is removable. Alternatively, the registration marker may be embedded into the guide. By way of example, several guides may be placed along the patient's anatomical features, in distinct locations, and thereby provide the user with the ability to register various locations for surgical planning or, in certain embodiments, robot-assisted navigation.

Several of the patient-specific guides described herein may be used with various orientation or registration markers for identification by a robot. Certain guides may comprise an embedded chip, circuit or equivalent medium with presurgical planning information, which may be read by a machine and deliver specific instructions to a robotic surgical device, for example. In this manner, a surgeon may attach a patient-specific apparatus (such as the one shown in FIG. 16) to each level of the patient's spine that is impacted by a particular surgical procedure, and thereby provide markers for registration and orientation without having to rescan the patient throughout the surgery. In turn, the robotically guided surgical device may view the patient through the markers and align instrumentation controlled by the robotic equipment. This alignment may be achieved by any one of a combination of guides/markers/patient-specific orientation guides.

In another embodiment, the patient-specific guides described herein comprises a locating feature for a robot or other autonomous device to align the guide to a vertebra in space, for example. With multiple locating guides placed on a patient's vertebra, a robot can drill into the vertebra, affix an orientation tool, and/or orient vertebra relative to each other to meet pre-surgically planned spinal alignment. Pre-surgically planned spinal alignment may also be matched to one or more pre-bent rods, minimizing surgical time. In other embodiments, the robot or other autonomous device may be configured to perform an osteotomy with known locations of vertebra relative to each other.

Referring now to FIGS. 30A-30B, further illustrations of a cutting guide 110 are provided. According to one embodiment, the cutting guide 110 comprises a plurality of patient-specific contacting surfaces 114 about at least one surface of the cutting guide and an alignment channel 116. The contacting surfaces may comprise portions 114A, 114B adapted to hook at least partially around portions of the patient's anatomy. In one embodiment, the contacting surfaces 114 are adapted to conform to cut surface generated by removal of a portion of the patient's anatomy. The cutting guide further comprises, in a preferred embodiment, a patient-specific slot or "track" 120 for facilitating insertion of a cutting instrument (as shown in FIGS. 31-32) and controlling the depth of insertion for that instrument to prevent unnecessary cutting of the underlying surface during a particular surgical procedure by further providing one or more instrument contacting surfaces 122.

According to the embodiment shown in connection with FIGS. 30A-32, the cutting guide 110 may be provided for a laminectomy. According to other embodiments, the patient-specific guide may be fabricated for use in performing a corpectomy, a Pedicle Subtraction Osteotomy (PSO), a Smith-Peterson Osteotomy (SPO), a Vertebral Column Resection (VCR), or an Asymmetric Osteotomy (in either the sagittal or coronal plane), among others.

These patient-specific cutting guide 110 may be fabricated from patient anatomical data, and may assist in performing complex procedures with greater certainty in their outcomes. For example, certain osteotomies, specifically PSO and SPO, require a great deal of surgical skill and are often time consuming. This is due in part to the intimate relationship of the vascular and neural elements to the boney structures, which create navigational challenges for a surgeon to safely and efficiently resect the bone during one of these procedures. This is especially true from a posterior approach. By using a patient-specific guide, a surgeon may confirm positioning and alignment of the cutting trajectory and path prior to initiating the procedure, and in furtherance of the disclosure provided above in relation to FIGS. 30A-32, may also provide a degree of depth control essential for avoiding contact with vascular and neural elements.

In one embodiment, the cutting tool 140 associated with the cutting guide 110 shown in FIGS. 30A-32 is typical of the type of tools currently used in surgical procedures today. According to another embodiment, a specialty cutting bur or tip 142 may be included with the instrument to facilitate further control of the location and depth of the instrument, as described in further detail below. For example, as shown in FIGS. 31A-31C, the cutting portion of the instrument may have a protrusion 144 that prevents greater insertion of the instrument 140 into the cutting guide 110 than required for the patient-specific procedure. In one embodiment, the position of the protrusion 144 on the cutting tip 142 may be adjusted by a user. The protrusion 144 may be of any form adapted to interact with contact surfaces 122 of the slot 120 to control the use of the cutting tool 140. In one embodiment, the protrusion 144 is a bearing. In another embodiment, the protrusion is a track ball. In still another embodiment, the protrusion is generally disc-shaped.

Figure 32A:
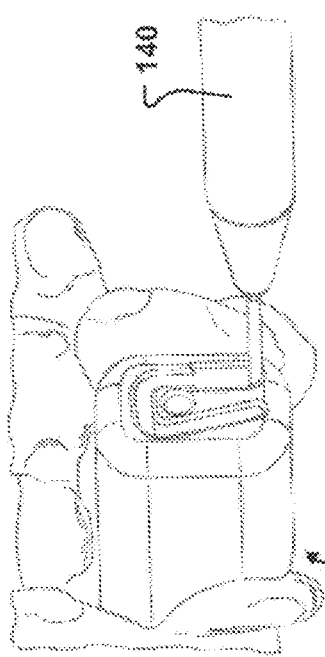
FIGS. 32A-32B are perspective views of the cutting tool of the embodiment shown in FIG. 31A depicted with the cutting guide of FIG. 30A.
Figure 32B:
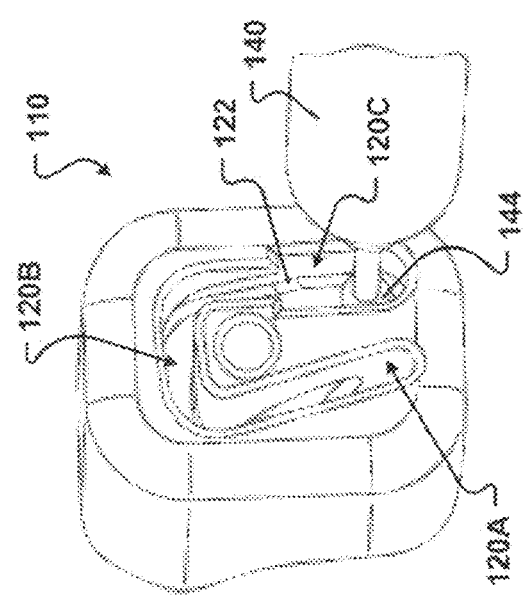

As shown in greater detail in FIGS. 32A-32B, the protrusion 144 may be inserted into a first portion 120C of the "track" 120 of the cutting guide 110. Second or third deeper portions 120A, 120B of the "track" of a cutting guide (through which the cutting surface is permitted to travel), may prevent insertion or withdrawal of the protrusion 144, thereby insuring proper depth of the cutting instrument. Further geometrical configurations other than those shown in FIGS. 32A-32B may be provided that allow the protrusion 144 to move horizontally with respect to the top surface of the cutting guide, and in some instances laterally and downwardly into the track 120 of the cutting guide. In this embodiment, the cutting instrument 140 would therefore be permitted to move at a certain depth about a patient's anatomy in a certain location of the "track" 120 of the cutting guide, but achieve a greater depth at yet other locations about the "track" 120 of the cutting guide 110. Thus, the depth permitted with respect to the instrument 140 relative to the cutting guide 110 may be variable about the "track" 120 of the cutting guide.

It will be appreciated by one of skill in the art that the size and location of the surfaces 122 may be altered as desired. Accordingly, in other embodiments of the present disclosure, the instrument 140 may be inserted and removed from different portions of the track 120, or from two or more portions of the track. Further, in one embodiment, the track 120 and the instrument 140 include protrusions that interact to permit the tool to be inserted in only a first portion of the track, for example portion 120C, and removed from only a second portion of the track, such as portions 120A or 120B.

Other benefits achieved from the use of these patient-specific cutting guides include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Referring now to FIGS. 33A-33J, a guide sleeve 210 of another embodiment of the present disclosure is described. The sleeve 210 is adapted for use in a posterior osteotomy, also known as a Smith-Petersen Osteotomy (SPO) or a "ponte osteotomy" procedure. As will be appreciated by one of skill in the art, during a posterior osteotomy, a portion of bone is removed from the back of the patient's spine. Portions of the posterior ligament and facet joints may also be removed from targeted portions of the patient's spine. The osteotomy may be performed at one or multiple locations along the spine to correct the alignment of the patient's spine.

In one embodiment of the present disclosure, a surgical guide 246, guide sleeve 248 and drilling insert or sleeve 249 assembly according to an embodiment of the present disclosure is positioned proximate to a targeted portion of the patient's anatomy. The drill sleeve 249 (placed through the patient-matched guide sleeves 248 and into the bone at opposing, dissimilar angles) provides additional fixation of the guide 246 to the vertebra V.

The guide 246 is used to introduce a bore (not illustrated) into the pedicle for the guide sleeve 210. The trajectory of the bore is specifically planned and controlled by sleeve 248 for the drilling sleeve 249. The placement of bore is selected in such a way that neural elements are protected from the tool 247 inserted through the drilling sleeve 249. The trajectory of the bore is selected to be a predetermined distance away from the neural elements so that the tool 247 is a safe distance away. In one embodiment, the bore is at least 0.25 mm away from the patient's neural elements. However, it will be appreciated that any predetermined distance separating the bore from neural elements may be used. In another embodiment, the distance is from about 0.1 mm to about 3 mm.

Referring now to FIGS. 33C-33G, once the pedicle is cannulated, the surgical guide 246 may be removed from the vertebrae V. A guide sleeve 210 is inserted to a controlled depth within the bore. The cutting tool 240 is inserted into a cannula 225 of the sleeve 210 and activated. The tool includes a surface 242 that cuts from the interior to the exterior of the pedicle. In one embodiment of the present disclosure, the guide sleeve 210 includes an aperture 218 for the cutting surface 242. The aperture 218 may be spaced from the distal end of the guide sleeve 210 by a predetermined amount to control the depth of the cut. In another embodiment, the aperture is positioned at the distal end of the sleeve 210.

The cutting surface 242 may be mechanically or electrically actuated. The cutting surface 242 may comprise a reciprocating or a rotating blade, or any other type of cutting tool. In one embodiment, the orientation or length of the cutting surface 242 may be altered by the surgeon during the surgical procedure. Optionally, in another embodiment of the present disclosure, the tool is operable to ablate portions of the pedicle to complete the cut. For example, the tool may comprise a laser adapted to burn through portions of the pedicle from within the bore. In another embodiment, the tool may comprise a heated surface to burn or otherwise remove portion of bone or tissue. Once the cut has been made, the posterior column of the vertebra can be removed.

Figure 33A:
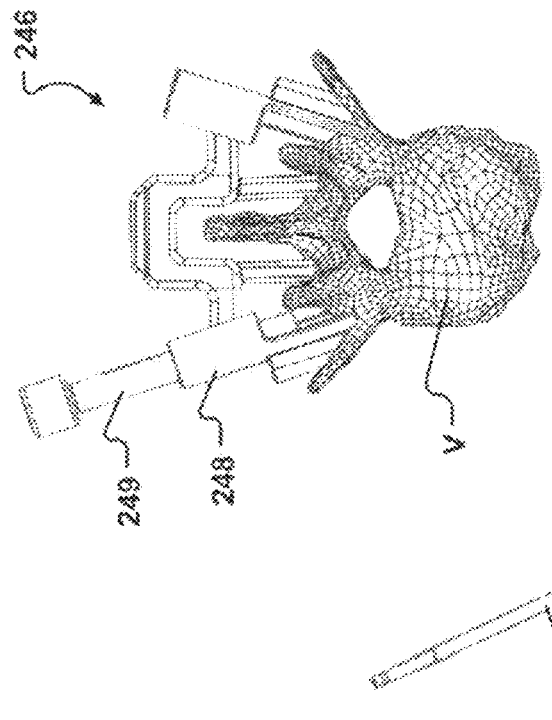
FIG. 33A is a front elevation view of a guide of another embodiment of the present disclosure positioned against a vertebral body.
Figure 33B:
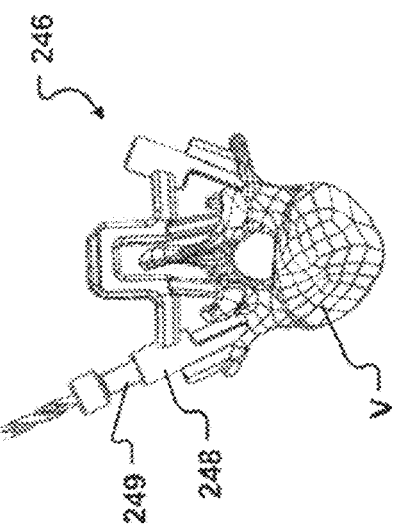
FIG. 33B is another front elevation view illustrating a boring instrument of an embodiment of the present disclosure inserted in a cannula of the guide of FIG. 33A.

Referring now to FIGS. 33H-33I, a guide sleeve 210 of another embodiment of the present disclosure is described. In this embodiment of the present disclosure, a surgical guide 246 and guide sleeve 248 are positioned proximate to a targeted portion of the patient's anatomy. The drill sleeve 249, instead of being placed through the patient-matched guide sleeves 248, as described in FIGS. 33A-33B, is selectively coupled and/or attached to tool 247. When the tool 247 with the attached drilling sleeve 249 is inserted through guide sleeve 248, the trajectory is planned and controlled as described above in FIGS. 33A-33B. The trajectory of the guide sleeve 248 and drill sleeve 249 are also selected to be a predetermined distance away from the neural elements so that the tool 247, once coupled to the drill sleeve 249 and fully inserted into guide sleeve 248, is a safe distance away from neural elements and prohibited from over-penetrating the patient's boney anatomy. In some embodiments this may be accomplished via the placement of stopping mechanisms 250 on the tool 247, which control the movement, i.e. depth, of the tool 247 while affixed to the drilling sleeve 249. In preferred embodiments, these stopping mechanisms 250 prevent the tool 247, instrument or device from advancing beyond a predetermined distance within the guide sleeve 248, thereby providing a hard stop. In embodiments, the user may select the precise location of the drill sleeve 249 to effectively select the depth the tool 247 is permitted to advance through the guide sleeve 248. These embodiments may also facilitate expedited surgical procedures because the user is able to position the sleeve 249 onto the tool in the desired position and location, and therefore moving and registering the drill sleeve 249 into each guide sleeve 248 or guide 246 is no longer necessary.

Referring now to FIGS. 34A-34D, an embodiment of a guide 310 comprising a frame 330 is illustrated. The guide 310 is adapted for use in a posterior osteotomy, although other procedures are contemplated. The frame 330 may have a patient-specific shape. For example, the frame may be adapted to flex or snap into a position in contact with a transverse process T or other portion of the patient's anatomy. Alternatively, the frame 330 may be designed to be used in surgical procedures for any patient.

In use, the frame 330 is interconnected to fixation devices 334 positioned in predetermined portions of the patient's anatomy, such as the patient's vertebrae, V. In one embodiment, as illustrated, the vertebrae V include an inferior vertebra VI, a medial vertebra VM, and a superior vertebra VS. The fixation devices 334 may be pedicle screws. Optionally, the fixtures 334 may comprise a porous material.

Although two fixation devices 334 in each of the inferior and superior vertebra VI, VS are illustrated in use with the frame 330 of the embodiments of FIG. 34, it will be appreciated that any number, including fewer screws, may be used with the frame. The size and shape of the frame 330 may be selected to only permit the frame to be interconnected to the screws when the frame is in a pre-planned orientation. For example, the embodiment of the frame 330 illustrated in FIG. 34A has a shape that only permits the frame to be interconnected to the four pedicle screws 334 when the frame is in one predetermined orientation. Accordingly, the shape of the frame is adapted to ensure proper alignment of the frame and the guide, limiting the possibility of misuse of the frame and guide.

The pedicle screws 334 or other fixation devices may be placed in the vertebrae using any tool or guide. In one embodiment, the fixation devices are placed in bores formed in the patient's vertebrae formed by a drill apparatus. Pre-existing pedicle screws from a previous surgery may be used with the frame. One or more of the pedicle screws may also be positioned using a pedicle screw guide of an embodiment of the present disclosure, for example, the guide 246 described above. Other embodiments of pedicle screw guides are described in the Applicant's U.S. Pat. No. 9,198,678 which is incorporated herein in its entirety.

The frame 330 serves multiple purposes. For example, the frame may retract soft tissue in the surgical area. Further, reference points or indicia may be provided on the frame 330 for docking the osteotomy guide 310. The indicia may indicate a planned orientation or alignment of the guide. The shape of the frame 330 may only permit docking of the guide when the guide 310 is in a pre-planned orientation with respect to the targeted vertebrae.

The frame 330 may also be used to distract the vertebrae in a target area of the patient's spine by a predetermined amount. The distraction provided by the frame may ensure a cut is formed at a predetermined angle. The distraction may also be necessary to provide access to a predetermined portion of the patient's anatomy. Once interconnected to the pedicle screws 334, the frame 330 may also prevent unintended movement of the vertebrae during the surgical procedure. The frame may also be planned such that it increases the distraction of the construct to provide the surgeon with a larger window through which the surgery can be completed. In this embodiment the frame connects the superior vertebra VS (above the osteotomy location of the medial vertebra VM) to the inferior vertebra VI (below the osteotomy location). In one embodiment, the frame is positioned lateral to the pedicles so that the posterior anatomy of the medial vertebra VM is substantially unobstructed by the frame 330. It will be appreciated by one of skill in the art that the frame may be sized to span any number of vertebra.

Once the frame 330 is interconnected to the pedicle screws, the guide 310 is interconnected to the frame. The guide 310 is presurgically planned to align on the frame 330 with targeted portions of the medial vertebrae VM in a patient-specific location so that cuts are made accurately.

Figure 34C:
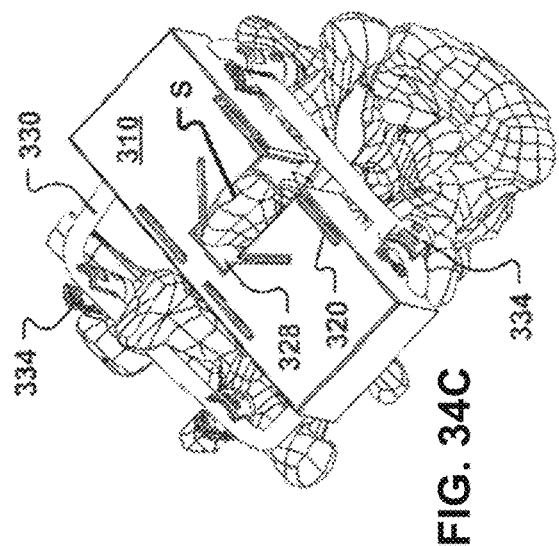
FIG. 34C is a perspective view of the guide and the frame of FIG. 34B.
Figure 34D:
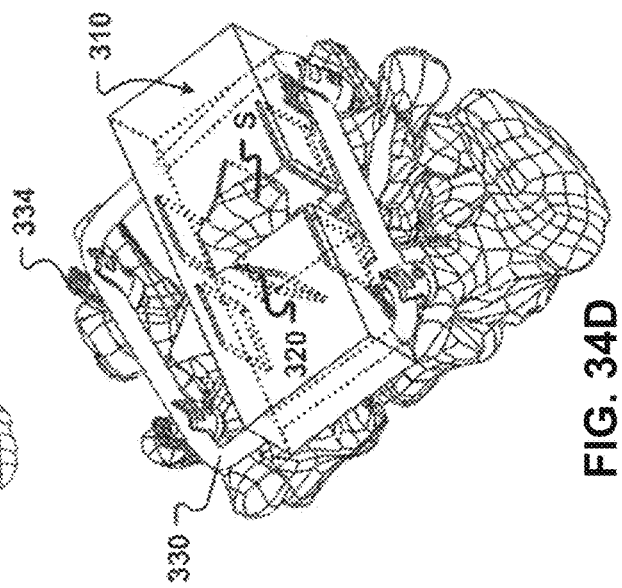
FIG. 34D is another perspective view of the guide and the frame of FIG. 34B including hidden lines showing the structure of slots formed in the guide.
Figure 34A:
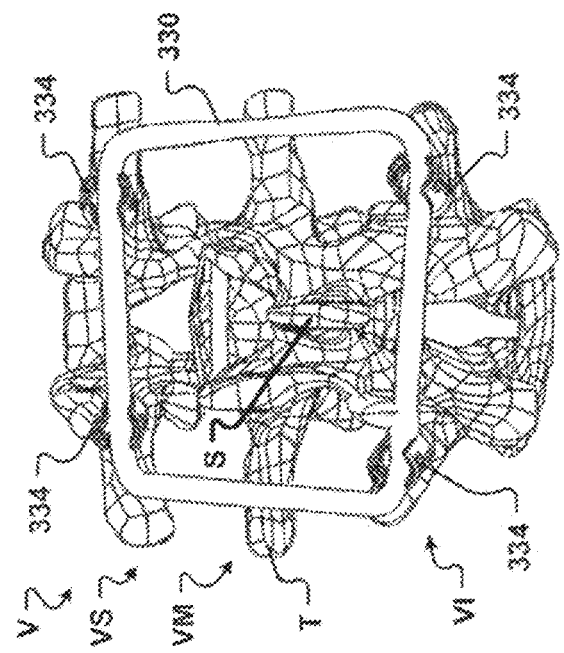
FIG. 34A is a front elevation view of a frame of an embodiment of the present disclosure interconnected to a portion of a patient's spine.
Figure 34B:
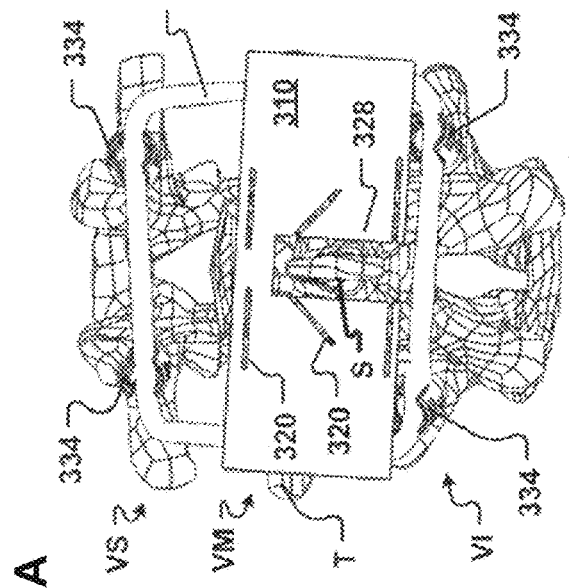
FIG. 34B is a front elevation view of a guide of another embodiment of the present disclosure interconnected to the frame of FIG. 34A.

Although the embodiment of the guide 310 illustrated in FIGS. 34B-34D is shown as one piece, it will be appreciated that in other embodiments the guide could include multiple pieces or a series of cutting guides that are placed in a specific order to generate a series of planned cuts. In embodiments of guides comprising multiple pieces, each piece of the guide may be keyed to interconnect in a specific order and location to other pieces of the guide. In one embodiment, the guide 310 does not contact the patient's anatomy. Said another way, the guide 310 is adapted to float over a surgical area when the guide is interconnected to the frame 330. In another embodiment, at least a portion of the guide 310 is adapted to contact the patient's anatomy.

The guide may include slots 320 and apertures 328. The aperture 328 may be positioned to prevent contact with portions of the patient's anatomy. For example, the guide 310 of the embodiment illustrated in FIGS. 34B-34D includes and aperture 328 to at least partially receive the spinous process S of the medial vertebra VM. The aperture 328 and surfaces of the guide proximate to the patient's anatomy may include patient specific contours adapted to substantially conform to predetermined portions of the patient's anatomy. In this manner, the alignment of the guide with a planned portion of the patient's anatomy may be enhanced. The patient specific contact contours may also improve the stability of the guide 310 during the procedure.

The slots 320 are positioned and have sizes to guide tools used during the surgical procedure, similar to the slots 20, 120 of the guides 10, 110 described above. The slots 320 may have shapes and be positioned at a variety of angles to guide tools, including cutting tools. Each slot 320 may have a unique size and orientation. Thus, slots may be adapted to receive different tools, or only one specific tool. Features, such as protrusions, may be formed in the slot and interact with features of the tools to control the depth of insertion of the tool, direction of use of the tool, and insertion and removal points of the tool. Inserts, similar to the insert 24 described above, may be formed to be positioned in the slots 320 to prevent damage to the slots or to ensure proper use of tools during the procedure.

Although not illustrated, it will be appreciated that one or more cannula or bores may be associated with the guide 310. For example, in one embodiment, the guide includes a bore the same as, or similar to, the alignment channels 16, 116 described above.

Referring now to FIGS. 35A-35G, still another embodiment of a guide 410 of the present disclosure is illustrated. The guide 410 is adapted for use in pedicle subtraction osteotomies (PSO) and asymmetrical pedicle subtraction osteotomies (APSO) for a single vertebral level. The size and shape of the guide may be selected to fit the guide across the surface of the vertebra V.

The guide 410 may comprise one piece adapted to target one portion of the vertebra. Alternatively, the guide may be formed in two or more pieces to target a variety of locations of the vertebra. The pieces can guide an ordered sequence of cuts in the vertebra. In one embodiment, the pieces may be interconnected in sequence during the surgical procedure to form the guide 410.

In one embodiment, the guide 410 may fit directly to the posterior aspects of a patient's anatomy, such as lamina, transverse processes, articular processes, spinous processes, etc. Accordingly, a variety of patient matching surfaces 414 may be provided on the guide 410. Additionally, or alternatively, the guide 410 could also fit to a surface of the spine that has previously been cut. In one embodiment, the previous cut may be performed using an initial guide of the present disclosure. The initial guide is adapted to guide a cutting tool used to generate a surface of the vertebrae. The guide 410 may be designed to fit to the surface generated using the initial guide. Additional cuts in the altered vertebrae can then be performed using the guide 410. Alternatively, the guide 410 may be interconnected to any frame described herein, including frames 330, 730.

The guide 410 includes slots 420 to guide surgical tools, including cutting tools such as routers, burrs, and other similar device, along a track to aid in removal of pedicles. The slots 420 may be the same as, or similar to, the slots of guides 10, 110 described above. The slots have a size and orientation selected to constrain cutting tools to presurgically planned entry points and angles of cuts for the procedure. As will be appreciated, the slots 420 may be oriented in a plane transverse to the proximal surface portion of the guide 410. The slots can be planned to guide tools to make cuts that are substantially linear, concave, convex, curvilinear, or "chevron" shaped. Further, as described above, the slots 410 may receive sleeves 24 and can include stops and keys to guide or restrict movement of the surgical tool.

Optionally, the guide 410 includes an alignment channel or cannula 416. The cannula 416 is adapted to guide a fixture tool or anchor, such as fixture 434, into the vertebra. It will be appreciated that the cannula 416 may be positioned in a variety of locations on the guide. Further, more than one cannula can be provided.

Figure 35D:
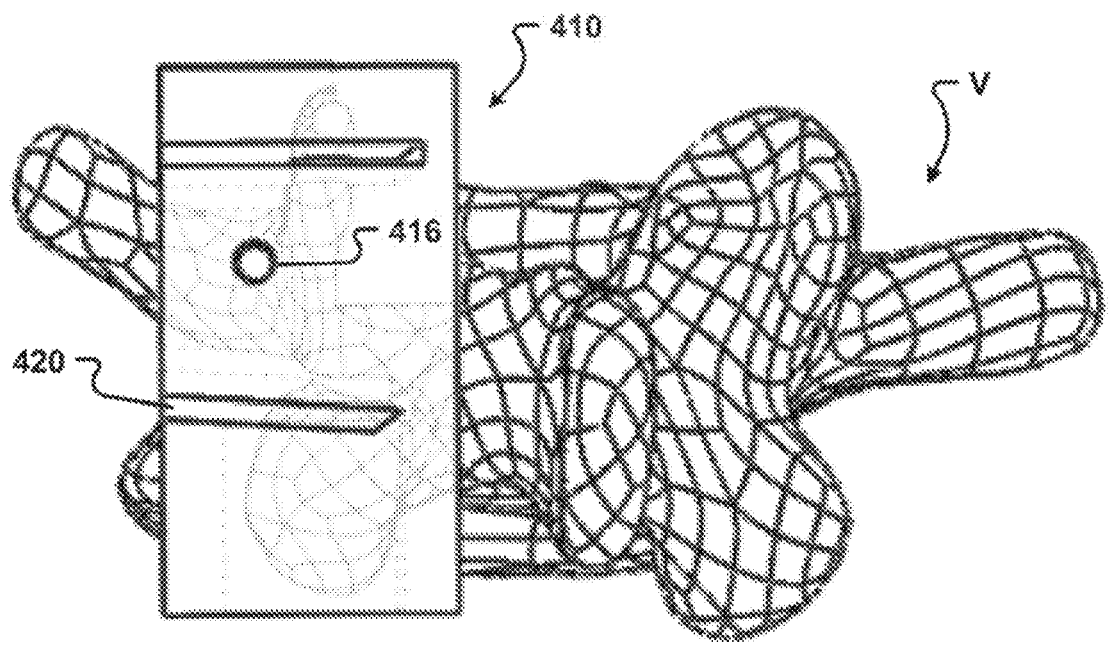
FIGS. 35D-35E are a front elevation view and a perspective view of the guide of FIG. 35A positioned against a vertebral body and including hidden lines showing the structure of slots formed in the guide.
Figure 35E:
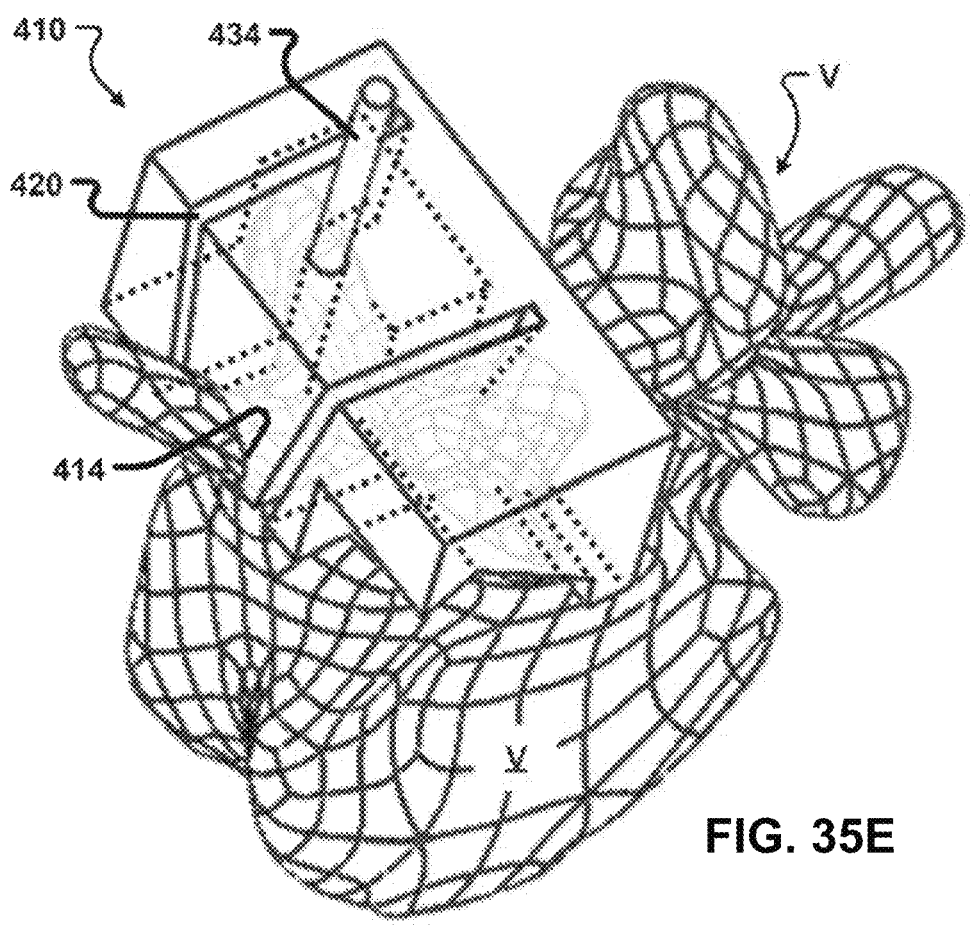
Figure 36A:
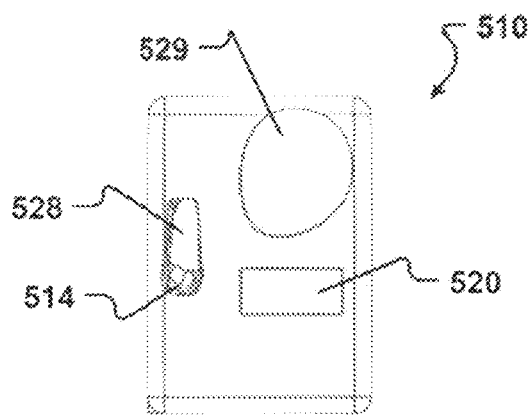
FIG. 36A is a front elevation view of still another guide of an embodiment of the present disclosure.
Figure 36B:
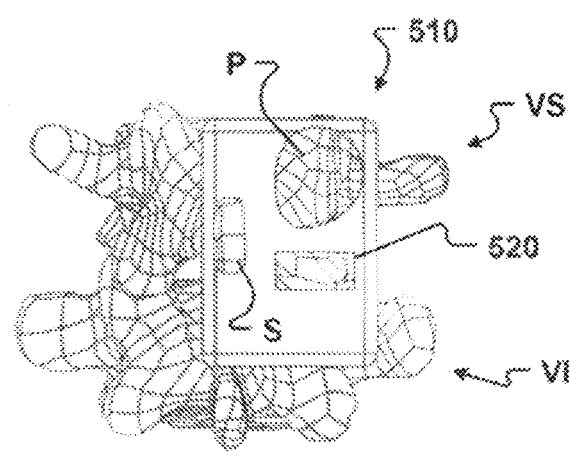
FIG. 36B is another front elevation view of the guide of FIG. 36A positioned against a vertebral body.
Figure 36C:
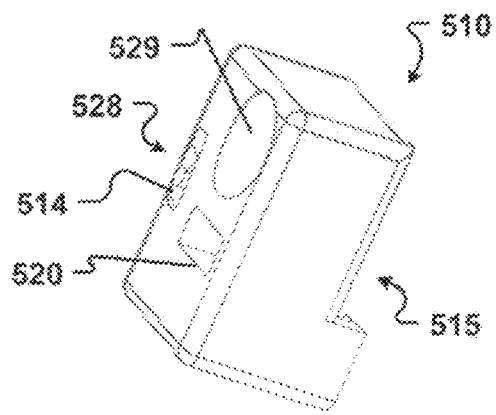
FIG. 36C is a side perspective view of the guide of FIG. 36A.
Figure 36D:
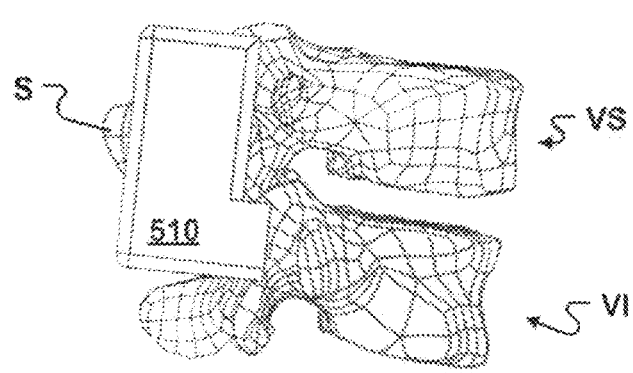
FIG. 36D is a side view of the guide of FIG. 36A positioned against the vertebral body.
Figure 36E:
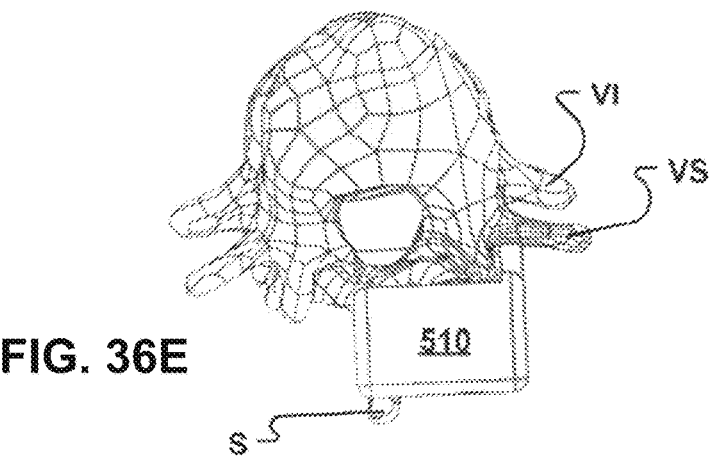
FIG. 36E is a top view of the guide of FIG. 36A positioned against the vertebral body.

In one embodiment, as illustrated in FIGS. 35E-35G, the guide 410 is anchored to the vertebrae by an anchor 434. After the cuts 450 (illustrated in FIG. 35G) have been completed in the pedicle of the vertebrae V, the entire cut portion of the pedicle can be removed along with the guide 410 by pulling the anchor 434 away from the vertebrae V.

FIGS. 36A-36E illustrate another embodiment of a guide 510 of the present disclosure. In one embodiment, the guide 510 is adapted for use in PSO and APSO procedures. The guide is sized to partially span adjacent superior VS and inferior VI vertebrae. Similar to the guide 410, guide 510 includes patient specific contact surfaces 514 adapted to substantially conform to the patient's anatomy. For example, in one embodiment, the distal surface 515 of the guide includes a plurality of patient specific contours. At least one portion of the distal surface 515 may be adapted to contact a cut surface formed by removal of a portion of the patient's anatomy.

A number of apertures may be formed through the guide to target, avoid, or align with, predetermined portions of the patient's anatomy. For example, an aperture 528 may be formed through the guide 510 with a shape selected to allow the spinous process S to at least partially pass through the guide. Patient specific surfaces 514 may be formed within the aperture 528.

The guide may further include a pedicle aperture 529 with a pre-planned shape to at least partially receive the pedicle P of the patient. The pedicle aperture 529 may also include interior surfaces that are patient specific. A surgeon may insert cutting tools into the aperture 529 to remove portions of the pedicle P. The pedicle aperture may be shaped to prevent over insertion of a tool into the vertebrae. Further, keys may be formed around the aperture 529. In conjunction with a protrusion formed on the tool, such as the protrusion 144 described above, the keys may control or alter the depth of insertion of the tool as the surgeon move the tool around the aperture 529.

The guide 510 may also include a cutting track 520. The track 520 is similar to slots 20, 120, 320 described above and may receive a guide sleeve the same as, or similar to, sleeve 24. In one embodiment of the present disclosure, the cutting track 520 is adapted to target facet capsules of each of the superior VS and inferior VI vertebrae. The surgeon may use the cutting track 520 to separate the adjacent facet capsules of the adjacent vertebrae. As will be appreciated, other cutting tracks or cutting slots may be provided on the guide to control other planned cuts.

Although not illustrated, the guide 510 may include a cannula similar to cannula 16, 416 describe above. A fixture implanted in the vertebrae may be received in the cannula to at least temporarily interconnect the guide 510 to the vertebrae. Optionally, the cannula may be adapted to guide an instrument, including a boring instrument or cutting tool 240.

Referring now to FIGS. 37A-37E, still another embodiment of a guide 610 of the present disclosure is illustrated. The guide 610 is similar to guide 510 and includes a distal surface 615 that may include patient specific contact surfaces. At least one of the contact surfaces may be adapted to substantially conform to an unaltered portion of the patient's anatomy. Another portion of the distal surface 615 may be adapted to substantially conform to a portion of the patient's anatomy altered, for example, by a cut. An aperture 628 adapted to at least partially receive the spinous process S may be provided. The aperture 628 may include patient specific surface 614.

Figure 37A:
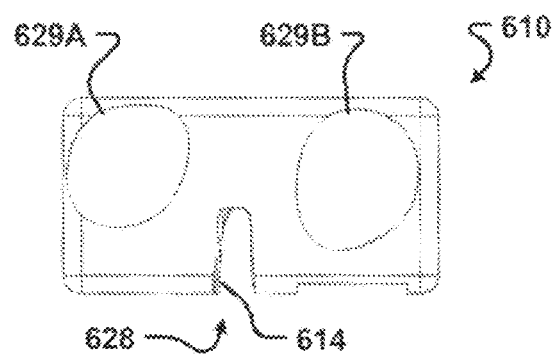
FIG. 37A is a front elevation view of yet another guide of an embodiment of the present disclosure.
Figure 37B:
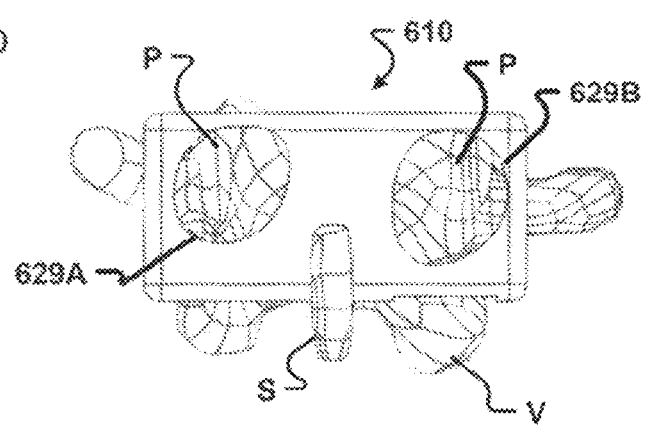
FIG. 37B is another front elevation view of the guide of FIG. 37A positioned against a vertebral body.
Figure 37C:
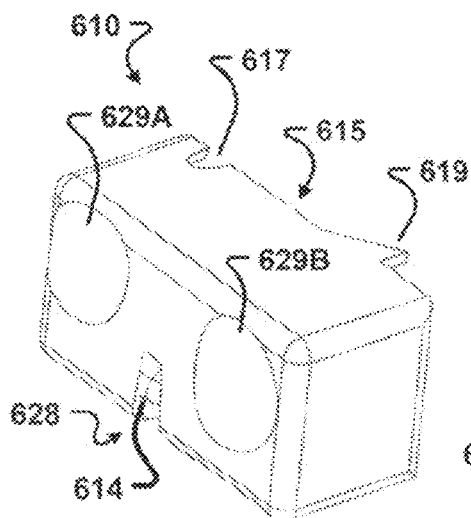
FIG. 37C is a side perspective view of the guide of FIG. 37A.
Figure 37D:
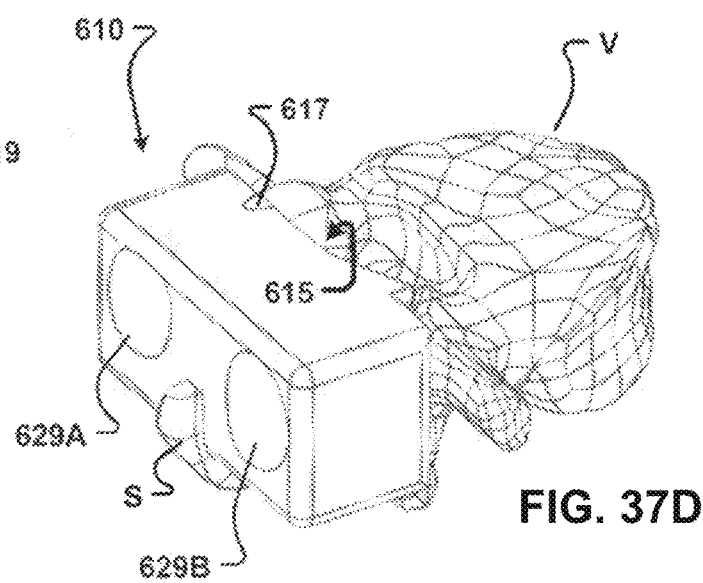
FIG. 37D is another side perspective view of the guide of FIG. 37A positioned against the vertebral body.
Figure 37E:
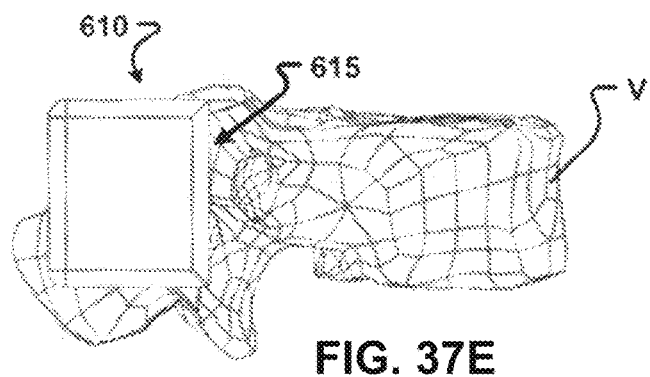
FIG. 37E is a side view of the guide of FIG. 37A positioned against the vertebral body.

The guide 610 is adapted to target each pedicle P of a vertebrae V. Accordingly, the guide includes two pedicle apertures 629. The apertures are the same as, or similar to, the pedicle aperture 529 of the guide 510 describes above. In one embodiment, each pedicle aperture 629A, 629B may have a unique shape specific to the patient's anatomy. Optionally, the guide 610 may have a thickness determined such that the pedicles P do not project beyond a plane formed by a proximal surface as illustrated in FIGS. 37D, 37E.

Voids 617 may also be formed in portions of the guide to align the guide with the vertebrae V. The voids may be in various positions. Further, the voids 617 may extend partially or completely through the guide 610. In addition, a protrusion 619 may extend from the distal surface 615 of the guide. The protrusion may be adapted to fit to a selected portion of the posterior of the vertebrae. Optionally, the void 617 or the protrusion 619 may at least partially hook around a portion of the patient's anatomy. In this manner, the void 617 and protrusion 619 contact distinct portions of the patient's anatomy compared to other portions of the distal surface 615. The void and protrusion thus provide references to indicate when the guide 610 is positioned in a predetermined position in relation to the patient's anatomy. Said another way, the void 617 or protrusion 619 will prevent the guide 610 from seating properly when the guide is in an improper position. Thus, the guide will not be stable, providing tactile feedback to the user that the guide is not in the correct position. In one embodiment, the protrusion 619 is adapted to fit the guide to a portion of a transverse process or a lamina. Each void 617 or protrusion 619 may further include patient specific surfaces.

Figure 38A:
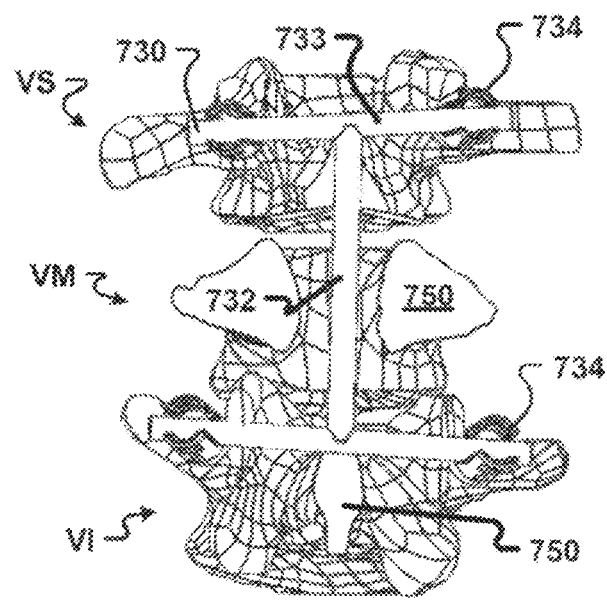
FIG. 38A is a front elevation view of a frame of an embodiment of the present disclosure interconnected to a portion of a patient's spine.
Figure 38B:
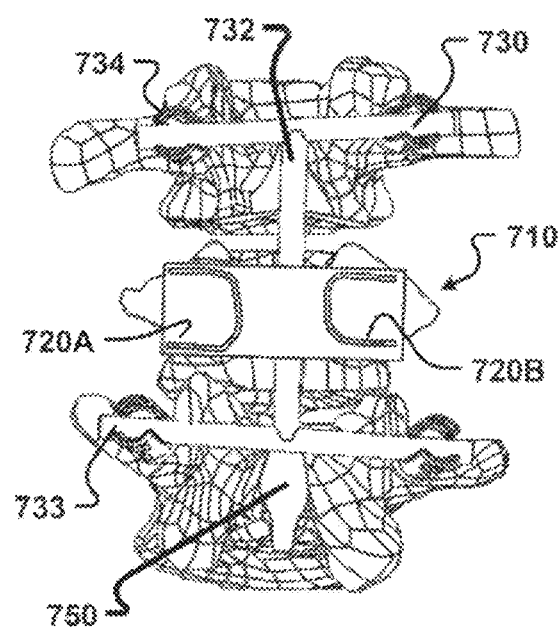
FIGS. 38B-38C are an elevation view and a perspective view of another guide of an embodiment of the present disclosure interconnected to the frame of FIG. 38A.
Figure 38C:
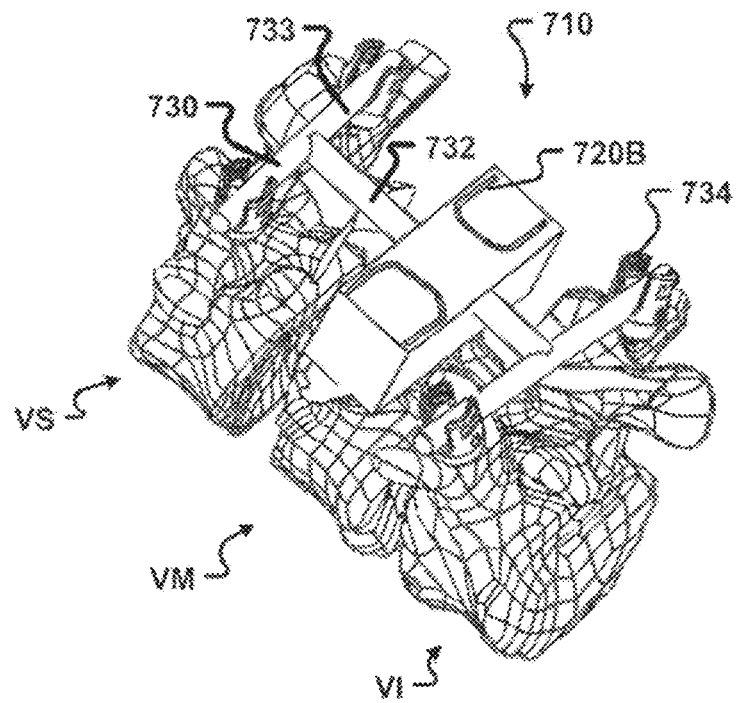
Figure 40A:
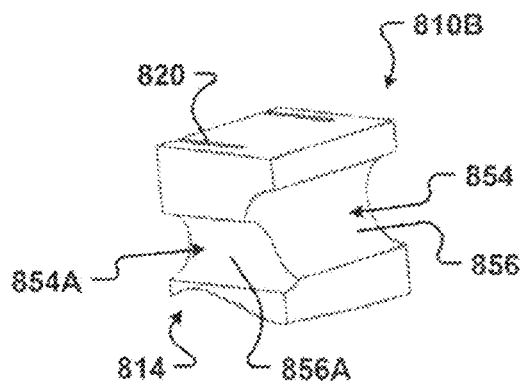
FIGS. 40A-40E are perspective views of a guide of yet another embodiment of the present disclosure with FIGS. 40C-40D illustrating the guide positioned against a vertebral body that has been cut to remove portions of the vertebrae and FIG. 40E showing the guide positioned against the vertebral body and neural elements of the patient.
Figure 40B:
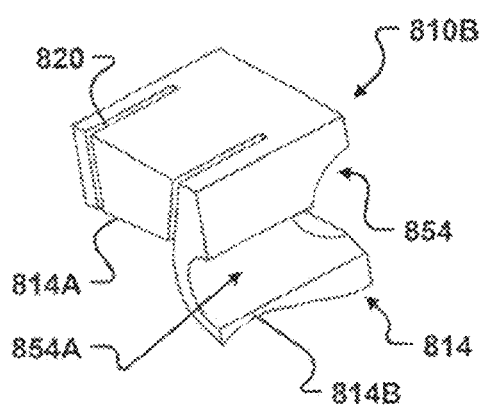
Figure 40C:
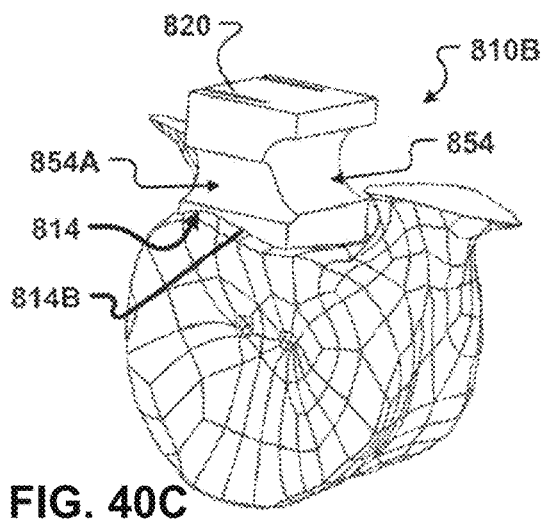
Figure 40D:
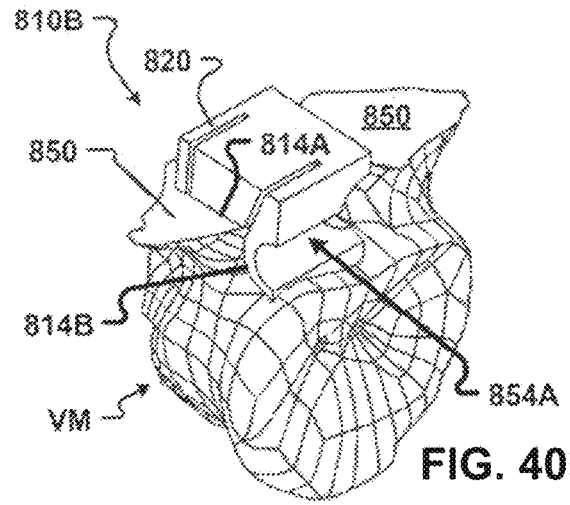
Figure 40E:
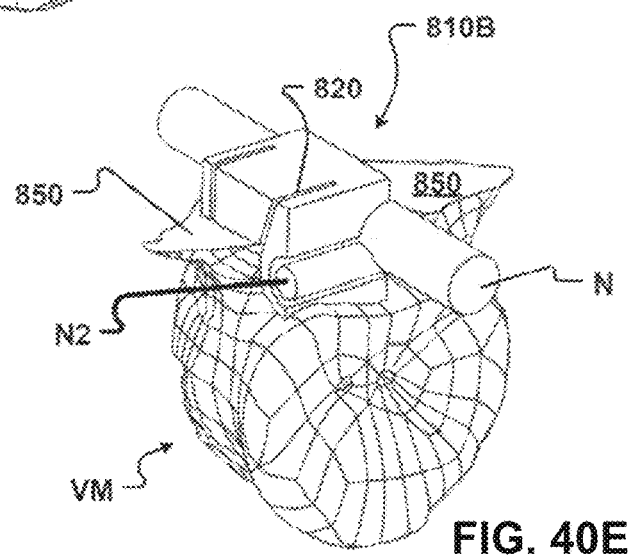

Referring now to FIGS. 38A-38C, a guide 710 of another embodiment of the present disclosure is illustrated. In one embodiment, the guide 710 is adapted for use in a PSO or an APSO procedure. Portions of the posterior of the superior vertebrae VS, medial vertebrae VM, and the inferior vertebrae VI (such as the transverse process, spinous process, lamina, and/or pedicles) are removed by cuts 750 prior to the use of the guide 710.

A frame 730 is interconnected a portion of the patient's spine. The frame generally comprises a medial member 732 connecting two transverse members 733. In one embodiment, the frame 730 is interconnected to the superior vertebrae VS and the inferior vertebrae VI. Pedicle screws 734 positioned in the superior and inferior vertebrae may be used to secure the frame to the vertebrae. In one embodiment, the pedicle screws comprise fixation devices 3634 with a porous material.

The frame 730 may be similar to, and include the features of, the frame 330 described above. Thus, the frame 730 may preserve an existing amount of distraction. In one embodiment, the frame is used to preserve the relationship between the medial vertebrae VM and the adjacent superior and inferior vertebrae VS, VI. Alternatively, the frame is adjustable in order to change the distraction of the construct as necessary. For example, in another embodiment of the present disclosure, the medial member 732 of the frame may have a length that is adjustable during a surgical procedure. Changing the length of the medial member 732 increases or decreases the distance between the transverse members 733. The medial member 732 may comprise a first portion that fits within, or adjacent to, a second portion. The medial member may further comprise a rack and pinion system, threads, or other means for altering the length of the medial member 732 to provide a desire amount of distraction between vertebrae VS, VM, VI. As will be appreciated by one of skill in the art, the frame may have different shapes and sizes. For example, in another embodiment, the frame 730 may comprise two medial members. Each medial member 732 may have a length that is independently adjustable. Still other embodiments of the frame are contemplated for use with the guide of the present disclosure.

Once the frame is in place, the guide 710 is interconnected to the frame. In one embodiment, at least a portion of the guide 710 is adapted to contact a cut surface 750 of a patient's vertebrae. Another portion of the guide 710 may have patient-specific surface adapted to conform to an uncut portion of the patient's vertebrae.

The guide includes cutting tracks 720. The tracks 720 are similar to the other slots described herein, including, without limitation, slots 20, 120, 320. After the guide is interconnected to the frame, the tracks are used to guide cuts into the vertebrae along a predetermined trajectory. Each track 720A, 720B may have a unique patient specific shape. Further, track 720A may have a size and width adapted to receive a specific tool that is different than the tool associated with track 720B.

In one embodiment, the guide 710 includes two tracks to separate the pedicle from the medial vertebrae VM. The tracks may enable the separation of the pedicle in a single cut. The guide 710 may include apertures to guide cuts in other portions of the vertebrae VS, VM, and VI similar to guides 510, 610.

Although not illustrated, the guide 710 may also include cannula similar to cannula 16, 416 describe above. The cannula may receive a fixture (similar to fixture 434) to interconnect the guide 710 to the targeted vertebrae VM. Optionally, the fixture may be placed in a portion of the vertebrae, such as the pedicle, planned for removal by cuts guided by the tracks 720. In this manner, after the cuts are completed, the guide 710 can be removed from the frame to remove the severed portions of the pedicle. In another embodiment, the cannula is adapted to guide an instrument, such as a boring device.

Referring now to FIGS. 39-40, embodiments 810A, 810B of guides of embodiments of the present disclosure are illustrated. The guides are adapted fit to a cut surface 850 of a vertebrae VM that has been formed by removing a portion of the vertebrae. The surface 850 may be formed by a cut guided by another any other guide of the present disclosure. The guides 810A, 810B may also include patient-specific surfaces 814 that are adapted to substantially conform to predetermined portions of the vertebrae. A first portion 814A may be adapted to contact and substantially conform to a cut surface 850 of the patient's anatomy. A second portion 814B of the guide may include patient specific contours adapted to substantially conform to an unaltered portion of the patient's anatomy. The second portion 814B may generally hook around the patient's anatomy. In this manner, the second portion 814B contacts a different plane of the patient's anatomy compared to portion 814A.

The guides 810A, 810B can have a variety of sizes and shapes. In one embodiment, the guides 810 have a size selected to fit at least partially across the surface of the vertebra. Additionally, or alternatively, each guide may include armatures. The armatures may interconnect the guides 810 to a fixture, such as a screw, located in the vertebrae VM or in an adjacent superior or inferior vertebrae VS, VI. The armatures may also contact the vertebra in various locations. Further, the guides 810 may include a cannula similar to cannula 16, 116, 416. The cannula may receive a fixture to interconnect the guide to one of the vertebrae at least during the surgical procedure. Optionally, the cannula may be used to interconnect the guide 810 to a frame such as frames 330, 730. In another embodiment, the cannula are adapted to guide an instrument.

The guides 810 include slots 820 to target portions of the vertebrae. The slots may be the same as, or similar to, the slots of any other guide described herein. The slots may have any orientation and size. In one embodiment, the slots 820A, 820B are positioned in planes that are not parallel to each other. Each slot may have a unique size and may be associated with a specific tool. Further, the slots may receive sleeves, similar to sleeves 24, formed of a durable material, such as a metal, to prevent damage to the guide. The sleeves also prevent the cutting tool guided by the slot from changing the dimensions of the slot.

Although the guides 810 illustrated in FIGS. 39-40 include two slots, it will be appreciated that the guides may include any number of slots. The slots may also have different shapes, including arcuate shapes. Further, the guides 810 may include slots to target both sides of a vertebra. In another embodiment, different guides 810 may be formed to target each of the posterior sides of the vertebrae. In this embodiment, the two guides for each side of the vertebrae may be keyed. The keys enable the guides to be interconnected together during the procedure. In this manner a guide 810 can be assembled that targets both sides of the vertebrae while still protecting neural elements. The keys may optionally be adapted to require a specific assembly sequence of the individual guides.

A recess 854 may be formed in a portion of the guides 810. The recess 854 has a cross-sectional shape selected to at least partially wrap around a neural element N, such as the spinal cord, of the patient. In one embodiment, the recess 854 has a shape similar to a "C" or a vaulted ceiling. The recess 854 includes an interior surface 856, illustrated in FIG. 39A, that is spaced from an interior surface of the slots 820. In this manner, the recess 854 protects the neural element N from inadvertent damage as a tool is guided in the slot 820 to form a cut in the vertebrae.

Referring now to FIG. 40, guide 810B is similar to guide 810A. Additionally, guide 810B includes a second recess 854A which is shaped to protect a second neural network, N2, such as a nerve root, from damage.

In other alternative embodiments of the present disclosure, the apparatus formed by the system and method described above may comprise a tube retractor, which may also comprise a lower patient-contacting surface determined from and/or complementary to a patient's anatomy. This patient-contacting surface may be formed in a section of the tube retractor that is selectively removable from the cylindrical body of the tube retractor, such that the tube retractor may be reused in a number of surgeries while the removeable section is remade or reformed and coupled to the cylindrical body for each patient. The patient-specific contacting surface of the tube retractor is at least partially shaped to match a corresponding surface of surgical interest, which may be at least partially based on patient specific imaging or patient anatomical data obtained prior to the procedure. The tube retractor preferably also comprises a generally hollow inner lumen and at least one tab for manipulating during insertion and that assists the surgeon in ensuring proper alignment of the tube retractor.

The tube retractor may comprise at least one or more aperture(s) for facilitating coupling of the tube retractor to the area of interest on the patient's autonomy. For example, the tube retractor may facilitate the placement of instruments, tools, screws (including pedicle screws) and may allow for better visualization of the patient's anatomical elements. The proximal end of the tube may comprise a lip and/or tab capable of being positioned on the patient's skin to further stabilize the tube at a location removed from the area of surgical interest.

The tube retractor may also facilitate the introduction of Kirschner wire (K-wire) that may be visualized through various imaging systems known in the art, and which may further be used to identify a desired patient-specific marker or location. Such procedure may also allow for successful dilation through the introduction of sequential muscle or soft tissue dilators, which may allow for a quicker, more effective operation. The use of tube retractors, as discussed above, may also prevent the need of additional surgical devices, such as multiple retractors of various sizes, which may substantially reduce the logistics and cost of preparation of an operation.

Other embodiments of the present disclosure may include patient specific insertional guides that may include patient-specific contours or channels that conform to anatomical markers. Such patient specific insertional guides may be used for the placement of external hardware or guide surgical equipment or instrumentation for percutaneous and/or subcutaneous introduction, which may be predetermined using medical imaging and/or computer aided design software as described in conjunction with the systems and methods disclosed herein. In such procedures, the external hardware and/or surgical equipment may be guided via the patient-specific contours or channels by location, axes and/or insertional trajectories, and/or depth to substantially ensure accuracy. In these embodiments, hardware or instrumentation is substantially guided during surgery via predetermined patient-specific anatomical markers on a surgical area of interest. Said another way, at the time of surgery the guide may be placed at a predetermined surgical location, either percutaneously or subcutaneously, that can then direct and facilitate the operation by way of accurate introduction of external hardware or guided surgical equipment or instrumentation, such as, for example, placement of a Jamshidi needle(s) into the pedicles of the spine. Such procedures may also substantially guarantee the safety and reliability of the procedure.

Referring now to FIGS. 41A-41E, another guide 910 of an embodiment of the present disclosure is illustrated. Guide 910 is similar to guides 810A, 810B. In one embodiment, the guide 910 is adapted for use to make final cuts 950 required during a pedicle subtraction osteotomy (or APSO). Guide 910 generally comprises a radiused corner 958, a recess 954, and guide slots 920. After portions of the vertebrae have been removed exposing a neural network N, such as the spinal cord, the guide 910 is placed between the spinal cord and the vertebrae VM. The radiused corner 958 of the guide is shaped to push the neural elements to create a space for the guide between the spinal cord and the vertebrae. The neural element N is then received in the recess 954 which protects the neural element from damage during cutting performed using the slots 920 of the guide 910. The guide includes patient-specific features 914 that allow it to fit in a predetermined location. These features may match with the patient's anatomy (the anterior portion of the spinal canal) or may match to the cutting surfaces 950 generated with earlier guides.

The slots 920 are similar to slots of all embodiments of guides of the present disclosure described herein. Further, sleeves may be placed in the slots 920 to prevent damage or alteration of the slots by cutting tools used in the surgical procedure. The slots may align with previously completed cuts. In this manner, new cuts guided by the slots will intersect the previous cuts so that a portion of the vertebrae may be removed. In one embodiment, the slots 920 are aligned to complete a cut to remove a medial portion of the vertebral body. Although the slots 920 are illustrated on only one side of the guide, it will be appreciated that slots may be formed on each side of the guide. Further, the guide may include a bore or a cannula adapted to guide an instrument or fixation device.

Referring now to FIGS. 42-47, embodiments of models of the present disclosure are illustrated. The models are adapted for use during a surgical procedure, such as an osteotomy, as a reference for the surgeon. One or more of the methods described in the Summary may be used to form a model. For example, after the patient's anatomy is imaged, such as by CT image or other imaging device, a computer model of the anatomy is formed. The model may then be designed with patient-specific features and apertures or surfaces aligning with operations to be performed during the surgical procedure. The model(s) include presurgically planned corrections to the patient's anatomy. For example, the model(s) may include indications of angles and starting locations of multiple cuts required to make planned corrections to patient's alignment. The model(s) can include surfaces and indications aligning with cuts of any size and shape, including cuts that are straight, concave, convex, curvilinear, or 'chevron' shaped. Further, the model(s) can be designed to be modular such that separate portions are interconnected to form the finished model during a surgical procedure. This may be beneficial for models designed to fit around, or conform to, portions of the patient's anatomy with complex exterior contours.

The models may be manufactured by any method. In one embodiment, the models are manufactured using a rapid manufacturing process such as 3D printing, although other processes are contemplated. The models can be fit to the patient's anatomy during surgery to help the surgeon visualize the correct angles and starting locations for cuts, including osteotomy cuts. In one embodiment, the models include cannula. The cannula are adapted to receive fixtures to at least temporarily interconnect the model to portions of the patient's anatomy. Fixtures may also be received in the cannula to interconnect portions of a modular model together.

Referring now to FIGS. 42A-42E, an embodiment of a model 1002 of the present disclosure is illustrated. The model 1002 is designed to include patient specific surfaces 1014 substantially conforming to a portion of the posterior surface of a vertebrae V. In one embodiment, the model is adapted to at least partially fit around a portion of the vertebrae that is planned to be removed during the surgical procedure. In another embodiment, at least a portion of the model is adapted to substantially conform to, or "hook" to, a predetermined portion of the patient's anatomy, such as the vertebrae. Said another way, the model may be adapted to bias into a predetermined orientation with respect to the patient's anatomy. Accordingly, the material of the model 1002 may be selected to allow a surgeon bend or stretch the model 1002 to hook around the patient's anatomy. In one embodiment, the model 1002, or portions thereof, may be manufactured from a material that is at least partially flexible or deformable. In another embodiment, the model is manufactured from a material with shape memory, such as Nitinol. In this manner, when properly aligned with the patient's anatomy as planned, the model 1002 may be releasably retained in a predetermined alignment with respect to the patient's anatomy.

The model 1002 is adapted to indicate entry points and angles of the planned cuts. In one embodiment, the model includes indicia that indicated the entry points. In another embodiment, at least one exterior surface of the model is parallel to the plane of a planned cut. For example, in the embodiment of the model 1002 illustrated in FIG. 42E, exterior surface 1013 is substantially parallel to the plane of a cut planned to remove the spinous process S. Although not illustrated, the model may include slots and cannula to guide cuts and bores into portions of the vertebrae V. As will be appreciated, the size and shape of the model 1002 may vary as planned to guide any variety of cuts. For example, if the thickness of the model 1002 illustrated in FIG. 42E is increased, less of the spinous process S will be removed by a cut guided by surface 1013. In the alternative, more of the spinous process S can be removed by decreasing the height of the model 1002.

Referring now to FIGS. 43A-43F, still another model 1102 of the present disclosure is illustrated. Model 1102 is adapted for use in an asymmetrical pedicle subtraction osteotomy in one embodiment of the present disclosure. Model 1102 is similar to model 1002. Thus, the model may include indicia and other indications of entry points and angles of cuts. However, model 1102 further includes an aperture 1128 that fits around a portion of the vertebrae planned to be removed. In one embodiment, the aperture 1128 has a shape that is asymmetric around a vertical axis substantially parallel to the shorted sides of the model 1102. The aperture 1128 thus forms a window that indicates the bone intended for removal during the asymmetrical pedicle subtraction osteotomy. In one embodiment, proximal surface 1113 of the model 1102 is about parallel to the plane of a cut planned to remove a predetermined portion of the spinous process S.

As will be appreciated, the model 1102 and the aperture 1128 may be of any size and shape. The model also includes a variety of patient matched surfaces 1114 associated with portions of the patient's anatomy similar to the patient specific surfaces 1014 of model 1002. Further, the patient specific surfaces may be formed in voids 1117 formed in the model. The voids are adapted to align the model with the patient's anatomy. The model 1102 may further include projections 1119 with patient specific surfaces 1114 adapted to mate with portions of the patient's anatomy. The combination of voids 1117 and projections 1119 may decrease the possibility of improper placement of the model 1102 in relation to the patient's anatomy.

Figure 44A:
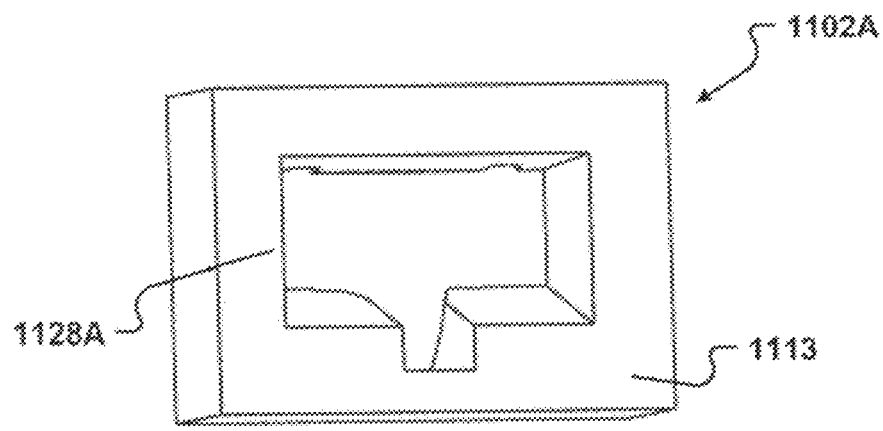
FIG. 44A is a front perspective view of another embodiment of a model of the present disclosure.
Figure 44B:
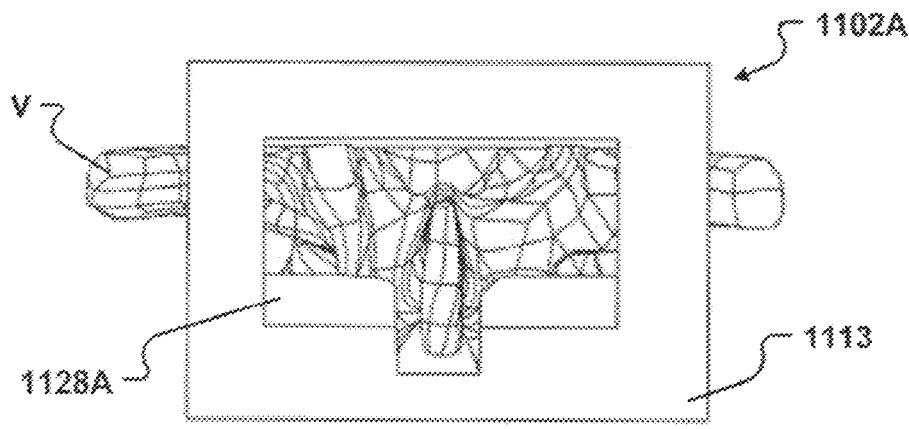
FIG. 44B-44C are a front elevation view and a perspective view of the model of the embodiment of FIG. 44A positioned proximate to a vertebral body.
Figure 44C:
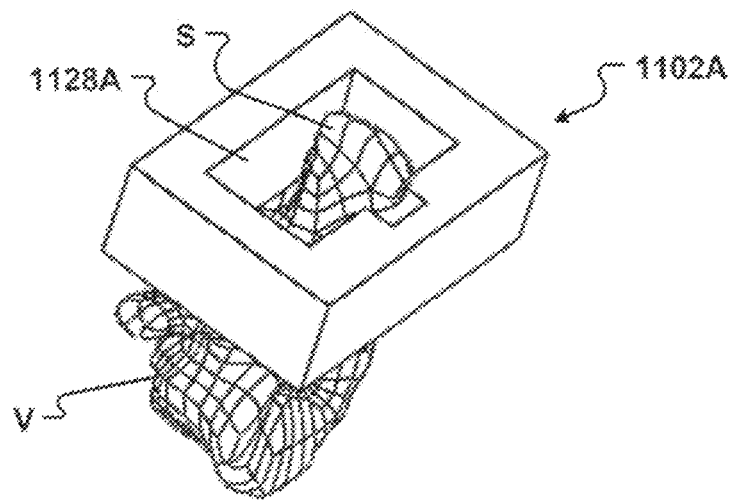
Figure 47A:
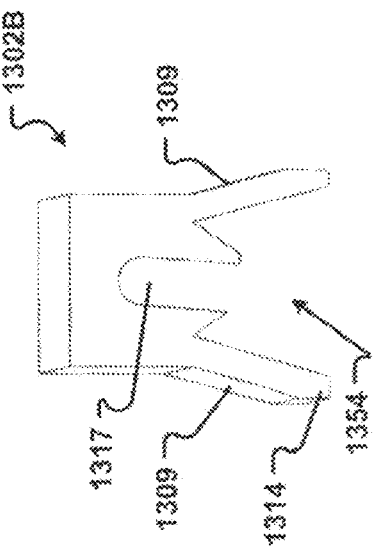
FIG. 47A is a perspective view of another embodiment of a model of the present disclosure.
Figure 47B:
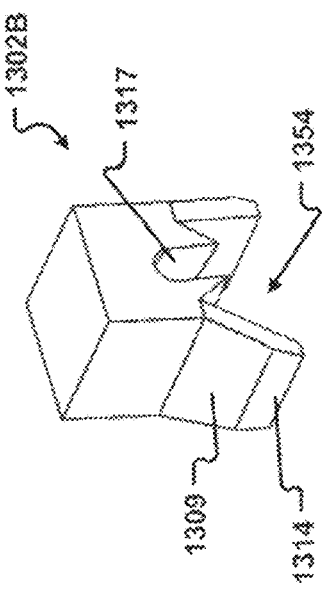
FIG. 47B is a side perspective view of the model of FIG. 47A.
Figure 47C:
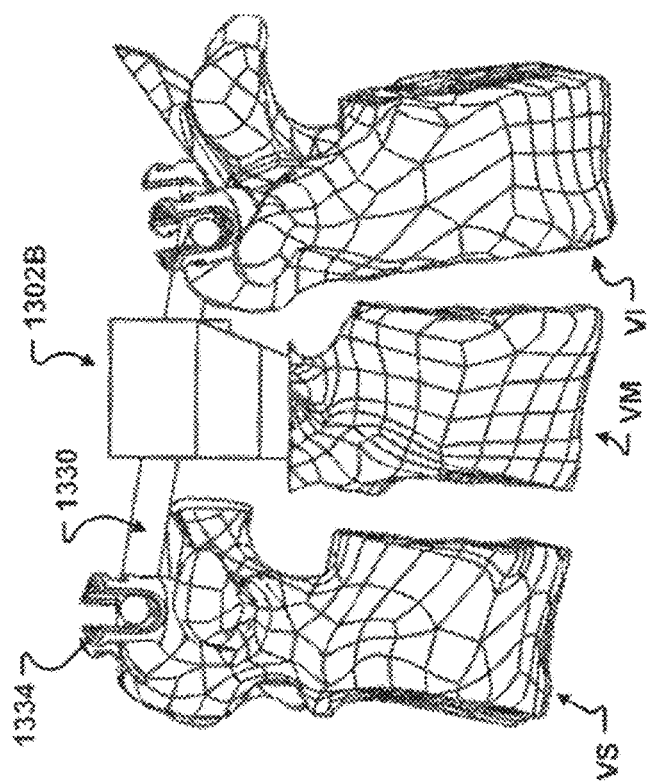
FIGS. 47C-47D are views of the model of FIG. 47A in a position of use interconnected to a frame of the present disclosure, the frame fixed to a portion of a patient's spine.
Figure 47D:
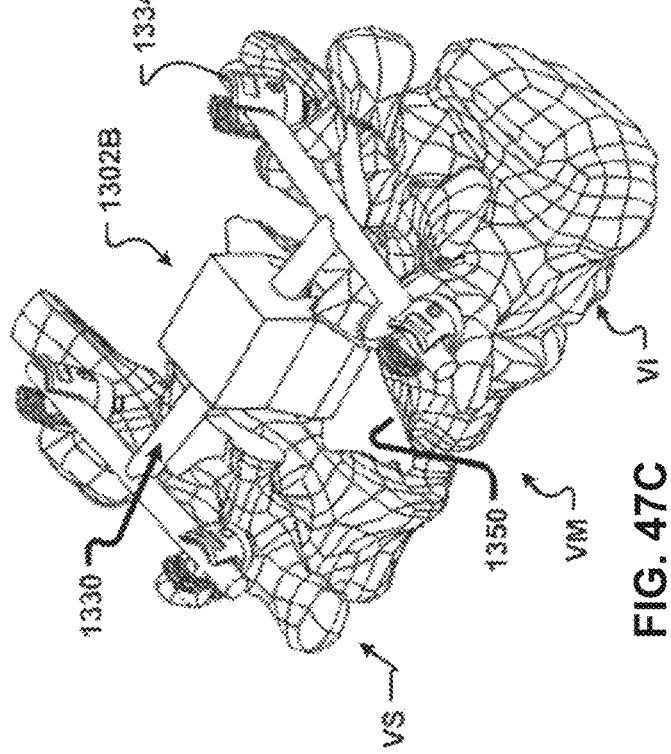

FIGS. 44A-44C illustrate a model 1102A of another embodiment of the present disclosure. Model 1102A is similar to model 1102. However, the aperture 1128A has a different shape that is substantially symmetric about a vertical axis. The aperture 1128A thus forms a window that indicates the bone intended for removal. As will be appreciated, the model and the aperture 1128A may be of any size and shape. In one embodiment, model 1102A is thicker than model 1102. Accordingly, model 1102A may be designed for a procedure in which less of the spinous process S is planned to be removed compared to a procedure using model 1102.

The model 1102A also includes a variety of patient specific surfaces associated with portions of the patient's anatomy similar to the patient specific surfaces 1114 of model 1102. Further, voids and projections may be formed on the model 1102A similar to the voids and projections of model 1102 described above.

Referring now to FIGS. 45A-45E, still another model 1202 of an embodiment of the present disclosure is illustrated. The model 1202 generally comprises a first portion 1208 and a guide portion 1210. In one embodiment, the first portion and the guide portion are integrally formed as one piece. In another embodiment, portions 1208, 1210 are individual pieces adapted to be interconnected before or during a surgical procedure. The features 1260, 1262 are provided to align and interconnect the guide portion 1210 to the first portion 1208. In one embodiment, the features comprise projections 1260 formed on one of the portions adapted to be retained in bores 1262 formed in the other portion. Although the projections are illustrated on the guide portion 1210 and the bores are illustrated on the first portion 1208, it will be appreciated the guide portion and the first portion may each comprise projections and corresponding bores. Further, other features adapted to interconnect and/or align portions 1208, 1210 are contemplated and may be used with the model 1202.

The first portion 1208 is similar to models 1002-1102 described above. Accordingly, the first portion generally includes patient specific surfaces 1214, voids 1217, protrusions 1219, and an aperture 1228 that are the same as (or similar to) the corresponding features of other models and guides described herein.

The guide portion 1210 generally includes tracks 1220 for guiding cutting tools, similar to the slots of all embodiments of the guides described herein. Thus, the tracks 1220 may be of any size and shape. Additionally, the tracks may be sized to receive sleeves and may include stops and keys to guide a direction of use of the cutting tool or limit the depth of insertion of the tool. Further, the tracks 1220 may have an asymmetric alignment.

Referring now to FIGS. 46-47, still more embodiments of models 1302A, 1302B of the present disclosure are illustrated. The models are adapted to dock to a frame 1330. The frame 1330 may be the same as, or similar to, frames 330, 730 described above. Accordingly, models 1302 are adapted to fit with either pre-existing or planned pedicle screws 1334. The models may optionally contact a surface 1350 of the medial vertebrae VM prepared in a previous cutting procedure. However, as will be appreciated by one of skill in the art, the models are not required to contact the medial vertebrae.

The models 1302A, 1302B generally include apertures 1328 and voids 1317 for interconnection to the frame. In one embodiment, the model 1302A includes a closed aperture 1328. Accordingly, the model 1302A is generally interconnected to a medial portion of the frame 1330 before the frame is interconnected to the pedicle screws 1334.

Further, the models may include a recess 1354 similar to recess 854, 954 described above. The recess has a cross-sectional shape similar to at least partially wrap around a neural element, including the spinal cord of the patient. The models may also include indicia that indicate a location to begin a cut and an angle of the cut.

Model 1302A is generally comprised of two portions 1307A, 1307B. Each portion includes a leg or medial surface 1309 that indicates an angle of a planned cut. For example, medial surfaces 1309 are generally in a plane that is parallel to a place formed by a planned cut into the vertebrae. Thus, the space between portions 1307A, 1307B generally indicates the shape of a portion of the vertebrae VM that will be removed. In one embodiment, the medial surface 1309 includes a distal portion with patient specific contours 1314. The patient specific contours may substantially conform to a cut portion 1350 of the patient's anatomy. Optionally, the distal portion of medial surface 1309 may be adapted to contact and substantially conform to an uncut portion of the patient's anatomy.

In contrast, model 1302B comprises one piece. Angles of planned cuts are indicated by legs or exterior surfaces 1309 of the model 1302B proximate to the superior and inferior vertebrae VS, VI. Accordingly, the shape of the model generally indicates the shape of a portion of the vertebrae VM planned for removal. In addition, model 1302B has a void 1317 with an opening for interconnection to the frame 1330. Accordingly, the model 1302B may be added and removed from the frame without disassembling the frame 1330. In one embodiment, distal portions of the surface 1309 include patient specific contours 1314.

One having skill in the art will appreciate that embodiments of patient specific guides, as well as other embodiments discussed herein, may be used in conjunction with devices that employ automated or semi-automated manipulation, such as, for example, robotics, image guidance or other autonomous systems. Embodiments of patient specific guides may also be designed such that the guide may be operated and verified, in whole or in part, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. These apparatus and systems may be programmed to operate with the patient-specific guides, the same having known dimensions and therefore provide ease of validation and operation by automated or semi-automated means.

In one embodiment discussed above, for example, the adjustable arm assembly may be associated with, or controlled by, a robot, programmable apparatus, CNC machinery or equivalent equipment used to perform a surgical procedure. In other embodiments, the guide may be configured for use in conjunction with or to further supplement the use of a navigation device. More specifically, autonomous placement of the patient specific guide via the adjustable arm assembly with the corresponding anatomical feature(s) of the patient assists with one or more of registration, stability, and motion tracking. The navigation device coupled with the adjustable arm assembly and/or patient-specific guide may optionally track the position of instruments, equipment or hardware in relation to the patient's anatomy during a surgical procedure. Accordingly, the navigation device may display positions of instruments, equipment or hardware as they are used during the surgical procedure. In yet other embodiments, the placement of the guide may supplement the registration, stability and motion tracking features provided by the navigation device. In these embodiments, such surgical procedures may be entirely or partly performed via autonomous or semi-autonomous systems and methods so as to limit the exposure of certain harmful or toxic chemicals or transmissions (e.g., radiation) to the surgeon and other attending medical staff. Such autonomous and semi-autonomous systems and methods may also substantially increase the speed and accuracy of the surgical procedure.

Each of the guides described herein can interface with any vertebra level or more than one vertebra level, including without limitation the cervical spine. Further, each of the guides include at least one cannulae. The cannulae may include a bore adapted to guide one or more guide wires, drill bits, taps, and screws. Thus, the bore may guide a drill apparatus and/or a fixation device. Optionally, a cannula may be devoid of a bore. The cannula without a bore is adapted to provide stability as other portions of the guide are used in a surgical procedure. Additionally, or alternatively, the guides may comprise secondary and/or tertiary cannulae adapted to guide one or more of the group comprising guide wires, drill bits, taps, screws, couplings, and other instrumentation including without limitation tools adapted to harvest bone grafts. The cannulae may be of a variety of lengths. In one embodiment, at least a portion of the proximal end of the cannulae and the guide is configured to extend outside of the patient during a surgical procedure.

In one embodiment, at least a portion the guide is reusable. Optionally, at least a portion of the guides projects beyond the patient's anatomy when in a position of use during a surgical procedure. For example, at least a proximal portion of a cannulae of one or more of the guides may project from an incision formed during surgery.

Other benefits achieved from the use of these patient-specific guides include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Additionally, the patient-specific guides may comprise individual pieces that are adapted to be assembled by a surgeon before, or during, a surgical procedure. The portions or components of the guides may be disassembled and delivered to a specific area of the patient's anatomy for assembly during the surgical procedure. For example, the medial bodies, cannulae, and legs of the guides may pass through a bore of a cannula of another tool and assembled during a minimally invasive surgical procedure.

The cannulae may have a generally cylindrical shape but other shapes are contemplated. Each of the two cannulae may have a unique orientation and size. The cannulae may be of any length based at least in part on the specific patient's anatomical features, preferences of the surgeon, orientation of the guide, and the type of tool or fixation device associated with the cannulae. The length of the cannulae may also be selected to provide depth control of instruments guided by the cannulae. For example, in one embodiment, the cannulae has a first length to allow a drill bit to penetrate a first depth into the patient's anatomy. In another example, the cannulae has a second length that is greater than the first length. Accordingly, the cannulae prevents the drill bit from penetrating the first depth into the patient's anatomy.

The cannulae may optionally include extensions of any size or shape. In one embodiment, the extensions are positioned proximate to a distal end of the cannulae. In another embodiment, the extensions wrap at least partially around the exterior of the cannulae. The extensions may also project at least partially beyond the distal end of the cannulae. The extensions are adapted to wrap at least partially around a predetermined portion of the patient's anatomy. In one embodiment, the extensions are adapted to wrap around a portion of one of the pars and the superior articular process.

Additionally, or alternatively, the projections may be asymmetrical. Thus, in one embodiment, one projection has a shape and/or size that is different than another projection. For example, one projection may have a different thickness, contour, or length than the other projection. The asymmetric shape or size of the projections may be planned to contact, or avoid, a predetermined portion of the patient's anatomy. Additionally, the angle and orientation of each projection with respect to the distal end of the cannulae can be varied to match the anatomy of the patient, or to avoid a portion of the patient's anatomy.

In one embodiment of the present disclosure, the bore of the cannulae may facilitate and guide a drill bit, or any other suitable instrument to drill and tap a pilot hole in the cortical trajectory. After the pilot hole is created, the bore may further guide insertion of a fixation device, such as a cortical screw, into the pilot hole. In another embodiment of the present disclosure, the bore may be adapted to receive one or more inserts or guide wires such as the inserts.

In one embodiment, the bore is oriented in a bone screw trajectory. Alternatively, the bore may be oriented in a temporary screw trajectory. In another embodiment comprising a bore in each of the cannulae, the bores may be oriented to target different portions of the patient's anatomy. In still another embodiment, each bore of one or more cannulae is oriented in a plate screw trajectory.

In one embodiment, the cannulae is manufactured out of, or the bore is lined with, a metal or metal alloy that is of sufficient strength and brittleness that breaking and/or flaking is avoided. Further, at least the interior surfaces of the bore may be formed of a material that can withstand the effects of high-speed drilling without damaging the bore or the cannulae or permitting material from the cannulae to become deposited in the drilling site, as well as facilitating re-use of the cannulae. The material of the cannulae may also be selected to withstand temperatures used to sterilize surgical instruments. In one embodiment, the guide comprises one or more of a polymeric material and a metallic material.

Although not illustrated in the appended drawing figures, the guide may further comprise attachment points formed in one or more of the medial body, the cannulae, and the legs. The attachment points are adapted to receive one or more secondary or tertiary cannulae. The cannulae may include a bore or a cutting slot to guide an instrument to target another portion of the patient's anatomy. In one embodiment, the cannulae are adapted to target one or more predetermined portions of the cervical spine (i.e., C1-S1 and ilium).

In one embodiment, the attachment points comprise slots to receive extensions of the cannulae. In one embodiment, the slots may also direct the path of a blade or other cutting instrument, or to receive a measurement aid or tool for facilitating the surgeon/user in identifying landmarks, surrounding boney anatomy, placement of implanted devices, or for surgical planning.

The guide may also include indicia to identify a sequence of use or portions of the patient's anatomy with which the guide is to be used. The indicia may also indicate a tool to be used, a direction of a cut to be performed, or a planned orientation or alignment of the guide. According to one embodiment, the guide may further comprise one or more indicia for identifying the guide with a particular patient.

The guide may be configured to receive one or more inserts. The insert in these embodiments generally comprises a proximal surface, a distal surface, projections extending from the distal surface, an aperture, and bores. The projections are adapted to fit directly to aspects of a patient's anatomy. More specifically, the projections are adapted to be positioned between a superior vertebrae and an inferior vertebrae within the intervertebral disc space. The shape of the projections is predetermined to match at least a portion of a curvature of the adjacent vertebrae and to facilitate the insertion of an implant with a predetermined size and shape into the intervertebral space.

The patient specific surfaces may include any number of protrusions, depressions, and contours to substantially conform to the patient's anatomy. For example, the patient specific surfaces may comprise multiple portions that are adapted to contact two different planes formed by two distinct portions of the patient's anatomy. The patient specific surfaces are adapted to one or more of: align the insert in a predetermined position with respect to the patient's anatomy; hook around a portion of the patient's anatomy; prevent unintended or inadvertent movement of the insert during a surgical procedure; and displace soft tissue. In one embodiment, the patient specific surfaces comprise relatively thin extensions to displace soft tissue. By protruding at least partially around and substantially conforming to different portions of the patient's anatomy, the patient specific surfaces generally "hook" at least partially around (or to) the patient's anatomy. Thus, the surfaces may contact at least two different planes formed by distinct surfaces of the patient's anatomy. Accordingly, the insert is adapted to at least partially fit and substantially conform to predetermined portions of one or more vertebrae during the surgical procedure.

The patient specific surfaces help position the guide and keep it in position in a predetermined position and orientation. The combination of patient specific surfaces formed on various locations of the insert may decrease the possibility of improper placement of the interbody guide in relation to the patient's anatomy. The surgeon may also receive tactile feedback when advancing the insert between two adjacent vertebrae, such as a clip, snap, or vibration when the insert is properly aligned with, and received between, the vertebrae.

The projections may also be adapted to bias into a predetermined orientation with respect to the patient's anatomy. Accordingly, the material of the insert may be selected to allow a surgeon bend or stretch to hook around the patient's anatomy. In one embodiment, the insert or portions thereof, may be manufactured from a material that is at least partially flexible or deformable. In another embodiment, the insert is manufactured from a material with shape memory, such as Nitinol. In this manner, when properly aligned with the patient's anatomy as planned, the insert may be releasably retained in a predetermined alignment with respect to the patient's anatomy.

Additionally, or alternatively, the projections may be asymmetrical. Thus, in one embodiment, one projection has a shape and/or size that is different than the other projection. For example, one projection may have a different thickness, contour, or length than the other projection. The asymmetric shape or size of the projections may be planned to provide a predetermined correction to the patient's spine. Similarly, the asymmetric projections may be shaped for use with a defect of the patient's spine. Additionally, the angle and orientation of each projection with respect to the distal surface of the insert can be varied to match the anatomy of the patient, or to avoid a portion of the patient's anatomy. In one embodiment, the shape of the projections does not provide correction of deformities of the patient's anatomy. In another embodiment, the shape of the projections provides at least some correction of the patient's deformity.

Portions of the projections may have a tapered shape that can be used to distract the vertebrae. For example, the distal portion of each projection may comprise a full-radius or bullet-shaped nose for ease of insertion. Additionally, or alternatively, the distal portions may have a wedge shape.

A variety of patient specific tools can also be pre-operatively planned and manufactured according to the systems and methods described herein to aid in, by way of example but not limitation, verifying final sagittal and/or coronal alignment and/or confirm screw placement. The verification tools are unique to each patient and may contain patient matching surfaces, implant contacting surfaces, and/or capability to mate with a guide. The tools may offer visual or tactical feedback to the surgeon during or after a surgical procedure.

The tools may be adapted to verify coronal alignment during a surgical procedure. Said another way, the tools are preferably used by a surgeon to verify that planned correction of the spine was substantially generated.

Screws as described herein may be placed specifically to interconnect the tools to the patient's anatomy. Screws and other implants may also be patient-specific and may be specific to a particular guide as well. For instance, in certain embodiments the screw may have at least a portion that is configured to be received within a bore of at least one cannula and only advance within the bore if it is the patient-specific screw corresponding to the patent-specific guide that is to be used with the particular screw. The bore may have surfaces that are complementary to the surfaces of the screw or other implant.

Other benefits achieved from the use of these patient-specific interbody guides of all embodiments of the present disclosure include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Additionally, the guides facility quicker bone removal and instrumentation of the patient's boney anatomy, decreasing surgical time and associated risk to the patient. The guides also increase the accuracy of procedures performed using the guide by providing patient matched surfaces to conform to a predetermined alignment of the guide with respect to the patient's anatomy. In this manner, the guides decrease the amount of fluoroscopy required to verify or correct the alignment of the guide, decreasing radian expose to medical staff as well as the patient.

With respect to the embodiments described above, it is expressly understood that such embodiments may be incorporated for use in practicing the novel methods described herein. In certain embodiments, those methods may comprise greater or fewer steps than as described above. By way of example, but not limitation, one step for use with the various embodiments described above may comprise the use of various technologies for capturing a patient's unique morphology, and subsequently mapping and/or planning the fabrication of a device comprising one or more "patient matched" surfaces or features for complementing that unique morphology. Further, such devices may be further optimized with respect to the unique data associated with the patient, such that the device may be matched with specific devices for use during the surgical procedure, or oriented around the patient's own anatomy to achieve, for example, one or more desired insertional trajectories (which may be verified in a pre-operative setting). Variations on this step, and the inclusion or exclusion of additional steps described herein are expressly contemplated by the present disclosure.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

Additionally, although the fusion cages of the present disclosure are particularly well-suited for implantation into the spinal column between two target vertebrae, and although much of the discussion of the present disclosure is directed toward their use in spinal applications, advantages offered by embodiments of the present disclosure may also be realized by implantation at other locations within a patient where the fusion of two or more bony structures may be desired. As one of skill in the art will appreciate, the present disclosure has applications in the general field of skeletal repair and treatment, with particular application to the treatment of spinal injuries and diseases. It should be appreciated, however that the principles of the present disclosure can also find application in other areas.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A patient-specific cutting guide, comprising:
a body having a proximal portion and a distal portion;
at least one patient-specific track formed in the body and oriented in a path determined from the anatomical data of the patient, the at least one patient-specific track extending from the proximal portion to the distal portion of the body of the guide;
the distal portion of the body comprising at least a first patient specific contour on one side of the at least one patient specific track and a second patient-specific contour on the opposite side of the at least one patient specific track for mating with a patient's boney anatomy;
wherein the at least a first and second patient-specific contours are determined from the anatomical data of the patient and are shaped to substantially conform to a specific portion of the patient's boney anatomy.

2. The patient-specific cutting guide of claim 1, wherein the at least one patient-specific track has a predetermined trajectory determined from the anatomical features of a patient and configured to permit an instrument to pass through the body of the guide and make multiple incisions along a patient's boney anatomy.

3. The patient-specific cutting guide of claim 1, wherein the path of the at least one patient-specific track comprises depth control, angle, and orientation for facilitating insertion and movement of an instrument along the path.

4. The patient-specific cutting guide of claim 1, further comprising at least a second patient-specific track formed in the body of the guide.

5. The patient-specific cutting guide of claim 4, wherein the at least a second patient-specific track defines a second path, which comprises depth control, angle, and orientation for facilitating movement of an instrument along the second path.

6. The patient-specific cutting guide of claim 4, wherein the at least one patient-specific track has a predetermined trajectory determined from the anatomical features and the at least a second patient-specific track also has a predetermined trajectory determined from the anatomical features of a patient that is different from the trajectory of the at least one patient-specific track.

7. The patient-specific cutting guide of claim 6, wherein the at least one track and the at least a second track are independently configured to permit an instrument to pass through the body of the guide and make multiple incisions along different depths and trajectories.

8. The patient-specific cutting guide of claim 5, wherein either of the at least a first and second patient-specific tracks is configured to guide an instrument through their respective paths for removal of a specific portion of the patient's boney anatomy.

9. The patient-specific cutting guide of claim 1, wherein the at least a first and second patient-specific contours are configured to contact one or more of a lamina, a pars interarticularis, a portion of a transverse process, a superior articular process, and an inferior articular process.

10. The patient-specific cutting guide of claim 1, wherein the at least a first and second patient-specific contours are configured to contact a portion of a patient's boney anatomy that has previously been modified by a surgeon.

11. The patient-specific cutting guide of claim 1, wherein the at least one track is adapted to receive and guide an instrument for achieving a pedicle subtraction, an osteotomy, a laminectomy, a facetectomy, a Smith-Peterson osteotomy, or a vertebral column resection.

12. The patient-specific cutting guide of claim 1 further comprising a frame configured to be placed at least partially on the boney anatomy of the patient, and wherein the body of the guide may be selectively interconnected to the frame.

13. The patient-specific cutting guide of claim 1, wherein the body is comprised of at least a first and a second section that are selectively interconnected to each other to form the guide.

14. The patient-specific cutting guide of claim 1, wherein the guide is used to perform a first set of incisions along the patient's boney anatomy, and further comprising a second patient-specific cutting guide used to perform a second set of incisions along the patient's boney anatomy.

15. The patient-specific cutting guide of claim 14, wherein the second patient-specific cutting guide comprises at least one patient-specific contour determined from the anatomical data of the patient and shaped to substantially conform to a specific portion of the patient's boney anatomy.

* * * * *